United States Patent
Belleson et al.

[11] 4,037,971
[45] July 26, 1977

[54] INSPECTION TOOL

[75] Inventors: James Garman Belleson, Hillsborough, Calif.; Kendall Clark, Poughkeepsie, N.Y.

[73] Assignee: International Business Machines Corporation, Armonk, N.Y.

[21] Appl. No.: 670,320

[22] Filed: Mar. 25, 1976

Related U.S. Application Data

[62] Division of Ser. No. 592,154, June 30, 1975.

[51] Int. Cl.$^2$ ............................................. G02B 27/17
[52] U.S. Cl. ....................................... 356/199; 350/7; 356/167
[58] Field of Search ................... 250/237 G, 571, 572; 350/6, 7, 285, 286, 287; 356/167, 169, 199, 200, 203

[56] References Cited

U.S. PATENT DOCUMENTS

| | | | |
|---|---|---|---|
| 3,809,806 | 5/1974 | Walker et al. | 350/7 |
| 3,856,412 | 12/1974 | Zanoni | 356/167 |
| B 309,860 | 1/1975 | Starkweather et al. | 350/7 |

*Primary Examiner*—John K. Corbin
*Assistant Examiner*—R. A. Rosenberger
*Attorney, Agent, or Firm*—Henry Powers

[57] ABSTRACT

This patent discloses an improved inspection tool for rapidly inspecting miniature electronic conductor patterns, circuits and the like. The tool focuses a laser beam to a small laser spot that raster scans a large conductor pattern area on the workpiece being inspected. Reflected laser light from the workpiece impinges upon a light detector that generates electrical signals according to the presence or absence of conductor pattern material on the workpiece at the momentary X and Y coordinate of the scanning laser spot. The light detector signals are compared with a previously encoded data image of the correct circuit pattern for the X and Y coordinates of the scanning laser spot. When the signals and the data agree at all X and Y coordinate points the workpiece is accepted. If the signals and the data do not agree at one or more X and Y coordinate points a defect in the circuit pattern is indicated. A defect may indicate out-of-tolerance dimensions, possible electrical short circuits, and/or open circuits. The extent of a defect may be determined by adjacent X and Y coordinate points and suitable computer programming, while workpieces having extended or out-of-tolerance defects are rejected. The improved disclosed inspection tool includes apparatus for automatically compensating for variations in the workpieces, and to effect registration for the scanning laser spot.

14 Claims, 45 Drawing Figures

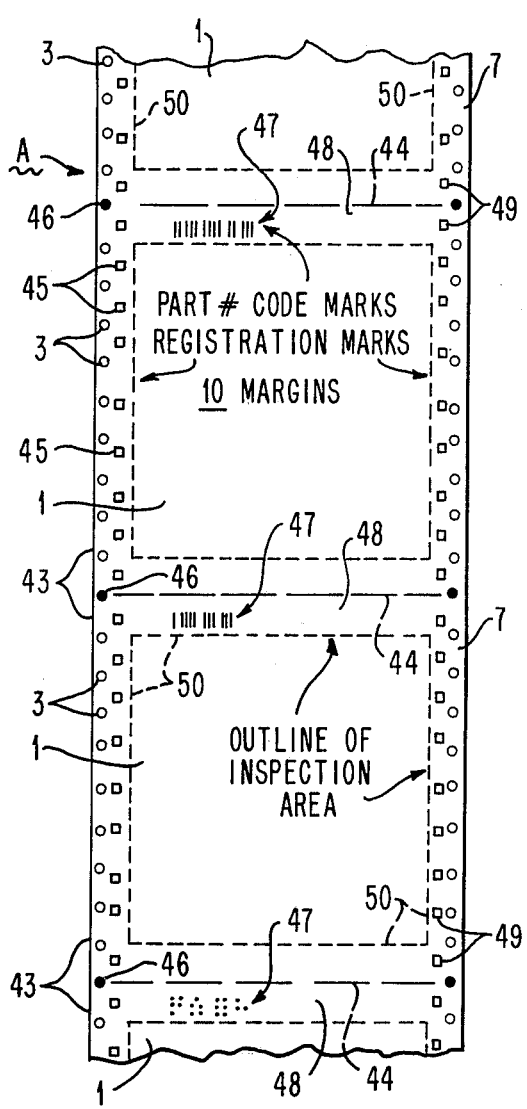
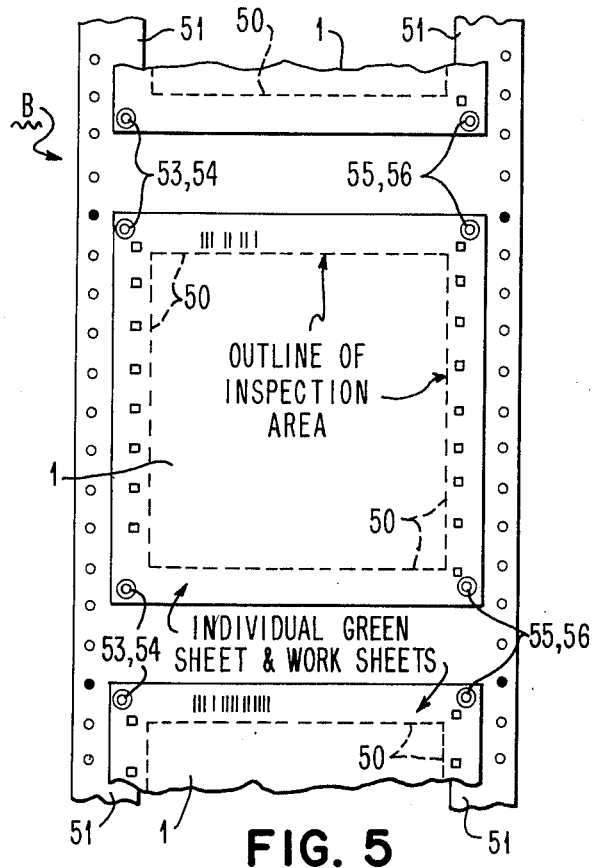
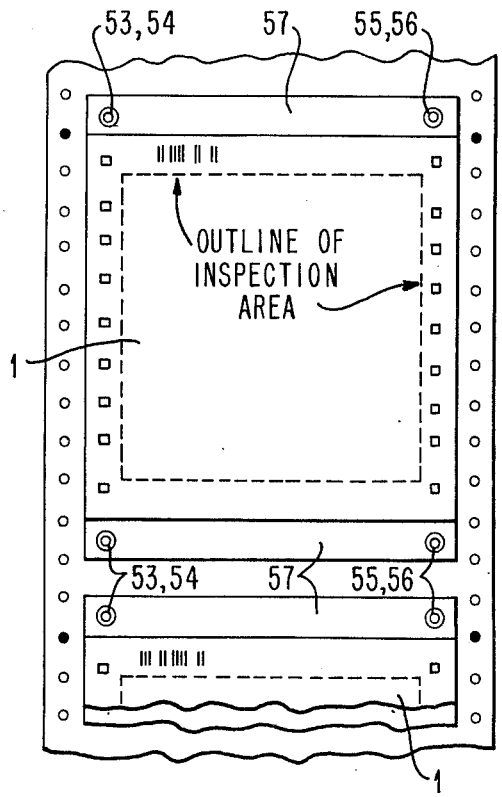
FIG. 4
FIG. 5
FIG. 6

FIG. 7A
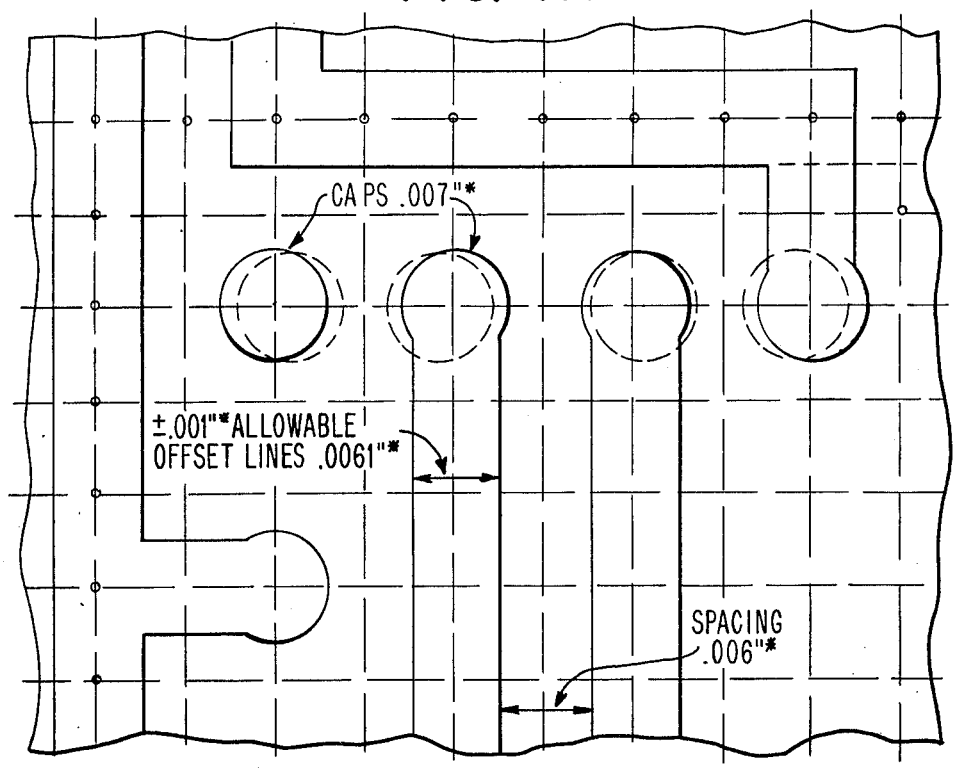
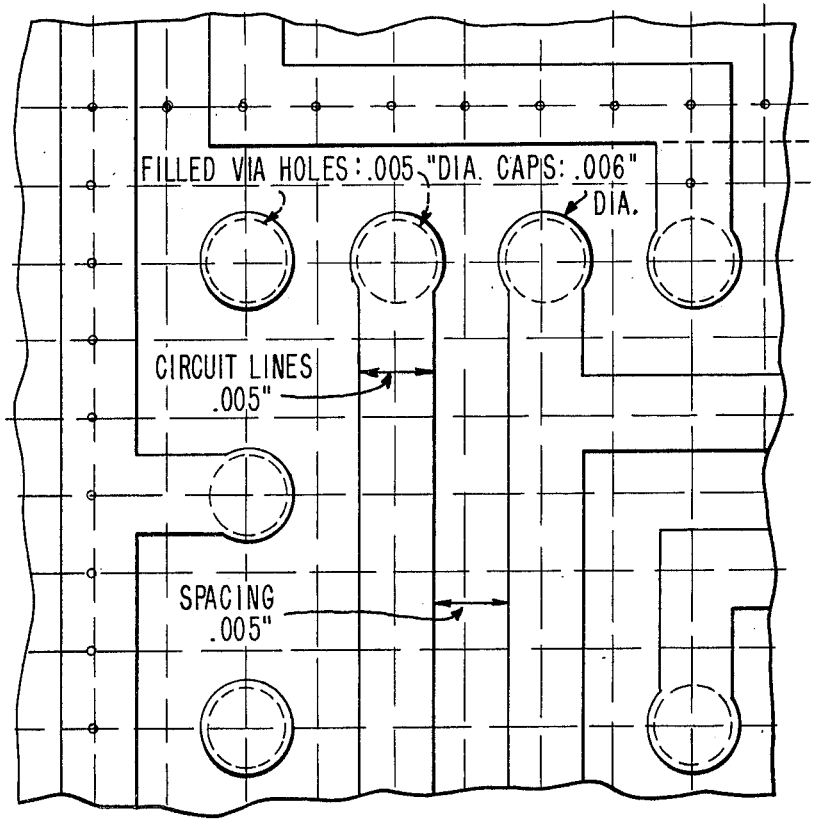
FIG. 7B

FIG. 18B  FIG. 18C  FIG. 18D
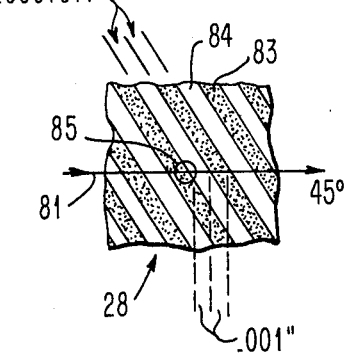 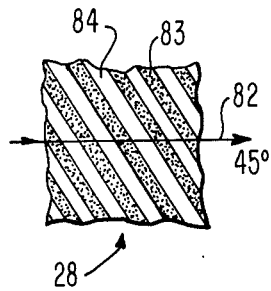 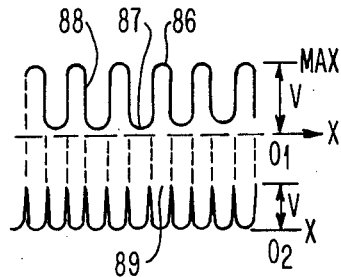
FIG. 18E  FIG. 18F
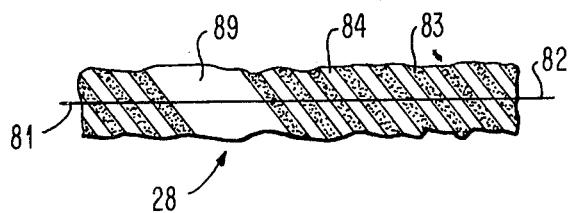 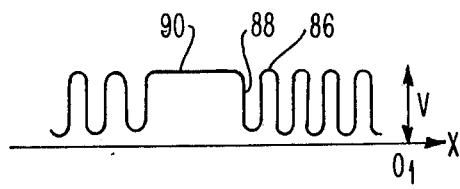

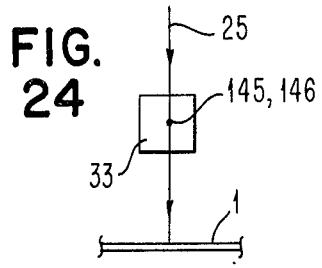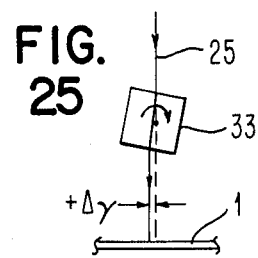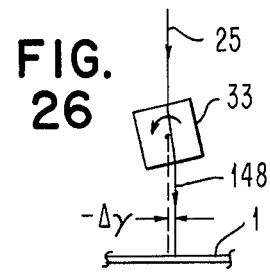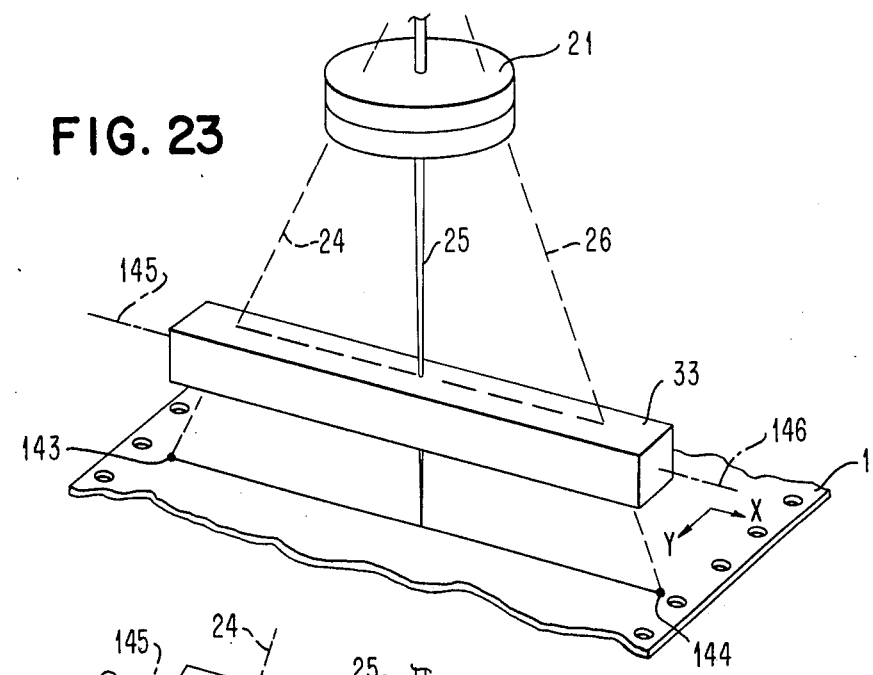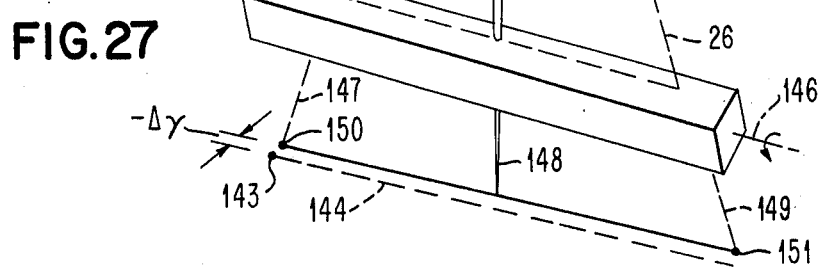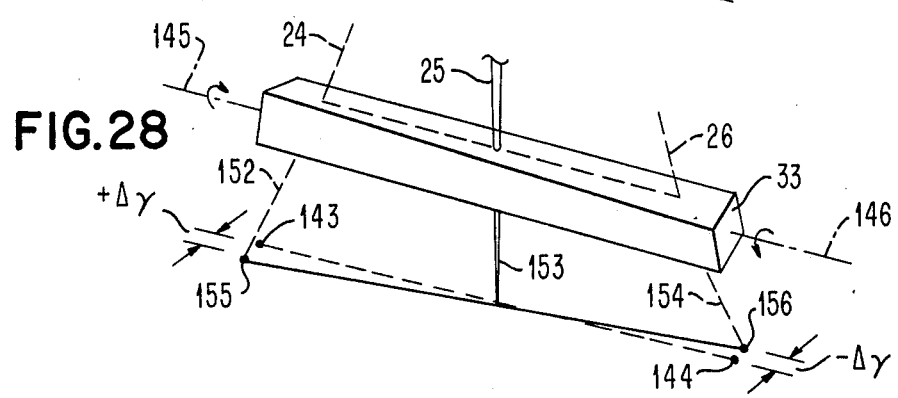

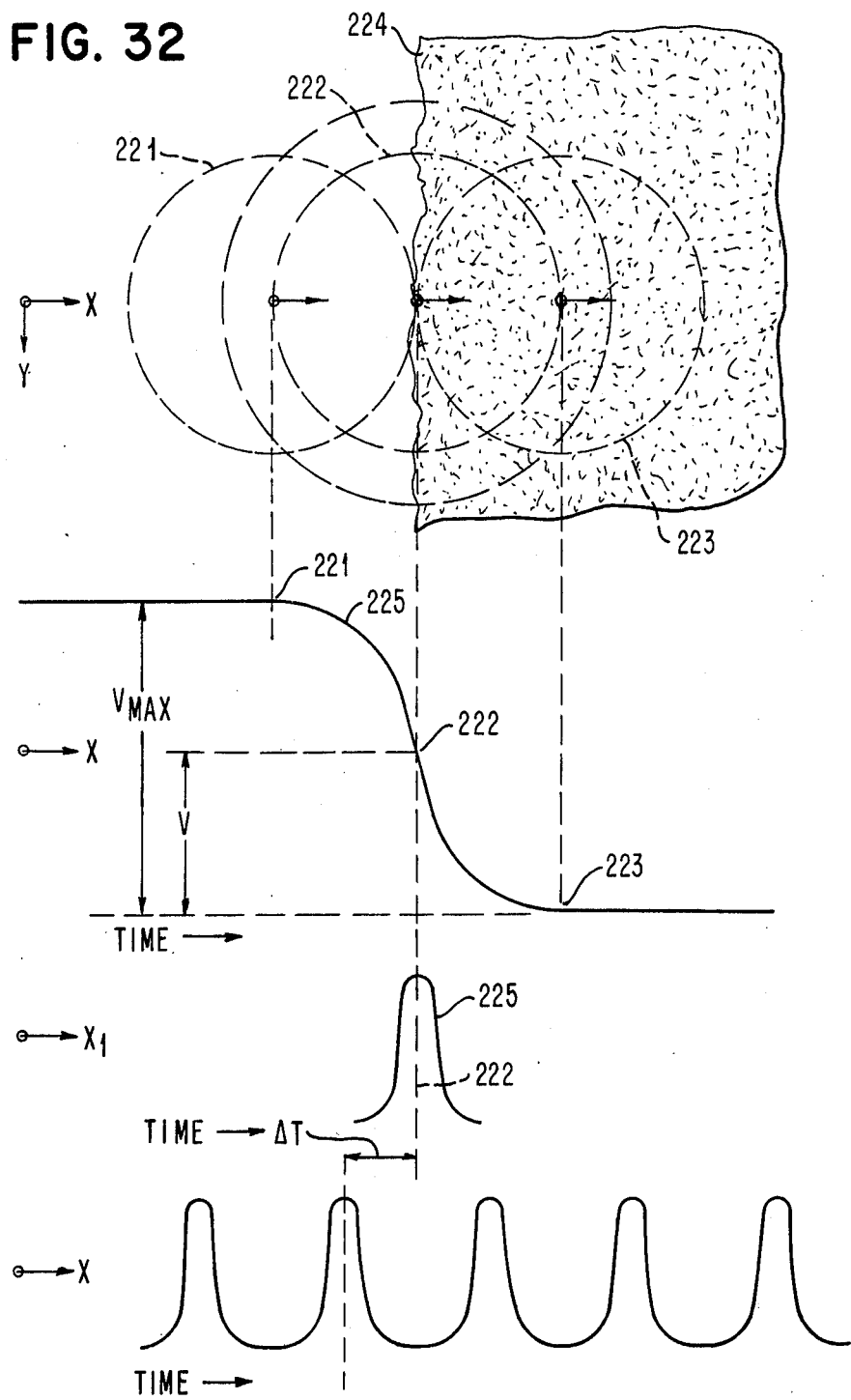

INSPECTION TOOL

This is a division of application Ser. No. 592,154 filed June 30, 1975.

SUMMARY OF THE INVENTION

The present invention relates to a rapid inspection tool for miniature electronic circuit patterns and more particularly relates to an inspection tool that uses a focused laser spot in a raster scan pattern to momentarily illuminate spot areas of the workpiece being inspected. Reflected laser light from the workpiece activates a light detector signal generator. A computer retains a correct data image of the workpiece and the light detector signals are compared with the correct data image to determine the presence of circuit pattern defects. Workpieces having unacceptable pattern defects are treated as rejects. The invention includes means for automatically varying the X and Y coordinate dimensions of the raster scan pattern whereby the raster scan pattern may be registered to variable X and Y coordinate dimensions of the workpiece.

STATE OF THE PRIOR ART

The inspection of miniature electronic conductor patterns has heretofore been primarily dependent upon the visual resolution of the human eye.

The most common inspection procedure for such circuitor conductor patterns has been the use of visual resolution enhanced by a medium power microscope. The field of view of a medium power microscope is usually smaller than the workpiece being inspected, and thus the workpiece or the microscope is usually moved several times to inspect its entire area for electrical short and/or open circuits. Handling and visual inspection may take an experienced operator five to ten minutes for a 6 inch by 6 inch circuit pattern area. Dimensional inspection on a micrometer stage microscope may take another five to ten minutes for inspection and recording dimensions.

Another inspection procedure has been the use of visual resolution with an image combining screen projector. In this inspection procedure, a positive image of the workpiece being inspected is combined and superimposed on a positive image of a correct workpiece. If the sizes of the two images are not identical a magnification adjustment is made. Registration adjustments superimpose one image on the other. The inspection workpiece and the correct workpiece may then be alternately illuminated at about 10 cycles per second. Defects in the workpiece being inspected visually appear to flicker, thus the flicker draws the inspector's attention to the location of the defect and further evaluation of the defect can be made. This procedure is less fatiguing to the inspector than the microscope inspection technique and reduces inspection time somewhat, but such technique is subject to difficulties that limit its utility. For example, differential shrinkage between the X and Y coordinates of the workpiece being inspected may prevent a superimposed image from registering with the correct workpiece image, and thus large areas may appear to flicker. Also, when a 6 inch square workpiece is projected at 4 power magnification onto a 24 inch square screen, short and open circuits 0.001 inch wide become only 0.004 inch wide on the screen and may escape visual observation.

Still another inspection procedure has proposed the use of visual resolution with a color television picture tube that combines the images from two TV cameras. This procedure would be visually similar to the above described procedure except that the flickering of unusual color combinations may be used to indicate circuit pattern defects. By electronic circuit manipulation of one TV camera the black or dark, for example, circuit pattern areas of the workpiece being inspected may be projected by the picture tube as green areas, and the white, for example, insulating areas may be projected as red areas. Similarly, with a second TV camera the black circuit pattern areas of the correct workpiece may be projected as red areas, and the white insulation areas may be projected as green areas. Thus when the images from the two TV cameras are combined, the green from the circuit pattern areas of the inspection workpiece plus the complementary red from the correct circuit pattern area combine and appear as white areas. Such will also occur for the insulating areas where red from the inspection piece and green from the correct piece combine to produce white areas. In effect both the circuit pattern areas together with the insulation areas over the entire workpiece appear to be white. Against this white background short circuits in the inspection conductor pattern stand out as green areas and open circuits stand out as red areas. A cyclic camera scanning rate of about 10 frames per second provide a flicker to enhance visual observation of such conductor pattern defects. The use of this inspection procedure is not considered practical because of inadequate optical resolution. American TV systems use a raster scan of about 530 lines and even a 1200 line raster scan limits optical resolution to about 6.000 inch/1200 = 0.005 inch. An optical resolution of 0.005 inch (or 200 lines per inch resolution) may be inadequate to detect defects such as electrical short and open circuits in the conductor pattern where the defects may be as small as 0.001 inch wide requiring 1000 lines per inch resolution.

One of the greater problems with inspection procedures that depend on manual registration and visual resolution is that the inspectors tend to "go blind" after inspecting a few workpieces, and thereafter the inspectors may accept workpieces having electrical and dimensional defects.

The inspection tool of the present invention avoids the above described difficulties by providing mechanized workpiece handling and registration together with laser optical inspection means having an automated inspection resolution of about 1000 lines per inch.

The inspection tool includes coarse and vernier means for automatically increasing and decreasing the dimensions of the tool's X and Y inspection coordinates thereby to match variable circuit pattern dimensions caused by variable workpiece shrinkage which occurs because of prior processing of the workpieces. A part number reading device scans an encoded part number on each workpiece and selects a corresponding correct data image from the computer data bank for photocell signal comparison. A marking means applies encoded markings to a margin of the workpiece indicating acceptance, or the location and type of a rejection defect. A preferred configuration of the tool may inspect 36,000,000 points over a 6 inch by 6 inch conductor pattern area to an accuracy of 0.001 inch. Modified configurations may inspect a 12 inch by 24 inch circuit board pattern to an accuracy of 0.002 inch, or a 3¼ inch diameter silicon wafer pattern to an accuracy of about 0.00035 inch.

OBJECTS OF THE INVENTION

In view of the above, it is a principal object of the present invention to provide a novel, integrally packaged, inspection tool which may function with integral and/or associated electronic computer means.

Another object of the present invention is to reduce the handling and registration time of a workpiece being inspected by providing mechanized handling and registration for the workpiece.

Still another object of the present invention is to provide means in the inspection tool for compensating for variations in the X and Y coordinates of the workpiece being inspected. Another related object of the invention is to provide gross and vernier adjustments for the X and the Y inspection coordinates of the inspection tool which compensate for variations in coordinates of the workpiece being inspected.

A further object of the invention is to provide a laser raster pattern to illuminate the workpiece being inspected and means for receiving reflected laser light from the workpiece being inspected to determine the presence and absence of conductor pattern material on the workpiece.

A still further object of the invention is to compare the above reflected signals from conductor pattern material to previously encoded and correct data image signals in the computer memory bank whereby differences between the reflected signals and the correct data image signals may indicate a defect in the conductor pattern material.

Yet another further object of the invention is to provide registration marks and patterns on the workpiece being inspected and light or photo detector means for reading and interpreting the registration marks whereby the X and Y adjustable coordinate grids of the inspection tool may be adjusted to match variable X and Y coordinates and registration marks of the workpiece being inspected.

Other objects and a more complete understanding of the invention may be obtained with reference to the specification and claims taken in conjunction with the accompanying drawings wherein:

THE DRAWINGS

FIGS. 4, 5 and 6 are fragmentary schematic views in plan showing several exemplary forms of workpieces that may be inspected in apparatus illustrated in FIGS. 1-3;

FIGS. 7A and 7B are enlarged fragmentary plan views of portions of a typical workpiece pattern, for example, an unsintered ceramic green sheet and a sintered ceramic green sheet;

FIGS. 18B and 18C are fragmentary sectional views taken respectively along lines 18B—18B and 18C—18C of FIG. 18A;

FIG. 18D is a schematic representation of pulse waveforms produced by the laser beam passing over the grating; and representing suitable practical voltage waveforms after rectification and differentiation;

FIG. 18E is a fragmentary plan view of a portion of the apparatus which is modified to permit the location of a starting point for synchronous operation;

FIG. 18F is a schematic representation similar to that shown in FIG. 18D but with respect to the portion of the gating shown in FIG. 18E;

FIG. 23 is a fragmentary perspective view of a portion of the laser optical system with means for vernier alteration of the Y coordinates;

FIG. 24 is an end view of a portion of the means of FIG. 23.

FIGS. 25 and 26 illustrate the vernier effects on the Y coordinates occasioned by the rotation of the means 24;

FIGS. 27 and 28 are fragmentary perspective views similar to FIG. 23 and showing the compensation for skew positions of the workpiece;

FIG. 32 illustrates a laser spot and photocell response curve and voltage patterns corresponding to spot position on a line pattern.

GENERAL DESCRIPTION OF THE INSPECTION TOOL

Figure 1:
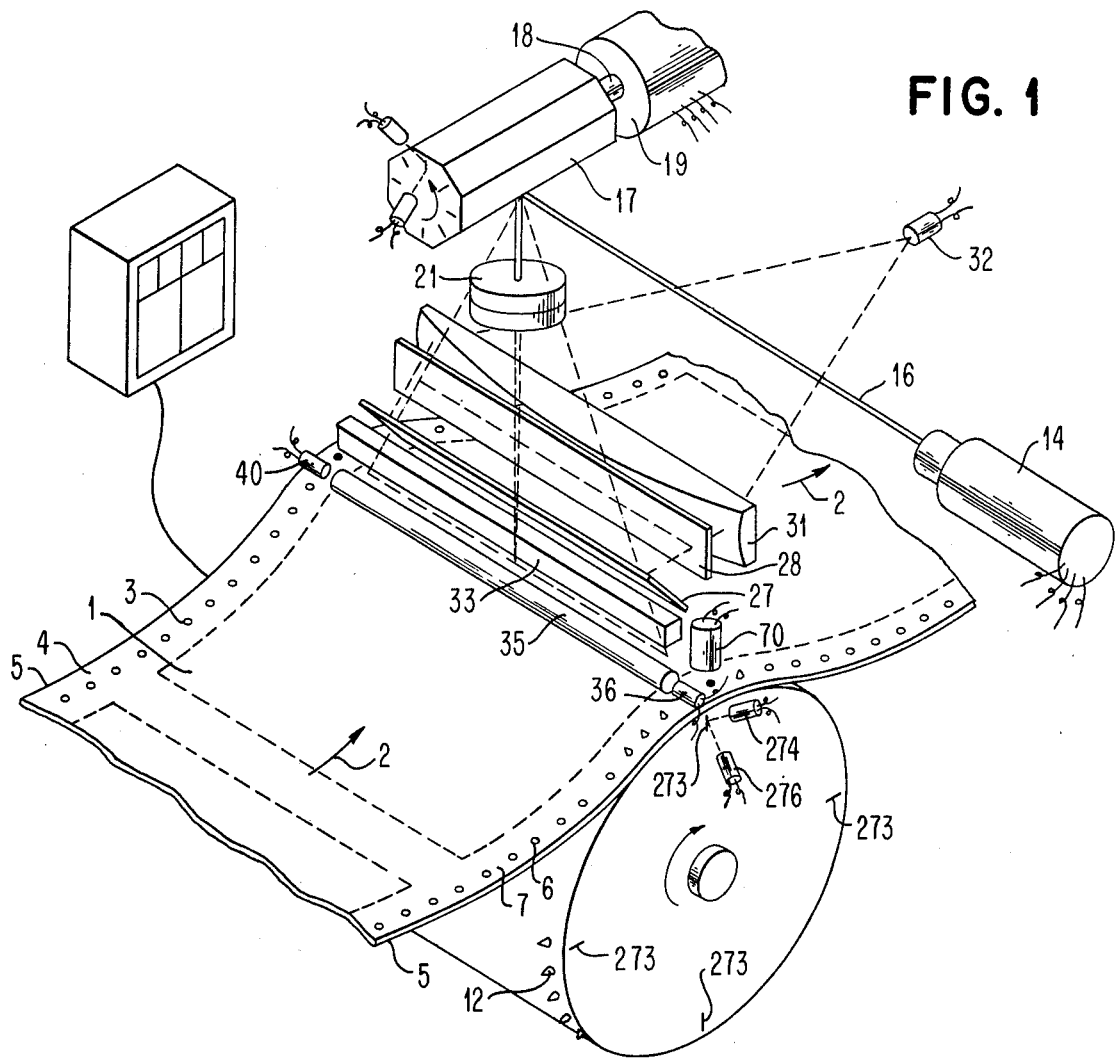
FIG. 1 is a fragmentary schematic perspective view illustrating apparatus constructed in accordance with the present invention for scanning and inspecting workpieces.
Figure 2:
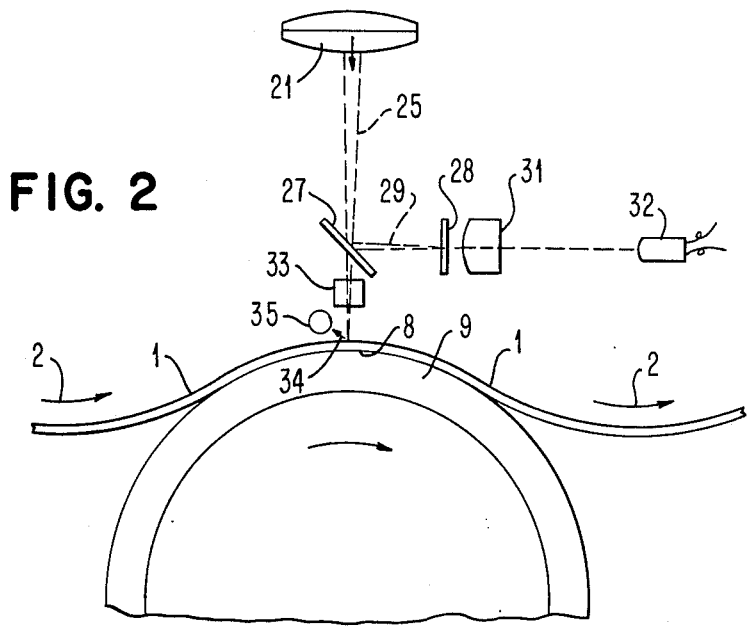
FIG. 2 is a fragmentary schematic and elevational view illustrating part of the apparatus shown in FIG. 1 and showing laser optical paths relative to the workpiece being inspected.
Figure 3:
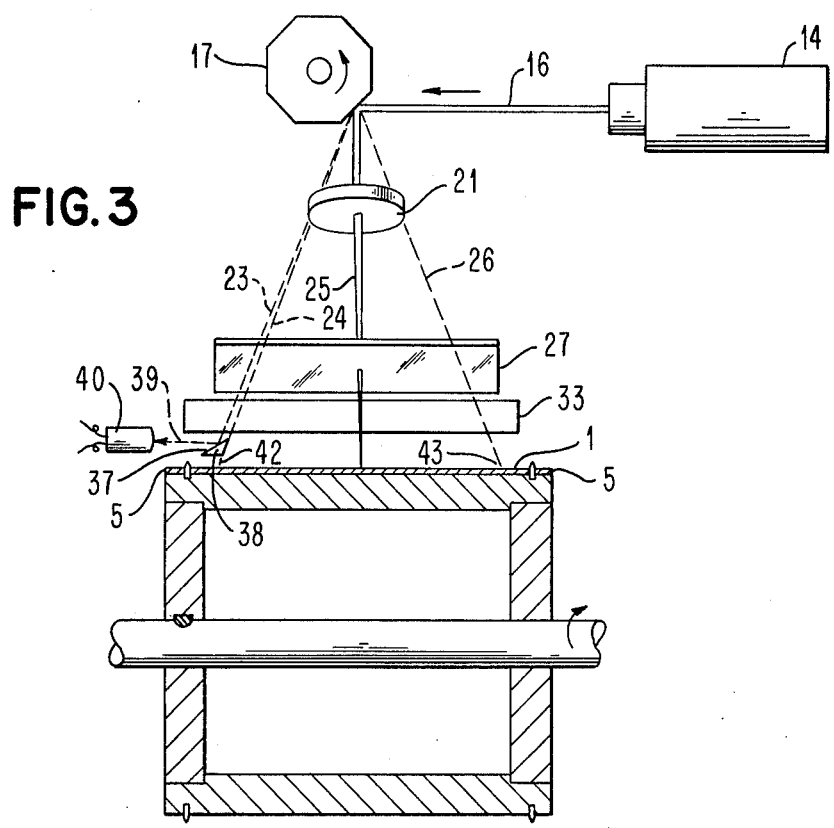
FIG. 3 is a fragmentary schematic front elevational view of the apparatus shown in FIGS. 1 and 2 and the laser optical paths in FIG. 2 from the front.

Referring now to the drawings and particularly to FIGS. 1, 2 and 3 thereof, a workpiece 1, being inspected by the inspection tool of the present invention, moves from left to right in the direction indicated by the motion arrows 2. The workpiece 1, described in more detail hereinafter, is approximately aligned with the inspection tool by accurately located sprocket holes 3 within the left margin 4 and edge 5 of the workpiece 1. Less accurately fitted sprocked holes 6 within the right margin 7 and edge 5 of the workpiece 1 may be employed for handling and interaction with conveyor drive or guide mechanism (not shown). As shown, the workpiece 1 is positioned on the surface 8 of a cylinder 9 with the sprocket holes 3 engaging left sprocket teeth 11 in the cylinder that are designed for an accurate fit in the left sprocket holes 3. The right sprocket holes 6 may have clearance when they engage the right sprocket teeth 12 in the cylinder 9.

A coherent light source, in the present instance, laser 14 projects an approximately collimated beam of laser light 16 onto a rotating multi-facet mirror 17. The mirror 17 is supported by and rotated by a shaft 18, which in turn is driven by a first motor 19. The rotation of the multifacet mirror 17 reflects and sweeps the beam of laser light 16 across an optical surface of a first lens 21. Each facet of the multi-facet rotating mirror 17 serves to reflect and sweep the laser optical axis or beam 25 through a continuous angle as shown by dotted lines 23 and 24 – 26 in FIG. 3. The lens 21 may be arranged to focus the reflected laser beam 16 to a laser spot approximately 0.001 inch diameter continuously on the surface of the workpiece 1 in a work zone during the sweep of the laser optical axis through the angle 23–26. For illustrative purposes the rotating mirror 17 is shown with 8 facets, but it actually may have up to 18 or more facets and the motor 19 may rotate at 6000 or more revolutions per minute. Likewise for illustrative purposes, the lens 21 is shown as a two element cemented doublet, but it actually may employ multiple elements arranged along the laser optical axis before and after the rotating mirror 17.

As shown in FIG. 2, a partially reflecting mirror 27 intercepts and reflects a portion of the laser light being swept (see FIG. 3). The light from the mirror 27 is then reflected on to a grating 28 having a plurality of interdigited light receiving and light transmitting lines thereon. A more detailed description of the X coordinate registration function of the grating 28 is set forth hereinafter. The reflected portion 29 of the sweeping beam 25 intercepts the lines of the grating at an oblique angle as the beam is swept across the work zone. As shown in FIG. 2, the reflection portion 29 is focused to a spot about 0.001 inch diameter at and along the swept surface of the grating 28. The grating 28 allows portions of the sweeping laser light beam 29 to pass through light transmitting portions of the grating and a second lens 31 focuses this light on a first light detector means 32, in the present instance a photocell. A major portion of the laser light sweeping through the angle 23, 24 and 16 passes through the partially reflecting mirror 27 and a flexible prism 33 to become focused to a 0.001 inch spot at and along the surface of the workpiece 1. Subsequent paragraphs provide more detailed descriptions of the Y coordinate registration functions of the flexible prism 33. Diffused and reflected laser light as indicated by the arrow 34, is reflected from the 0.001 inch focused laser spot sweeping the workpiece 1, and a portion of this diffused and reflected laser light 34 enters a transparent light conductor rod 35. One or more second light detector means or photocell signal generators 36 located at one or more ends of the transparent light conductor rod 35 pick up and convert a portion of the reflected laser light 34 into electrical signals to indicate the presence or absence of different lines on the workpiece.

As shown in FIG. 3, a fully reflecting mirror surface 37 on a small prism 38 intercepts a portion of the angular sweep at 23 and 24 of the laser beams 25 being swept through the angle 23–26. The intercepted portion 23 and 24 of the sweeping laser beam 25 is reflected by the mirror surface 37 in a direction indicated by dotted reflection line 39 to a third light detector means or photocell signal generator 40. The mirror surface 37 and the small prism 38 may be manually adjusted to left or right and may be useful for adjusting and defining the left intersection 42 of a laser beam spot with the workpiece 1. A right intersection 43 and the scan line 42 and 43 on the workpiece 1 may represent the useful portion of the sweeping laser scanning spot as the spot is swept across the workpiece 1. The intersections 42, 43 may be considered to be the end points of the laser beam axis lines 24 and 26 respectively as the rotating mirror 17 sweeps the laser ray axis line through the angle 23, 24, and 26.

It is to be understood that the elements of the inspection tool of this invention may be positioned, adjusted and journaled for cooperating spatial relationships approximately as shown by the drawings in a suitable frame or chassis (not shown).

THE WORKPIECE(S)

A brief description of the workpiece(s) 1 and associated FIGS. 4 to 16 may provide a better understanding of the various features of the inspection tool of the present invention. At the outset it should be understood that the workpieces may take any of a number of forms and the one described hereinafter is utilized to indicate a worse case condition.

The workpiece 1 may be initially formed from a casting slurry that includes about 95% powdered alumna and about 5% powdered glass as solids mixed with a liquid that includes a plastic monomer and a volatile liquid vehicle. The slurry is poured on a plastic transport web and passes under a wide "doctor blade" that regulates the thickness of the cast slurry to about 0.013 inches. After the solids settle and the volatile liquid vehicle evaporates the workpiece material 1 reduces to a long and/or continuous web about 0.008 inches thick. After or during further drying and/or stabilizing, the plastic transport web is stripped off and may be cleaned and reused for another slurry casting. At this point in the processing sequence, the web of workpiece material 1 may be inverted such that the bottom smooth side that was formerly in contact with the plastic transport web is on the top side, the left and right edges 5 and the sprocket holes 3, 6, and/or the alignment holes 53, 55 may now be mechanically punched to the configurations of FIGS. 4 and/or 5.

Via holes 58 (FIGS. 7 and 8) about 0.006 inches diameter may be pierced through the workpiece 1 using mechanical punching, electron beam, laser beam and other means. The via holes 58 are formed at predetermined locations and may be filled with suitable electrically conductive material as well as patterns on the surface of the workpiece 1. One such suitable electrically conductive material might include powdered molybdemum, a plastic monomer, and a volatile liquid vehicle, mixed to form a paste that may be screened or otherwise suitable applied to the workpiece 1. It should be noted that forming of the via holes 58 in the workpiece 1 may distort the integrity of various dimensions of the workpiece. Likewise the Application of the pattern of electrically conductive material to the workpiece 1 may distort various dimensions. As will be more fully explained hereinafter, several features of this invention have been directed to detecting out-of-tolerance distortion of various dimensions of the workpiece 1. After the Application of a pattern to the workpiece 1, and drying, the workpiece may be ready for inspection by the inspection tool of this invention.

As shown in a preferred configuration in FIG. 4, the workpiece 1 to be inspected may be one or more parts of a long and/or continuous web 43 of material having one or more adjacent workpieces 1. When one or more workpieces 1 are present on the long and/or continuous web 43, long dash lines 44 represent the shearing and/or separation points for and/or between the individual workpieces. Accurate sprocket holes 3 and registration marks 45 may be located in the left hand margin 4 of the workpiece 1. Note that sprocket holes 3 (and teeth 11, FIG. 1) may be omitted at positions 46 as indicated by black dots near the left end of the separation line 44 for purposes of aligning the workpieces 1 with the rotational position of the cylinder 9. Machine readable part numbers 47 may be encoded in the leading marginal edge 48 of the workpieces 1. The part numbers 47 may be either suitable combinations of lines and spaces or the like and/or suitable groups of perforated holes, whichever is most convenient for previous processing operations. In a like manner, locational registration marks 49 and the clearance sprocket holes 6 may be located in the right margin 7 of the workpieces 1. A conductor pattern area or like pattern area to be inspected may be generally within the short dash outline 50.

FIG. 5 shows another configuration for the workpieces 1. Here the workpieces 1 may have been previously separated along the lines 44 (FIG. 4) and then located on and/or bonded to a web of flexible material 51. For example, the web 51 may be composed of stainless steel, fiberglass, and the like and may include apertures 51 somewhat larger than the outlines of the short dash lines 50 so that the inspected pattern area may be punched out of the workpiece 1. The workpieces 1 in this configuration may optionally have accurately located alignment holes 53 located near the left top and bottom corners. The web of material 51 then may have accurately located alignment pins 54 secured to the web and closely fitting the alignment holes 53. Alignment and handling holes 55 near the right top and bottom corners of the workpiece 1 may have clearance to corresponding pins 56. Other numerals in the configuration of FIG. 5 provide essentially the same functions as previously described relative to FIG. 4.

FIG. 6 shows still another configuration for the workpiece(s) 1. In this instance the workpiece(s) 1 may be a rigid glass plate bonded to a carrier 57. Other numerals in the configuration of FIG. 6 provide essentially the same functions as previously described relative to FIGS. 4 and 5. Note that in the workpiece configurations of FIGS. 4, 5 and 6, the areas to be inspected are generally defined by dash outlines 50. The dash lines 50 may enclose an area of about 24 inches by 12 inches for circuit patterns on circuit boards made of fiberglass epoxy and the like; or may enclose an area of about 6 inches by 6 inches for patterns on unsintered ceramic material and the like. The diameter of the focused and raster scanning laser spot is preferably approximately proportional to the length of the X coordinate scan line, i.e., for a 12 inch wide fiberglass board and pattern, 0.002 inches; and for a 6 inch wide pattern on ceramic 0.001 inches. Thus, widths larger than 12 inches or smaller than 6 inches may be inspected with proportionately sized raster scanning laser spots.

Figure 8A:
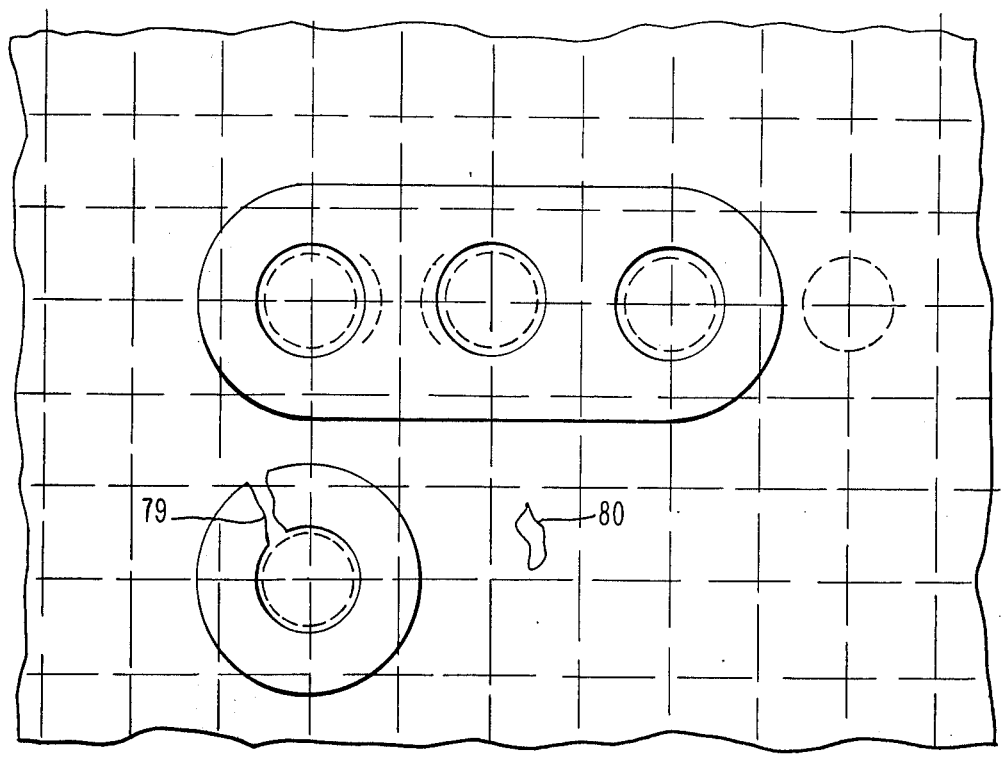
FIG. 8A is an enlarged fragmentary plan view of a small corner portion of the workpiece illustrated in FIGS. 7A and 7B and illustrating typical electrical circuit defects such as electrical shorts and opens, prior to lamination and sintering.

FIGS. 7A and 8A show larger scale plan view portions of two among many types of various patterns that may be inspected on the surface of an unsintered ceramic material or workpiece 1. In this instance, the surface of the workpiece 1 within and/or adjacent the dash lines 50 may be partially or wholly covered by patterns similar to FIGS. 7A or 8A and/or a combination thereof. Patterns such as FIG. 7A and/or the like may be known as "circuit line," "interconnection" and "fan-out" plane patterns. Patterns such as 8A and/or the like may be known as "ground" and "voltage" plane patterns.

The circuit pattern 59 of FIG. 7A may be formed of powdered conductive material, such as molybdenum paste, about 0.006 inches wide and 0.0012 inches thick. The circuit lines 59 may run horizontal, vertical, or at various angles in and/or on the surface of the workpiece 1. The circuit lines 59 may be independent and/or interconnected with other circuit lines and/or "caps" 60. The caps 60 may be about 0.007 inches diameter and may be used as interconnectors to circuit lines 59 and/or via holes 58 and to aid in proper filling of line 0.006 inch diameter via holes with conductive material such as molybdenum screening paste. Planar conductors 61 of FIG. 8A may be about 0.0012 inches thick, of dried molybdenum screening paste covering small and/or large areas on the surface of workpiece 1. Doughnut or oval shaped insulating areas about 0.017 inches across may be positioned at suitable locations within the planar conductor 61 surrounding screened caps 60 and filled via holes 58. The caps 60 may provide interconnections between filled via holes 58, circuit lines 59, and planar conductors 61 wherever interconnections may be required by the circuit design.

The above described dimensions may be considered as applying only to small portions of a pattern on a workpiece 1 to be inspected, such as may be illustrated by FIGS. 7A and 8A. Over a large portion of the workpiece 1, small dimensional errors and/or defects may be cumulative, resulting in overall workpiece patterns that may have larger dimensions than nominal dimensions. Thus, for manufacturing and assembly purposes plus (+) and minus (−) limits to nominal dimensions may be established to avoid electrical short and/or open circuits due to cumulative dimensional errors. Manufacturing experience has indicated that expansion or contraction of a circuit pattern due to cumulative errors from via hole piercing and/or circuit pattern Application, may be approximately linear within and/or near the outlines of dash lines 50 (FIGS. 4, 5 and 6). The cumulative dimensional errors may have, most effect near the corners of a pattern area. Thus while the patterns of various workpieces 1 having the same part number may be geometrically similar, each workpiece may have slightly different dimensions for the corner locations of the dash lines 50 due to cumulative dimensional and/or shrinkage and/or expansion errors. For inspection purposes, nominal dimensions based on previous manufacturing experience may be assumed together with plus (+) and minus (−) deviations from nominal dimensions so that a plurality of workpieces may be assembled in superimposed relation without causing additional errors. The inspection tool includes means that are adaptable for inspecting such geometrically similar patterns having nominal dimensions together with (+) and minus (−) dimensional deviations thereof. However, for practical assembly purposes, the deviations at the corners of dash lines 50 for unsintered ceramic patterns may be limited to ± 0.001 inch X and/or Y tolerance deviations by the design of the patterns such as shown in FIGS. 7A and 8A and as explained hereinafter. Thus the inspecting tool may include means for inspecting and accepting patterns having nominal dimensions and geometrically similar patterns having ± 0.001 inch deviations therefrom at the corners, and rejecting patterns exceeding ± 0.001 inch tolerance deviations.

The inspection process for dimensions, electrical short circuits and open circuits, etc. is described in more detail in later paragraphs. It should be mentioned here however, that a marking device(s) 70 (FIG. 1) may be activated and arranged to place appropriate markings in the right hand margin of the workpiece 1. Visible and/or machine readable markings in a suitable code by the marking device(s) 70 might indicate information such as: A = accept, R = reject, S = short circuit, O = open circuit + or − = ± non-acceptable dimensions, and other coded information. In general, error and/or dimensional markings such as S, O, +, − etc. may be placed in the right hand margin near the laser scan line that has detected such errors during inspection. Such locations for S and/or O markings may assist in locating these pattern errors if machine and/or manual correction of the error(s) is required. The A and/or R markings may be placed near the lower right hand corner of the outline dash lines 50 following the inspection of the workpiece 1.

After inspection, the inspection accepted and/or a marked workpieces 1 may be separated from their transport web and planar stacked one above another in layers of 5 to 30 or more workpieces 1. Each workpiece 1 may have a different part number and a different conductor pattern but they all should be within acceptable ± dimensional tolerances for stacking purposes. The correct vertical stacking alignment (one above another) may be provided by electro-optical-mechanical automation (not shown) and/or the mechanical use of long alignment pins (not shown) fitting the sprocket holes 3 (FIG. 4) or the alignment holes 53 (FIG. 5). Preferably, each successive layer of stacked workpieces 1 should be rotated 90° relative to the layer under it during stacking to equalize shrinkage factors in later process operations.

When the stacking operation has been completed the stacked layers of workpieces 1 may be laminated under heat and pressure. During the laminating process the plastic monomer 10, the work sheets becomes plastic and polymerizes to bind the stacked layers of work sheets 1 together into a rigid (unsintered) planar structure that may be removed as a unit from the laminating fixture (not shown). During proper laminating there may be little or no significant changes in the planar dimensions of the workpieces 1, but the thickness of the stacked assembly of work sheets may be reduced considerably under the laminating pressure. However, an exception to "no significant change in planar dimensions" has been noted: The ends of an open circuit in a planar molybdenum conductor pattern that may be separated by 0.001 inches or less may be frequently squeezed together in a planar direction by the laminating pressure, thereby changing the open circuit to an acceptable pattern without an open circuit.

Figure 9:
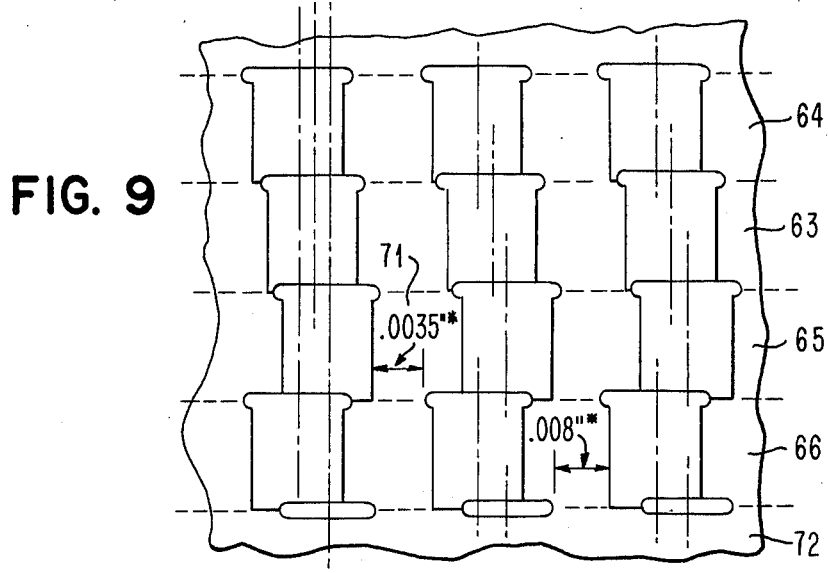
FIG. 9 is an enlarged fragmentary sectional view taken along line 9—9 of FIG. 7.

FIG. 9 illustrates the ± dimensional tolerance limitations that may be followed by the designer of unsintered circuit patterns such as are shown in FIGS. 7A and 8A. FIG. 9 is a vertical cross section through a group of laminated workpieces 1 taken through molybdenum paste filled via holes 58, their caps 60 and circuit lines 59 (see FIGS. 7A and/or 8A) for reference locations near the upper left corner of dash lines 50 (FIGS. 4, 5 and 6). A nominally dimensioned workpiece layer 63 is shown laminated to a 0.001 inch wider workpiece layer 64 above layer 63 and a 0.001 inch narrower workpiece layer 65 below layer 63. It may be observed that the filled via 58 and their caps 60 provide adequate interconnections when stacked in the described sequence. However, when a 0.001 inch narrower than nominal workpiece 65 is stacked above a 0.001 inch wider than nominal workpiece 66, the center lines of these respective via holes 58 and caps 60 may then be offset by as much as 0.002 inch. As such electrical interconnection between the filled via hole 58 of layer 65 and the cap 60 of layer 66 may still be adequate but the cap 60 of layer 65 (in center column of via holes and caps as shown) may come as close as 0.0035 inches to the via hole 60 at location 71 (near left column of via holes and caps). A 0.0035 inch separation is about the minimum of safe insulation separation for stacking design purposes considering that vertical stacking tolerance in the stacking operation add another ± 0.0005 inch of misalignment tolerances between layers 65 and 66. The cumulative stacking tolerances might thus improve insluation separation to 0.0045 inches or reduce the insulation separation to as little as 0.0025 inches. A line pattern area layer such as layer 72 generally causes less spacing problem areas than area containing caps such as caps 62. Similar conditions may also occur near the other three corners of the dash lines 50. Larger workpieces may have proportionately less dense patterns and use larger dimensional tolerances, and smaller workpieces with denser patterns may use smaller dimensional tolerances. However, for a 6 inch square workpiece area such as previously described and illustrated relative to the corners of outline dash lines 50, a manufacturing and/or use tolerance in X and/or Y of ± 0.001 inch from nominal dimensions may provide useful trade-offs. In the above instance a ± 0.001 inch tolerance in X and Y dimensions may be a compromise among various conflicting factors, such as a circuit designers desire for a denser circuit patterns and a manufacturers desire for high production yields (resulting from wider insulating spacings and few internal short circuits in the stacked assembly of workpieces 1 as shown in FIG. 9). Thus the inspection tool should be adaptable to accept nominal pattern dimensions up to 6 inches square but also ±

0.001 inch deviations in geometrically similar patterns, and rejecting patterns exceeding the ± 0.001 inch deviations that may occur in the corners of the dash lines 50 (FIGS. 4, 5 and 6). The nominal corner location is shown by the (circled) dot 73 in the center of FIG. 10. Various X and/or Y locations for the extreme ± 0.001 inch corners locations of the outlined dash line 50 are shown by 8 surrounding dots such as a dot 74 each, up to ± 0.001 inch in X and/or Y from the nominal position of dot 73. Thus considering cumulative tolerances the corner locations overall from top left corner to top right corner of 50 may be overall ± 0.002 inches but not exceeding 0.001 inches from nominal in any one corner of the dash line pattern outline 50 in the X coordinate dimension. Likewise the top to bottom pattern of corners in the 50 outline may be as much as ± 0.002 inches overall but not exceeding ± 0.001 from nominal in any one corner in the Y coordinate dimension. The circle around dot 73 is not actually present, but the circle is used here to distinguish a nominal corner location 73 from other possible corner locations indicated by dots such as 74 that may be otherwise located up to ± 0.001 inch in X and/or Y coordinates from the nominal location 73. The effects of such dimensional tolerances on the sizes and shapes of patterns to be inspected may be made more apparent by a brief description relative to FIGS. 11 to 16.

Figure 11:
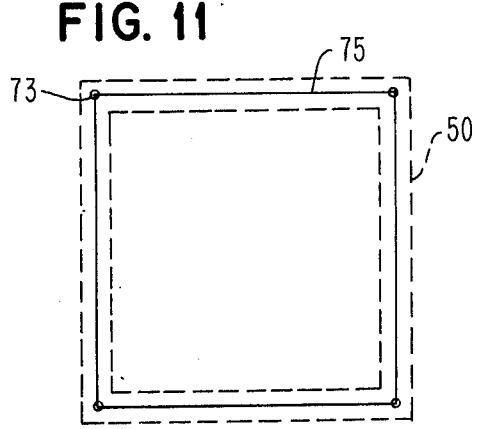
FIGS. 11 through 16 are schematic illustrations of several exemplary workpieces which even though distorted, may be assembled for stacking and laminating.
Figure 14:
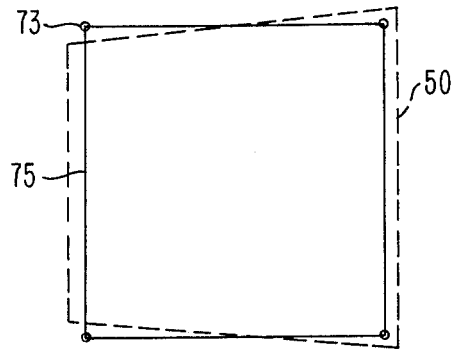
Figure 12:
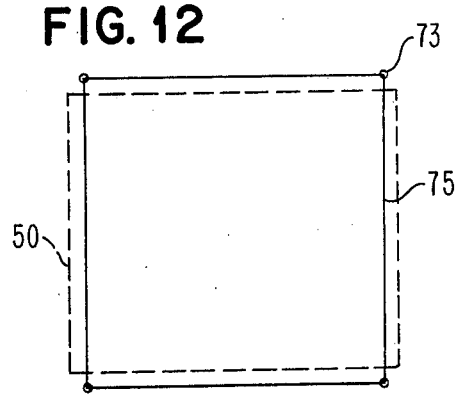
Figure 15:
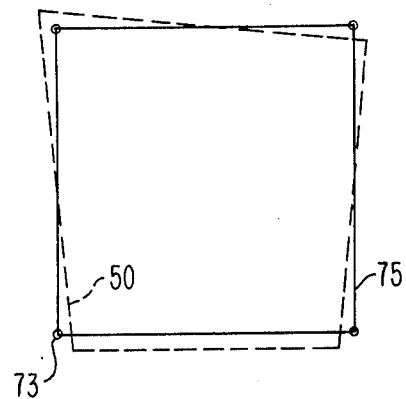
Figure 13:
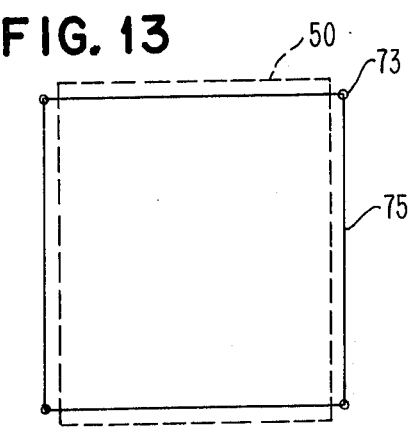
Figure 16:
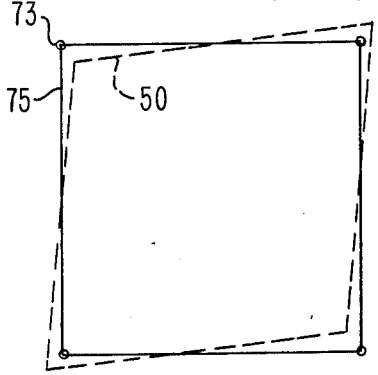

In FIGS. 11 to 16 the sizes and shapes of nominal patterns to be inspected may be shown by the dash lines 50 as previously described. The light solid lines 75 may show the outlines of a few of the other patterns having dimensions other than nominal. The corners of the other than nominal outlines in FIGS. 11 to 16, as may be formed by the solid lines 75, should occur within ± 0.001 inch in X and/or Y coordinates from nominal corner locations. When the corners of lines 75 comply with the above corner tolerance dimensions any of solid line 75 patterns or the dash line 50 patterns of FIGS. 11 and 16 may be stacked one above another after inspection as previously described. The vertical section FIG. 9 also shows the effects of ± 0.001 inch tolerances in stacking. The outlines 50 and 75 of FIG. 11 show geometrically similar outlines. However, the shrinkage and/or expansion of the workpiece 1 may be slightly different along X and/or Y coordinates resulting in other outlines 75 such as in FIGS. 12 to 16 that may not be exactly geometrically similar to the nominal outlines 50. These other outlines 74 may be acceptable for stacking and laminating assembly purposes when the corners of the outlines 75 are within ± 0.001 inch in X and/or Y of the nominal corners of the outlines 50. Thus the inspection tool should be capable of inspecting the workpiece(s) 1 having patterns within these other outlines 75. In some instances these other outlines 75 may be skewed in X and/or Y directions as shown in FIGS. 14 to 16, but since such workpiece(s) 1 might be stacked and laminated satisfactorily the inspection tool should be capable of inspecting them.

Figure 17:
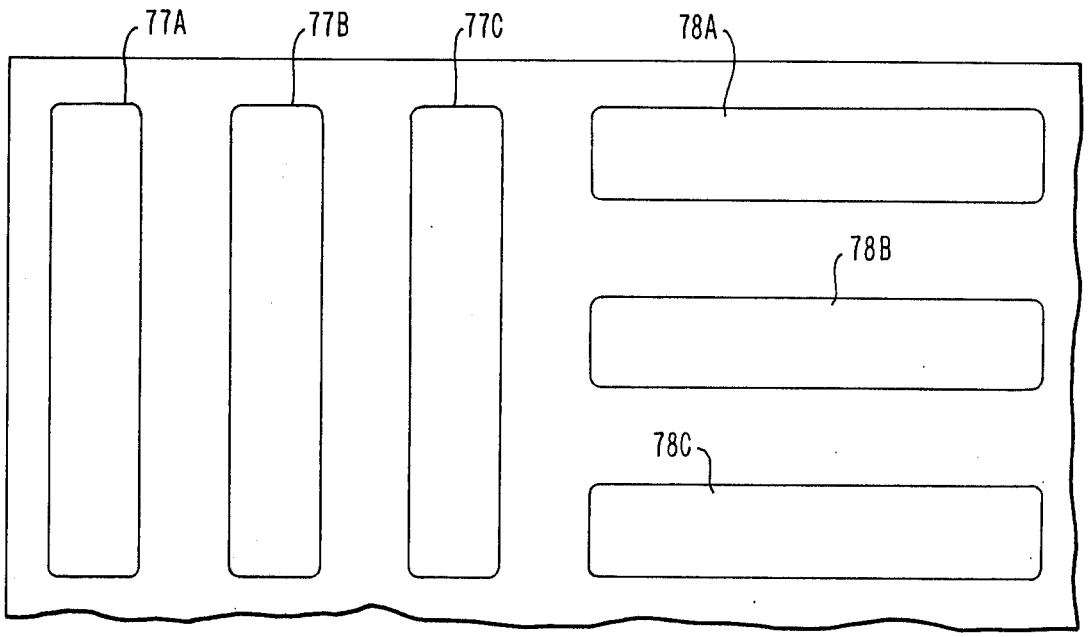
FIG. 17 is an enlarged fragmentary view of one corner of a workpiece with a registration pattern taken thereon and from FIG. 4.

As an aid in the alignment and registration of the inspection tool to the pattern areas to be inspected on the workpiece(s) 1 registration patterns 76 such as shown enlarged in FIG. 17 may be accurately located near the pattern areas (see also FIGS. 1, 2 and 3). Among many shapes that may be used for registration pattern purposes the shape shown in FIG. 17 may be convenient to use since its design corresponds to optical definition and/or resolution patterns and may also be used as such. The three vertical lines 77 of FIG. 17 may be 0.006 inches wide with 0.006 inches spacing between them. The three horizontal lines 78 may be 0.006 inches high with 0.006 inches spacing. The vertical and/or horizontal lines may be 0.030 inches long. A preferred location of the registration patterns 76 (FIGS. 1, 2 and 3) may be in margin areas outside the pattern outlines 50 and/or 75 of work sheet 1. The locations of the registration patterns 76 may be the same relative to all the other pattern outlines 50 and/or 75 of patterns to be inspected except for proportional shrinkage or expansion of the workpiece 1.

Preferably the registration patterns 76 may be applied to the worksheet 1 in a fixed dimensional relationship to the outlines 50 and/or 75 of the conductor patterns. The registration patterns 76 may be applied in the same operation simultaneously with the applications of conductor patterns within the outlines 50 and/or 75 on the worksheet(s) 1. With this simultaneous application of patterns any subsequent shrinkage or expansion of the worksheet may cause concurrent and corresponding dimensional changes for both the registration patterns 76 and the circuit patterns within the outlines 50 and/or 75. By applying two registration patterns, one near the upper left corner and the other near the upper right corner of outlines 50 and/or 75, an X-coordinate measurement between the two corner registration patterns may be compared to the dimensions of their nominal positions to determine their dimensional deviations from nominal. Such dimensional deviations may occur from shrinkage or expansion of the workpiece 1. Thus these measured deviations may then be used in calculating corresponding dimensional deviations for the upper corners of the pattern outlines 50 and/or 75 without actually measuring the corner locations. A similar procedure using a lower pair of separated registration patterns may be used to calculate dimensional deviations for the lower left and right corners of the pattern outline 50 and/or 75. Likewise Y-coordinate deviations from nominal locations may be calculated by measuring the dimension between a pair of Y-coordinate separated registration patterns might be respectively located near the left upper and lower corners, or the right upper and lower corners of the pattern outlines 50 and/or 75. Additionally, dimensional shifts and/or skews of the registration patterns 76 relative to the left sprocket holes 3 (FIG. 1) or registration holes 53, 54 (FIG. 5) may be used to calculate the corresponding shifts and/or skews of the circuit pattern outlines 50 and/or 75. Multiple registration patterns in X and/or Y coordinate locations may be used to enhance deviation measurements. In summary, the measured deviations of the registration patterns from nominal may be measured and used by the inspection tool to align and register the tool's laser raster scan pattern to various patterns being inspected as may be understood from later descriptive paragraphs.

Now that the subject of dimensional deviations from normal has been described for a worksheet 1, some of the causes for such dimensional deviations may be explained. The worksheet material may be constantly shrinking at a diminishing shrinkage rate as the curing time increases due to progressive evaporation of its original liquid casting vehicle. Thus if the worksheet 1 is made from different lots of worksheet material that have been made at different time periods the individual worksheets as made from such different lots of material will have different shrinkage rates prior to stacking assembly. Additionally, the molybdenum paste composition of circuit patterns applied to the worksheets includes a liquid vehicle. A portion of this liquid vehicle may evaporate but also a portion of the liquid vehicle may be absorbed by the worksheets and result in an expansion of the worksheets. Among the different circuit pattern designs some patterns have a greater pattern density on the workpiece than others (compare FIG. 8A with FIG. 7A) and thus require more molybdenum paste. Such denser patterns may provide more liquid vehicle to be absorbed and increase the expansion of the worksheet relative to less dense circuit patterns. Then while the circuit patterns are dried to evaporate most of the liquid vehicle, some of the vehicle evaporates from the worksheet material and the worksheet may start to shrink again. From the aboe explanation of some causes for dimensional deviations it may be understood that the workpiece 1 is constantly subject to some type and/or types of dimensional changes prior to inspection of the circuit patterns by the inspection for excessive dimensional changes while worksheets may deviate from nominal but may be acceptable for stacking assembly purposes provided that such deviations do not exceed ±0.001 inch from nominal dimensions in X and/or Y coordinates.

In order to detect dimensinal deviations from the nominal as small as ±0.001 inch the size of the inspection tool's scanning laser spot may preferably be about 0.001 inch diameter. This diameter of the scanning laser spot may also enable the inspection tool to detect typical electrical short and/or open circuits as small as about 0.001 inch wide. Referring back to FIGS. 7A, 8A, such typical short circuits 79 and electrical open circuits 80 are shown in the circuit patterns and may be classified by the inspection tool as electrical defects and be ejected. Defects smaller than about 0.001 inch wide may be detected down to a width where photocell signal response becomes lost in an environment of "noise" signals. Such smaller width short circuits, if previously undetected during inspection may occasionally be "blown" after sintering by passing a high current through then thereby eliminating the short circuit. Likewise such open circuits may become closed circuits during laminating where the laminating pressure may squeeze the ends of molybdenum conductor paste together. Wider electrical defects may be detected and rejected by the inspection tool. The detection ability of 0.001 inch scanning laser spot may be dependent on the percentage area of the spots laser energy that may be reflected by the surface of the white worksheet or absorbed by the black circuit pattern areas that have been applied to the white worksheet. Accordingly, the detection ability of a scanning laser spot may be useful to detect the edges of larger conductor circuit lines to about ⅛ the diameter of the laser spot before the photocell response signals become obscured by the electrical "noise" of the detection system. The detection ability of a laser spot is described in more detail in later paragraphs.

As a general summary of typical workpieces defects it may now be understood that substantially all of such typical defects may be detected by a scanning laser spot about 0.001 inch diameter as used by the inspection tool. After inspection the accepted workpieces are stacked, laminated and sintered.

The Sintering Process

Figure 8B:
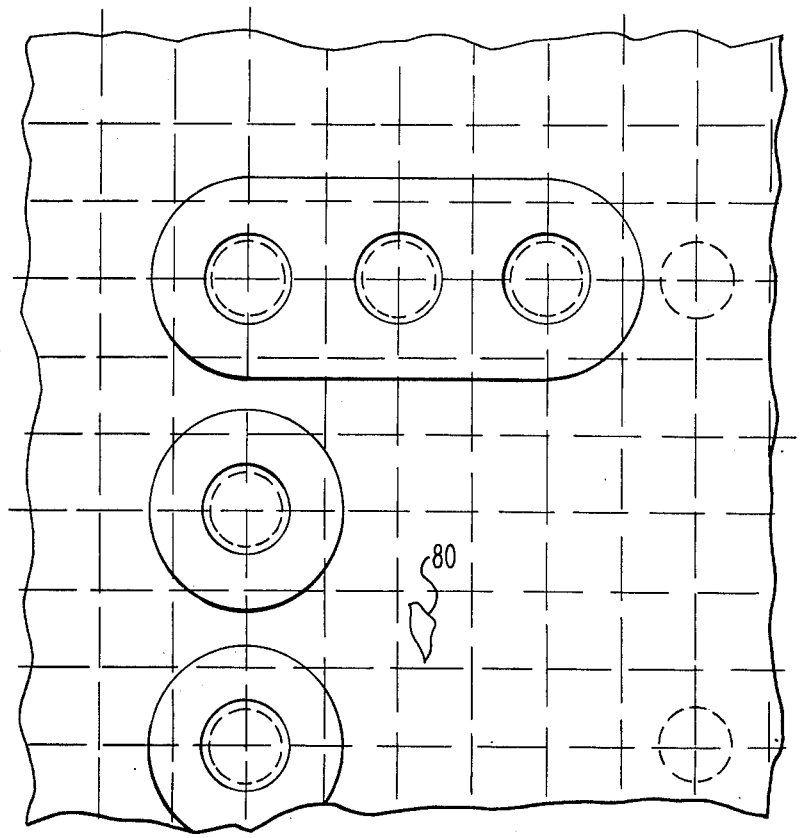
FIG. 8B is an enlarged fragmentary plan view of a small corner portion for another typical workpiece, such as may be used for circuit design and layout purposes and after stacking, lamination and sintering.
Figure 10:
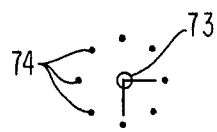
FIG. 10 is a representation of the acceptable location of the conductor pattern corner outlines as represented by a locus of dots, that may be within maximum dimensional tolerances for stacking and laminating.

The sintering process may be described as a separate topic because of the large dimensional change that may occur as the laminated workpieces 1 are sintered. During sintering the material of the unsintered workpieces and their conductor patterns coalesce and their dimensions may shrink by about 17.2% ± 1.5%. The sintering process converts the alumna particles etc. of the laminated sheets into a vitrified alumna ceramic. The molybdenum particles of the circuit patterns during sintering, convert and bond to each other into continuous conductor circuit lines of metallic molybdenum. Insulating spaces between conductor circuit lines are preserved as insulating spaces in the vitrified ceramic. In the sintering process the laminated workpieces are placed on, for example, a flat alumna tile and then heated in a suitable high temperature furnace in a hydrogen atmosphere at about 1600° C for about 24 hours. After cooling, the top and bottom of the rigid ceramic plate or substrate is then inspected by the inspection tool in a manner similar to the inspection of a rigid glass master plate (see FIG. 6). However, for this type of inspection the rigid plates are preferably fed into the inspection tool in a manner such that the action line of the infeed is tangent to the top of the cylinder 9 (FIG. 7) to avoid bending and/or breaking the rigid plates. Likewise the grating 28 may be changed to provide a more suitable dimensional reference that may accomodate the new dimensions resulting from the 17.2% shrinkage that occured during sintering. A comparison of FIG. 7A and 7B or FIGS. 8A and 8B may be useful in understanding the significance of the 17.3% shrinkage; FIGS. 7A and 8A represent the size of unsintered workpieces 1 while FIGS. 7B and 8B are representative of the sintered ceramic. For illustrative purposes FIGS. 7A, 7B, 8A and 8B have all been drawn to the same scale. It may be noted that the circuit designers prefer the dimensions of the sintered sizes (FIGS. 7A, 8A) in making circuit layouts since it is the sintered size that is used to fit with other components of a larger assembly such as a computer. Thus, the designer's drawing may show the sintered size of a circuit pattern (FIGS. 7B, 8B) but the inspection tool may inspect the unsintered worksheets 1 (FIGS. 7A, 8A). As will be more fully understood hereinafter, it may be convenient for the inspection tool to use two different dimensional reference gratings 28; one grating based on an 0.005 inch X-Y design grid spacing for sintered ceramics and another grating based on an 0.006 inch X-Y grid spacing for unsintered worksheets. It should be noted however that either grating and/or grid spacing may be used interchangeably depending on which of the grid spacings is preferable for sintered and/or unsintered inspection by the inspection tool.

The Grating

In accordance with one feature of the invention, the grating 28 (FIGS. 1, 2) is used to provide a basic dimensional reference for the inspection tool. By controlled manipulation of the grating the X-coordinate dimensional reference may be proportionately contracted or expanded to correspond with the shrinkage or expansion of the dimensions of the worksheet 1.

To this end the grating alternately absorbs and transmits light energy to the photocell 32 as the reflected beam 25 sweeps the grating, the alternating presence and absence of light on the photocell creating a pulse form voltage output therefrom, the number of pulses of which providing a precise location of the beam 25 as it traverses the workpiece 1. Several types of gratings may be employed, in the preferred embodiment the grating includes a plurality of interdigitated or alternate opaque and transparent lines extending over a portion of a substrate, in the present instance a rectangle of transparent glass or other transparent material. An equivalent grating may include alternate non-reflecting and reflecting line surfaces extending over an area of a suitable supporting material such as a smoothly polished ceramic material. In this instance the photocell would be placed to receive the reflected light transmission.

As heretofore described, the partially reflecting mirror 27 (FIGS. 1, 2, 3) is used to divide the sweeping laser beam 25 into two synchronously moving beams with a major portion of the laser energy being focused on a workpiece 1. The partially reflecting mirror 27 thus reflects a portion 29 of the sweeping laser beam 25 as a focused laser spot to the grating 28. The spot may sweep across the grating in a straight sweepline 81–82 as shown in FIG. 18A, FIGS. 18B and 18C show portions of the grating 28 taken near the respective left and right sides of the grating. Opaque or non-reflecting grating lines 83 and transparent or reflecting lines 84 of the grating 28 are arranged preferably at a 45° angle to the sweepline 81–82 and laser spot 25. The alternating grating 83, 84 may be accurately formed across the grating 28 by photographic or other suitable means and preferably each line is 0.001 inches wide as measured diagonally along the scan line 81–82. Thus the actual width of the lines 83, 84 may be 0.001 inch × sin 45° as measured perpendicular to their 45° slope. The grating 28 is preferably about 7 inches wide in order to assist in the inspection of a 6 inches wide area of the worksheet(s) 1 as outlined by the dash lines 50 (FIGS. 4, 5 and 6). The above described arrangement may provide about 7000 grating lines across the grating 28 at 45° to the sweepline 81–82, with one half of the alternating lines 83, 84 absorbing energy from the sweeping laser spot and the other half of the lines being transparent for laser light transmission purposes. The light energy from a focused laser spot about 0.001 inch diameter may thus be alternately absorbed and transmitted by the 45° grating lines 83, 84 as the spot sweeps across the grating along the sweep line 81, 82. The light energy of the sweeping laser spot is essentially constant as the spot sweeps along the sweep line 81, 82 but the opaque or non-reflecting lines 83 dissipates this constant laser energy while the transparent or reflecting lines 84 allows transmission of laser energy in pulses. The pulses of transmitted laser energy may be focused by suitable optical means, for example, the lens 31 (FIGS. 1, 2) or a mirror (not shown) to the first photocell 32. The photocell 32 then provides electrical pulse signals corresponding to the laser pulse transmitting lines 84 of the grating 28.

Figure 18G:
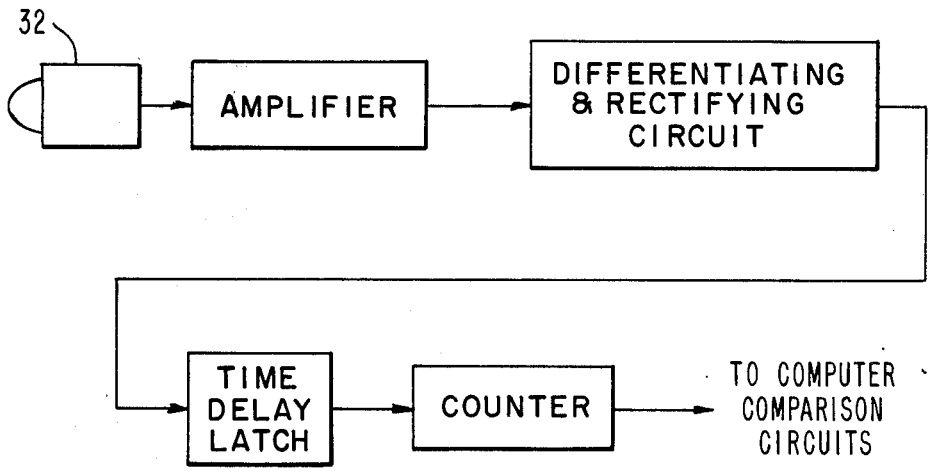
FIG. 18G is a schematic block diagram of the electrical circuitry employed to give a meaningful output from the photocell associated with the apparatus shown in FIG. 18A.
Figure 18A:
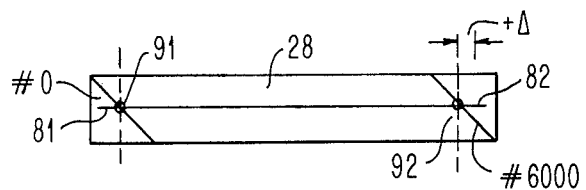
FIG. 18A is a schematic front elevational view of a portion of the apparatus illustrated in FIGS. 1-3, and showing the portion in a homo or rest position.

After suitable electrical amplification, and referring now to FIG. 18G, the output pulses from the first photocell 32 correspond to the upper portion of FIG. 18D where voltage V is the ordinate and the abcissa represents an X-coordinate corresponding to the traverse sweep of the laser spot 85 (FIG. 18B) along the sweep line 81–82. The voltage peaks 86 have broad tops and correspond to laser light transmission lines 84 of the grating 28. The valleys 87 have broad bottoms and correspond to no laser light transmission by the energy dissipating or opaque lines 83. The slope lines 88 between the peaks 86 and the valleys 87 are steep and correspond to a voltage transition as the laser spot 86 traverses the boundaries between energy absorbing lines 83 and energy transmitting lines 84, or vice-versa. By conventional differentiating circuit means (not shown) the amplified photocell signals, as shown in the upper portion of FIG. 18D, may be differentiated and rectified to appear as sharp peaks 89 as shown in the lower portion of FIG. 18D. Preferably the sharp peaks 89 may correspond in X-coordinate alignment with the steep slopes 88. In this manner the sharp peaks 89 provide accurate electrical marking signals as the sweeping laser spot 85 traverses the transition zones between the lines 83, 84 of the grating 28. Then by electrically counting the number sharp peaks 89 that may occur from a given X-coordinate starting point as the laser spot 85 sweeps across the grating 28 the momentary location of the sweeping laser spot 85 may be determined by the sum of the count. Since the transitions along the sweep line 81–82 for the grating lines 83, 84 occur every 0.001 inch the counting means provide location data from the laser spot at 0.001 inch intervals over a grating width of, for example, 6 or 7 inches. Thus for example, a count of 347 may be the equivalent of 3.474 inches from the starting point. Smaller intervals using interpolation means, described later, may be used for large and/or small measurements that may occur at and/or between the sharp peaks 89. An X-coordinate starting point for counting purposes may be provided on the grating 28 by omitting one or more energy absorbing lines 83 (FIG. 18E) and using a wide energy transmitting line 89 near the left margin of the grating. The photocell response to the wide energy transmitting line 89 is a broad voltage pulse 90 (FIG. 18F) that the electrical system may recognize as the starting point by its difference from the normal pulse 86. Electrically, a time delay latching circuit may be used to recognize the longer time duration of the broad pulse 90 with the latch initiating the counting circuit on the adjacent down-swing 88 of the photocell response. In summary, the grating and its sweeping laser spot may provide accurate X-coordinate data for the momentary location of the sweeping laser spot on the grating, and since the grating sweeping laser spot and the workpiece sweeping laser spot are synchronously aligned with each other, the X-coordinate data of the grating sweeping laser spot may be used to determine the momentary X-coordinate of the workpiece sweeping laser spot and thereby to obtain dimensional or positional data relative to the workpiece.

As has been described previously, circuit patterns on a worksheet 1 (FIGS. 4, 5, 6) that may nominally be 6.000 inches wide in the X-coordinate may vary up to about 0.001 inches at any of the 4 corners of the broken outline 50 (FIGS. 10 to 16) due to shrinkage or expansion and have proportionate displacements of the circuit patterns between such corners of the outline 50. In order to inspect a shrunk or expanded pattern the inspection tool may function initially to determine the width of the pattern by measuring a width between the left registration mark 45 and a right registration mark 49 and then function to adjust the inspecton tool's nominal measuring and/or inspection system to coincide and/or register with the shrunk or expanded circuit pattern dimensions. Means for initially determining the width of the pattern are described in later paragraphs.

Several approaches may be used for adapting the inspection tool's nominal measuring system to the shrunk or expanded worksheets. A complex approach is to take nominal counted X-coordinate dimensions from the laser sweep of the grating 28 and use a computer to multiply the nominal dimensions by the shrinkage or expansion ratios of each worksheet to obtain new X-coordinate dimensions. An example of this approach may illustrate the complexity: Assume that a nominal 6.000 inch dimension has been measured by the tool and found to be actually 5.9993 inches due to shrinkage; then each of the 6000 nominal X-coordinate points along the laser sweep line should be multiplied by the ratio 5.9993/6.000 to obtain new dimensions, which then requires "rounding out" to the nearest ⅛ mil or about 0.0001 inches. Since there are, in the present example, 6000 sweeplines for a 6.000 inch length of worksheet and a new worksheet is to be inspected every few seconds this requires 6000 × 6000 = 36,000,000 multiplications by the 5.993/6000 ratio and another ratio every few seconds. Such a multiplication effort requires a large and expensive computer.

A simpler and preferred approach to obtain new dimensions adapted for shrinkage or expansion is to provide the grating 28 (FIGS. 19, 20) with the equivalent of a pivot point 91 near the left side of the grating and then to suitable depress (FIG. 19) or elevate (FIG. 20) the right side of the grating to adapt the grating measurements to the shrunk or expanded dimensions of the workpiece(s) 1. In illustrating this approach, consider that in FIGS. 18A, 19, 20 only 2 of the 6000 or more actual grating lines on the grating 28 are shown: lines No. 0 and No. 6000. The sweepline 81-82 may intersect the No. 0 line at the pivot point 91 and the No. 6000 line at 92. Then with the grating 28 in the nominal position of FIG. 18A and the grating 28 the counting system may count 6000 indicating a nominal dimension of 6.000 inches between grating lines No. 0 and No. 6000 as previously described. In the nominal position of the grating 28 as shown in FIG. 18A the inspection tool uses the grating for accurate measurement purposes between the left and right registration marks 45, 49 of the worksheet(s) 1 (FIGS. 4, 5, 6). If while making such measurements a nominal dimension such as 6.000 inches is found to be actually 5.9993 inches due to shrinkage, the grating 28 is rotated downward about the pivot point 91 (FIG. 19) whereby the new intersection 93 of scan line 81-82 with the grating line No. 6000 is now approximately 0.0007 inches higher (to the left and above) than the previous intersection 92. Since the grating lines are at 45° (FIG. 18B) to the scan line 81-82 this 0.0007 inch higher intersection point 93 also results in the intersection point 93 being moved substantially an equal 0.0007 inch distance to the left (tan 45° = 1.0000). Thus the nominal dimension of 6.000 inches between points 91, 92 (FIG. 18A) is foreshortened by 0.0007 inches thereby becoming 5.9993 inches between points 91, 93 in FIG. 19. The sweeping laser spot 85 (FIG. 18B) traversing the grating 28 (FIG. 19) now results in a count of 6000 X-coordinate points between locations 91 and 93 with all X-coordinate point dimensions reduced proportionally by the ratio 5.9993/6.000 to match the shrinkage of the workpiece 1. This is without the complex computer ratio calculations required above.

Figure 20:
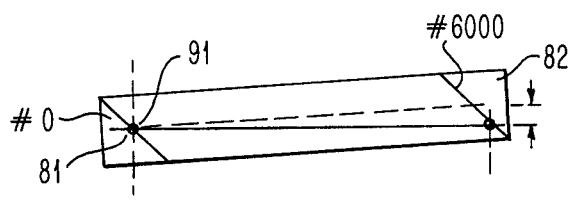

FIG. 20 illustrates a similar procedure wherein the nominal grating of FIG. 12A and point 92 may be rotated upward about the pivot point 91 to provide an increased dimension between the scan line 81-82 interceptions 91, 94 with the grating lines No. 0 and No. 6000, and thereby match an expansion of the workpiece 1. In summary, the sweeping laser spot and the nominal position of the grating provide a basic dimensional reference scale for accurate measurement of work sheet dimensions and pattern position and if such work sheet dimensions deviate from nominal dimensions the effective scale may then be shrunk or expanded to match such work sheet deviation dimensions by a suitable rotation of the grating about a pivot point.

The above described ability of the sweeping laser spot and the grating to shrink or expand the inspection tool's measuring scale is also useful in inspecting workpieces after stacking and laminating. As heretofore described the green sheet, during sintering incurs a 17.2% dimensional shrinkage. For subsequent assembly purposes and the conveniences of the circuit designer, the sintered dimensions are considered to be the basic dimensions and the drawings of individual workpieces show these sintered dimensions. Additionally, the basic sintered dimensions (FIGS. 7B, 8B) may be designed to a basic 0.005 inch X-Y grid matrix 95, 96 having X-Y sub-grids of 0.0005 inches. The basic matrix allows the via holes and 0.005 inch wide circuit pattern lines to be centered on basic grid lines and the edges of circuit pattern lines to be on the sub-grid matrix lines. The circuit pattern, as is conventional in the industry may be designed by a suitably programmed computer wherein electrical circuit data is fed to the computer and a computer controlled drafting machine then make a large scale drawing of the circuit pattern. A data image of the circuit pattern may be retained by the computer memory bank, magnetic discs. However for unsintered worksheet inspection purposes the basic sintered dimensions may be expanded to compensate for sintering shrinkage and the worksheet then inspected to the actual unsintered dimensions. If for example the sintering shrinkage were found to be 17.2% then the basic sintered dimensions may be 100% − 17.2% = 82.8% of the linear length of the workpieces inspection dimensions. Thus if the data image width of a sintered circuit pattern were to be retained in the computer memory bank as 5.000 inches then the worksheet inspection dimension for this width would be 5.000/0.828 = 6.0386 inches. Since this 6.0386 inch dimension is so close to an even 6.000 inch dimension the nominal grating of FIG. 18A may be rotated about the pivot point 91 to elevate the 6000th grating line by 6.0386 − 6.0000 = 0.0386 inches as in FIG. 20. This large or gross adjustment may provide a new inspection scale of 6000 X-coordinate inspection points covering the full 6.0386 inch width of the workpiece. There may now be a simple ratio of 6000/5000 = 1.2 to the sintered design dimensions retained by the computer memory bank. The computer may then multiply its retained data image of a circuit pattern by 1.2 to obtain expanded X-coordinates for worksheet inspection purposes. This arrangement has a further advantage in that the basic 0.005 inch X-Y grid matrix used for sintered design purposes may now become a 1.2 × 0.005 = 0.006 inch X-Y grid matrix 97, 98 for inspection purposes shown in FIGS. 7A, 8A. The centers of via holes and the center lines of circuit lines may then be conveniently on 0.006 inch matrix grid lines with the edges of circuit lines aligning with 0.001 inch sub-grid lines.

It should be understood that the dimensions of the workpiece being inspected by this procedure have not been changed but only that the rotation of the grating has provided a suitably expanded measuring scale that may now allow the use of the convenient 0.006 inch X-Y matrix grid. The expansion of the measuring scale in the example was in effect by the ratio of 6.0386/6.000 = 1.00644. Then with the computer expanding a 5.000 inch wide sintered pattern by a factor of 1.2: 5.000 × 1.2 × 1.600644 = 6.0386 inches wide for unsintered workpiece inspection. Additionally, small adjustments of the grating may be used to compensate for up to ± 0.001 inch variations of worksheet pattern widths as previously described.

Figure 21:
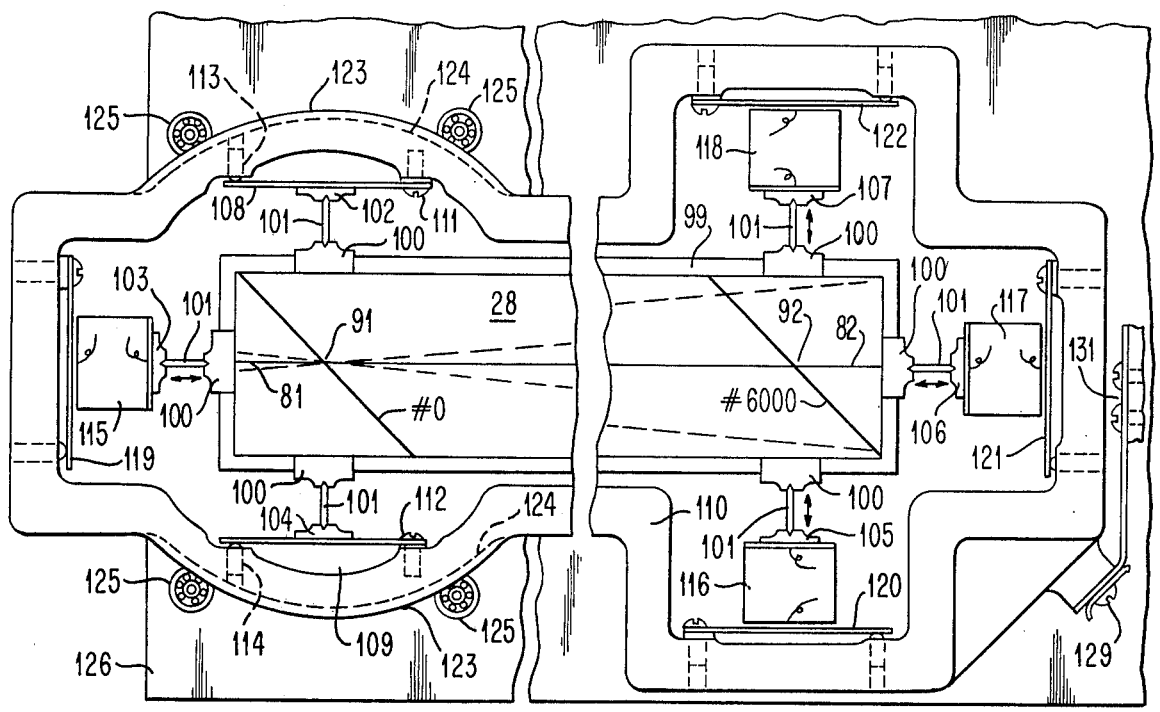
FIG. 21 shows the apparatus of FIGS. 18-20 with a frame and associated vernier means for altering the position of the apparatus.

FIG. 21 shows the grating 28 together with associated structural and actuating components. The grating 28 may be retained in a light or low mass sub-frame 99. In the illustrated instance several small pivot blocks 100 are spaced about and attached to the sub-frame 99 at suitable locations for coaction with knife edge pivots. One end of knife edge pivot blades or links 101 engage the pivot blocks 100 and the other end of the knife edge pivot blades 101 engage suitably located pivot blocks 102, 103, 104, 105, 106, 107 as shown. As shown, the pivot blocks 102, 104, are attached to spring elements 108, 109 which are fastened to a rotating frame 110 with fastening screws 111, 112 and the other end of the spring elements 108, 109 contact adjustable set secrews 113, 114 in the frame 110. The pivot blocks 103, 105, 106 and 107 are attached respectively to grating actuator means 115, 116, 117, 118. The actuator means may be various types of components that produce physical motion or displacements responsive to electrical, hydraulic, air pressure, etc. signal commands. Among such components responsive to electrical signal commands may be piezo-electrical devices, magnetostrictive elements, solenoids, etc. However, for this Application the actuators 115, 116, 117, 118 are preferably piezo-electrical devices because of their relatively fast motion response to command signals and low power consumption. As illustrated, the actuators 115, 116, 117, 118 are fastened to springs 119, 120, 121, 122 respectively with these springs being fastened and adjustable to the grating rotating frame 110 is a manner similar to the springs 108, 109 by using fastening screws and adjustable set screws. The springs are used to maintain compression forces on the knife edge pivot blades or links 101 and thereby avoid backlash or lost motion. The adjustable set screws provide small displacements for the springs and may be used for initial grating adjustments and calibration purposes.

As has previously been described relative to FIGS. 18A-18E, the sweeping laser spot traverses the grating 28 along the sweepline 81-82, of the 6000 or more alternating opaque and transparent grating lines positioned at 45° to the sweepline 81-82, only line 0 and line "6000" are shown in FIG. 21, it being understood that there may be grating lines to the left of 0 and to the right of the "6000" grating line. As shown, the line 0 intersects the sweepline 81-82 at a point 91. The knife edge pivot blades or links 101 associated with pivot blocks 102, 103, 104 near the left end of the grating are used, in the present instance, to effect a pivot point located at 91 for small rotary motions of the grating in the vertical plane. The small rotary motions may be applied to the grating by the actuators 118, 116 located above and below the intersection 92 of the scan line 81-82 with the No. 6000 grating line near the right end of the grating. As described previously relative to FIGS. 18A, 18E, 19, 20 a ± 0.002 inch vertical motion at the right of the grating has a net effect of ± 0.002 inches in the distance between the intersection points 91 and 92 with the laser scan line 81-82 since the scan line remains in a fixed spatial position while the grating moves and pivots about the points 91.

Figure 19:
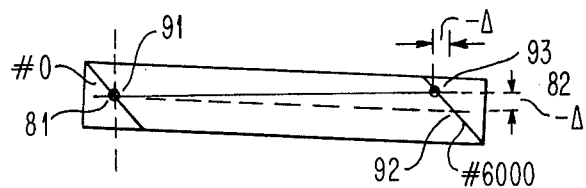
FIGS. 19 and 20 illustrate the portion of the apparatus illustrated in FIG. 18A in alternate positions.

The grating 28 of FIGS. 18A, 19 and 20 includes means whereby the grating may be physically moved to the left or to the right by approximately ± 0.001 inch. This physical movement of the grating then allows the X-coordinate measuring points of the grating, such as the sharp peaks 89 of FIG. 18D, to be aligned or registered to the workpiece pattern that is to be inspected, or for initial machine to optics and workpiece registration. To this end, the grating may be physically moved horizontally to the left or right by actuators 115, 117 which thereby provide improved alignment or registration between the grating 28 and the workpiece 1 to be inspected.

The entire grating rotating frame 110 and components attached thereto may also be rotated about the pivot point 91 to obtain larger rotary movements of the grating 28 then may be obtained from actuators 118, 116. To this end, to obtain such larger rotary movements the left portion of the rotating frame 110 includes machined arcs 123 and grooves 124 to form an arcuate track having a center on the pivot point 91. Ball bearings 125 or the like engage the arcuate grooves 124 to position the rotary frame 110 and permit rotary movement thereof. The bearings 125 are supported by a main frame plate 126 that includes a large aperture (not shown) substantially coextensive with the grating and includes means therein supporting the second lens 31 of FIGS. 1, 2. The larger rotary movements of grating rotating frame 110 may be obtained by vertical movements of a spring link member 128 attached thereto by a fastener 129 at the lower end of spring. The upper end of the spring may be attached to one half of a spring loaded lead screws nut 130 by a fastener 131 as may be seen more clearly in FIG. 22.

Figure 22:
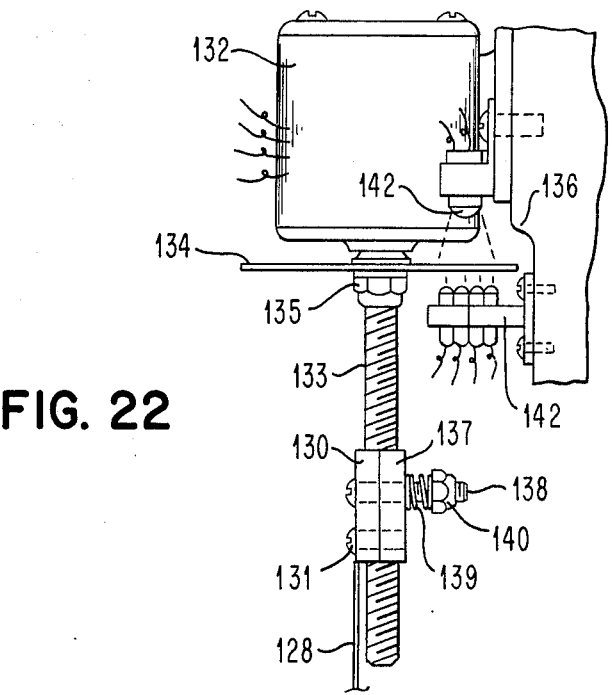
FIG. 22 is an enlarged fragmentary schematic view of means for grossly altering the slope of the frame and apparatus shown in FIG. 21.

The actuating means for obtaining large rotary movements of the grating rotary frame 110 (FIG. 21) may be seen in FIG. 22. A small stepping-type motor 132 rotates a lead screw 133 and an encoding disk 134 attached thereto by a nut 135. As shown, the stepping motor 132 is supported by an extension 136 of the main frame plate 126 (FIG. 21). The rotation of the lead screw 133 moves a spring-compressed split nut 130, 137 vertically upwards or downwards thereby moving spring 128 attached thereto. A pair of screws 138 straddle the lead screw 133 and extend through the split nuts 130, 137 to compression springs 139 and adjustable nuts 140 whereby an adjustable compression force may be applied to the split nuts to reduce backlash. A light source may be arranged to project light through the encoding disk 134 to multiple photocells 142 whereby the rotational position of the motor 132 is known and its rotation controlled to start at a predetermined position. The motor encoding disc, light source and photocells are available commercially and an equivalent magnetically controlled package may be substituted therefore. The arrangement described relative to FIG. 22 enables an inspection tool operator or a computer to make large or gross rotations of the grating 28 of FIG. 21 to a desired position corresponding to an average or nominal shrinkage factor of the workpiece 1; the actuators 118, 116 may then adjust the grating to the shrinkage or expansion of an individual workpiece 1.

The Flexible Prism

The elongated flexible prism 33 of FIGS. 1, 2, 3 may be used to provide Y-coordinate adjustments for the laser beam 25 as the beam sweeps along an X-coordinate line on the workpiece 1 by refracting the beam 25. The Y-coordinate adjustments assist in the alignment and/or registration of the sweeping laser beam 25 to the workpiece 1 being inspected. To this end FIGS. 23-28 illustrate functions of the flexible prism 33, the prism 33 being composed preferably of optically transparent semiflexible plastic material such as polyvinyl chloride or the like and positioned to overlie the work zone adjacent the workpiece. In FIG. 23 the laser beam 25 is shown being swept through sweep angle 24–26 passing through the nominal position of the prism 33 and intercepting the workpiece 1 along an X-coordinate nominal line 143–144. In FIG. 24 it may be observed that the top and bottom surfaces of the prism 33 are parallel to each other and in this nominal position are also perpendicular to the plane of the sweep 24–26 of the sweeping laser beam 25, and therefore the beam 25 passes through the prism without deflection in the Y-coordinate. However, by suitable means to be described later the prism 33 may be rotated clockwise or counterclockwise abouts its long axis 145–146. A counterclockwise rotation from the nominal position is illustrated in FIGS. 26 and 27 wherein the laser sweep plane 24–26 that enters into the rotated prism 33 emerges from the rotated prism as sweep plane 147–149 with both sweep planes deviating from the perpendicular angle of FIGS. 23 and 24 by entrance and exit angles equal to the angular rotation of the prism. The optical properties of the rotated prism 33 may be such that the emerging laser sweep plane 147–149 provides a beam 148 which may be parallel to the entering sweep plane 24–26 but separated therefrom by a small Y-coordinate dimension $-\Delta Y$, the beam 148 intercepting the worksheet 1 along a new sweep line 150–151. Similarly a clockwise rotation of the prism 33 as shown in FIG. 25 may provide another sweep line on the worksheet 1 that is parallel to the nominal sweep line 143–144 but separated therefrom by the dimension $+\Delta Y$. For small rotational angles of the prism 33 the Y-coordinate displacement dimensions $-\Delta Y$ and/or $+\Delta Y$ may be considered to be proportionate to the angle of rotation of the prism. Thus in conjunction with suitable sensing and control means as described hereinafter by small rotations of the prism 33 the nominal scan line 143–144 may be deflected to align or register with the X-coordinate positions of the X-coordinate lines on a workpiece 1 that may have become displaced from nominal positions as previously described relative to FIGS. 11, 12 and 13.

The flexible material of the prism 33 may permit the prism to be twisted about its long axis 145–146 as shown in FIG. 28 and/or rotated about its long axis as shown in FIG. 27. Such twisting may be accomplished, for example, by rotating the right end of the prism 33 counterclockwise and the opposite or left end of the prism clockwise as shown in FIG. 28. The emerging sweep plane 152–154 of the beam 153 from the twisted prism 33 may be skewed (not parallel to the entering sweep plane 24–26 and the skewed sweep plane may now intercept the workpiece(s) 1 along a skewed sweep line 155–156. In FIG. 28 the nominal sweep line 143–144 is shown as a dashed line for reference purposes. The Y-coordinate displacement of the intercept between sweep line ends 144 and 156 at the right is shown as $-\Delta Y$ and at the left between 143 and 155 as $+\Delta Y$. It may be understood that the Y-coordinate displacement at either end of the skewed sweep line 155–156 may be anywhere between $-\Delta Y$ and $+\Delta Y$ depending on the direction and degree of rotation applied to the opposite ends of the flexible prism 33. It may be further understood that there may be other similar Y-coordinate displacement functions that may result from the individual and/or combined functions described relative To FIGS. 23 to 28. Thus the axial twisting of the flexible prism 33 may assist in the alignment and/or registration of the sweeping laser spot to the skewed horizontal outline lines of FIGS. 14, 15, 16 previously described.

Figure 29:
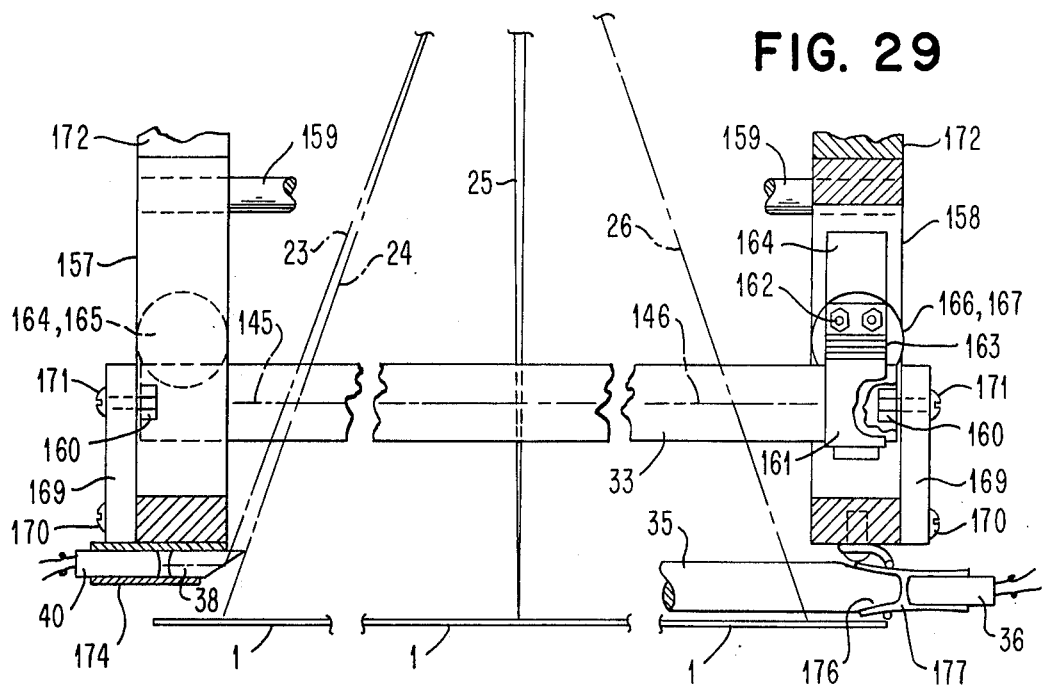
FIG. 29 is a fragmentary schematic view showing means that may be employed for gross adjustments and alignment of the Y inspection coordinates.
Figure 29A:
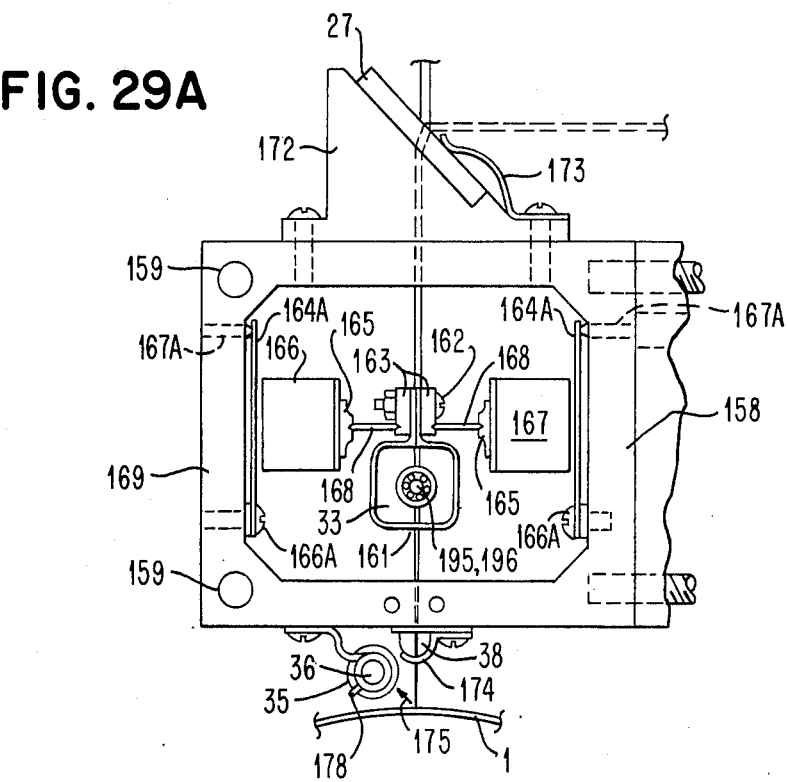
FIG. 29A is an end view of the apparatus shown in FIG. 29.

The flexible prism 33 including various associated structural components and actuators may be in a nominal position as shown in FIGS. 29, 29A. As shown, the long axis 145, 146 of the prism 33 is in the plane 23, 24 and 26 of the sweeping laser beam 25 as shown in FIGS. 3, 23 and 29. A left frame member 157 and a right frame member 158 support components associated with the left and right ends of the prism 33. Tie rods 159 may hold the frame members 157, 158 together for initial sub-assembly purposes. Actuation components as hereinafter described are symmetrical left and right as associated with frame members 157, 158. The prism 33 is mounted for rotation between the frame members by small ball bearings 160 which may be located within the ends of the prism 33.

In order to effect rotation of the prism 33, band clamps 161 are connected to the ends of the prism 33 by clamp screws 162 and pivot blocks 163. As shown, left actuator means 164, 165 and right actuator means 166, 167 each have one end fastened to adjustment springs 164A and the other end fastened to pivot blocks 165A. The bottom ends of the adjustment springs 164A are fastened to the frame members 157 and 158 respectively by fasteners 166A. The top ends of the adjustment springs 164A contact adjustable set screws 167A in the frame members 157, 158 for adjustment and/or alignment purposes. By using an assembly fixture (not shown) to support the prism 33, knife edge pivot blades 168 may be interposed between the pivot blocks 163 and the pivot blocks 165 to provide actuation linkage. Shaft support members 169 may then be assembled to the frame members 157, 158 using screws 170, and stub shaft screws 171 may be run through the support members and into the shaft diameters holes of the bail bearings 60. After removal of the assembly fixture (not shown) the above described actuators and structural elements may be employed to provide independent rotations to the left and/or right ends of the flexible prism 33. The actuators 164, 165, 166, 167 are preferably be of an equal displacement push-pull type: for example in FIG. 29A, when actuated by a right command and actuator 166 pushes its associated pivot blocks 165, 163 and blade 168 to the right and the opposite acuator 167 pulls (retracts) by an equal displacement to the right thereby allowing its associated pivot blocks 165, 163 and blade 168 to move to the right. When activated by a left command a similar actuation occurs except that the displacements is to the left. Meanwhile, opposite springs 164 maintain the above described actuation system in compression by applying thrust forces from opposite sides of the right frame member 158. Thus the pivot blocks 163 may be actuated to move right or left thereby providing clockwise or counter clockwise rotation about the ball bearing 160 for the clamp 161 and the right end of the flexible prism 33. Similar actuation components within the left frame member 157 (FIG. 19) provide similar rotations for the left end of the flexible prism 33. In summary, it may be understood that with duplicate actuation systems at each end of the flexible prism 33, each end of the prism may be rotated independently of the opposite end, thus the angle of rotation and the X-coordinate deflection of the sweeping laser beam 25 may be proportional and responsive to proportional actuation commands.

The structure shown in FIGS. 29, 29A may also be used to support other components of the inspection tool. As shown, the partially reflecting mirror 27 (FIGS. 1, 2, 3), that reflects a portion of the scanning laser beam 25 to the grating 28, may be supported by brackets 172 secured to the left and right frame members 157, 158. The partially reflecting mirror 27 may be retained by spring clips 173 to provide easy removal for cleaning purposes. The underside of the left frame member 157 supports the reflecting mirror prism 38 and the light detector or photocell 40 (FIG. 3) that provide a margin delineation as at 23 and 24 for the sweeping laser beam 25. The mirror prism 38 and the photocell 40 may be retained together in a holder 174 that may be positionally adjustable left and right and secured to the frame member 157. The undersides of the left and right frame members 157, 158 may support the left and right ends of the transparent light conductor rod 35 and photocells 36 (FIG. 1) located at each end of the rod whereby diffused reflected light indicated by the arrow 175 from the sweeping laser beam 25 may be captured by the rod as the beam sweeps across the workpiece 1 and the captured light converted into electrical signals by the photocells. The portions of the rod 35 adjacent the ends may be formed to an exponential curve 176 of progressively decreasing diameters to reflect captured laser light to the photocell 36. Sleeves 177 at each end of the end 35 are provided to hold the photocells 36 adjacent the ends of the rod 33. Spring wire clips 178 that snap over the sleeves 177 are attached to the frame members 157, 158 and provide easy removal for cleaning of the rod 35, the sleeves 177 and the photocells 36.

In order to compensate for misalignment, for example, skew in the workpiece, and as explained more fully hereinafter, the first few sweeps of the laser beam determine the position of the registration marks relative to the beam sweep, the response being detected by the photocell 36. If misaligned, then by either manual readout by the machine operator, or computer calculation in conventional comparison circuits, the actuators 164, 165 and/or 166, 167 may be energized to effect twist of the prism or angular rotation thereof to effect registration of the sweep with the alignment marks.

The Drive Scheme

Figure 30:
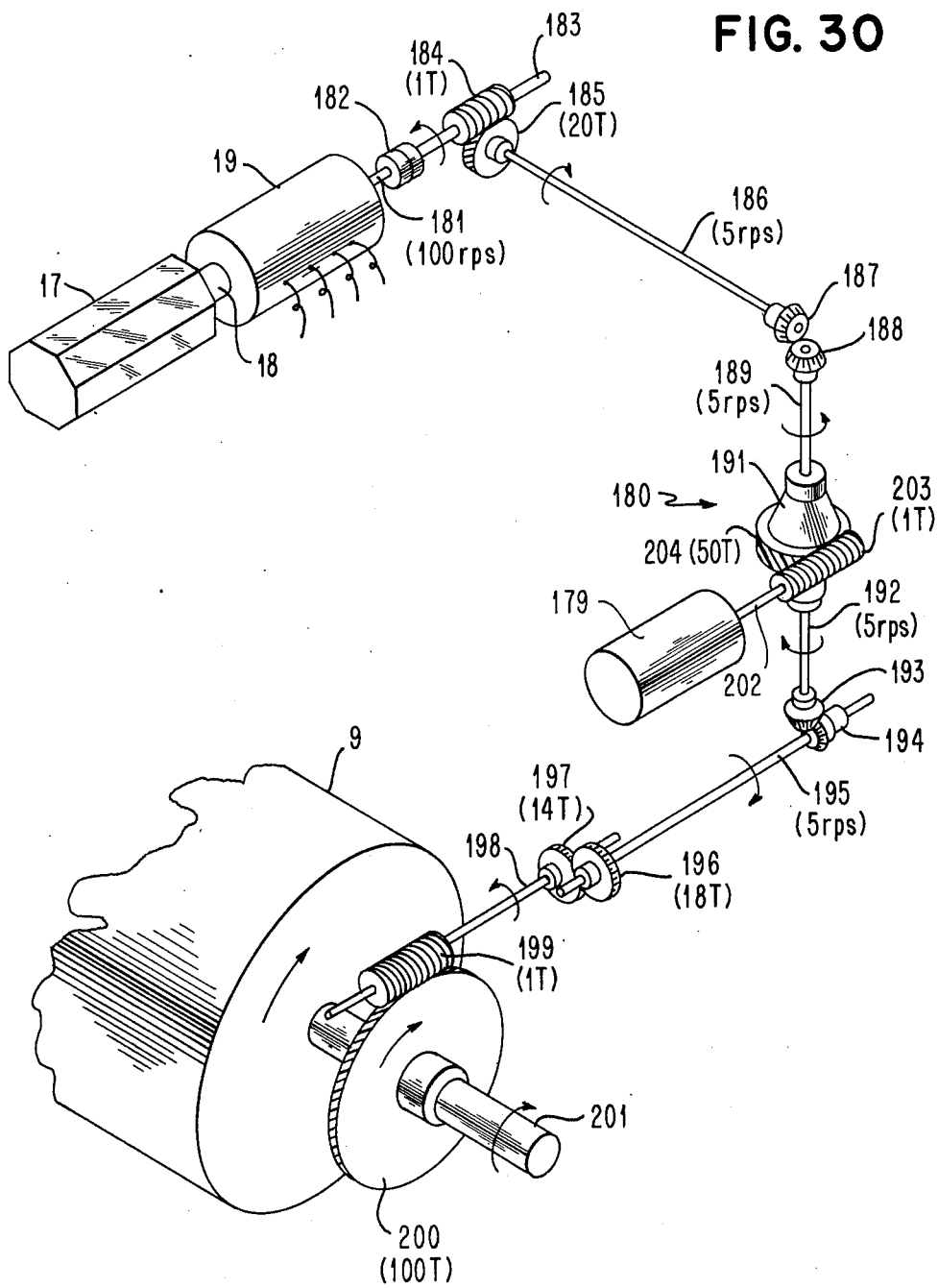
FIG. 30 is a fragmentary perspective view illustrating electro-mechanical means that provide vernier drive for the scanning laser and workpiece feed.

In order to sweep of the beam 25 with the movement of a workpiece it is necessary to provide means to synchronize the beam sweep with workpiece movement. To this end a gear drive train, such as is shown in FIG. 30, may be driven by the first motor 19 (FIG. 1) to effect rotation of the cylinder 9 and to provide an adjustable rotational drive ratio between a high speed motor rotation and a low speed cylinder rotation. The adjustable drive ratio may be provided by adjusting the speed and/or direction of rotation of a second motor 179 and an associated differential gear system 180. Thus a small rotational speed adjustments may be added to or subtracted from the rotational speed and a surface velocity of the cylinder 9 relative to a fixed rotational speed provided by the fixed gear drive train ratio. For illustrative purposes in FIG. 30 the directions of shaft rotations may be indicated by curved arrows and the speeds of shaft rotations in revolutions per second (rps) may appear below their description numbers. Likewise the numbers of teeth in the gears and/or the threads, in the worm screws may appear below their description numbers. However it may be understood that there may be many other combinations of motor speeds, shaft speeds, and numbers of motor speeds, shaft speeds, and numbers of gear teeth that may be used to provide equivalent and/or different overall gearing ratios for the gear drive train. The motor shaft 18 that rotates the multifacet mirror 17 may extend through the first motor 19 as smaller shaft 181. A vibration isolation coupling 182 connects the motor shaft 18 to a worm shaft 183 and a single thread worm 184. The worm 184 effects rotation of a worm gear 185, horizontal shaft 186, and a first miter gear 187 of a pair of 1:1 ratio miter gears. The second miter gear 188 is connected to shaft 189 and an upper miter gear within the differential gear system 180. In accordance with well known operating principles of differential gear systems (such as in an automobile differential gear system), the rotation of the upper miter gear in one direction causes rotation of a lower miter gear (not shown) in an opposite and/or reverse direction through rotation of an intermediate miter gear (not shown). The intermediate miter gear rotates on a shaft secured to the housing 191 of the differential gear system 180, while the lower miter gear rotating in the opposite direction, is coupled to and effects rotation of a lower shaft 192. The lower vertical shaft thus rotates a second pair of 1:1 ratio miter gears 193, 194, a horizontal shaft 195, and a gear 196. The gear 196 rotates another gear 197, worm shaft 198 and a single thread worm 199. The worm 199 effects rotation of a worm gear 200, cylinder shaft 201, and the cylinder 9.

The above described gear drive train may be employed to provide a fixed drive ratio and rotational speed of the cylinder 9 assuming that the second motor 179 and the differential housing 191 are not rotating. However, if small plus or minus variations from the fixed drive ratio are required by the inspection tool, and/or by the computer, and/or by the operator such variations may be applied to the gear drive train by energization of the second motor 179. The motor 179 then effects rotation of a worm shaft 202 and a single threaded worm 203. The worm 203 rotates a worm gear 204 attached to the differential gear system housing so that if the differential housing 191 is rotated at, for example, 1 revolution per second in a given direction the rotational rate of the lower vertical shaft 192 may be varied by 2 revolutions per second in the same given direction. This varied speed may additive to or subtractive from the fixed rotational speed of the shaft 192 depending on the direction of rotation of the second motor 179.

The variable speed motor 179 may preferably be of a two phase stepping motor type whereby its rotational direction and speed may be readily controlled by a fixed and/or variable stepping periodicity of an associated two phase power supply (not shown).

The variable speed second motor 179 may be employed to make larger Y-coordinate dimensional adjustments on the workpiece 1 relative to the sweeping laser beam spot than the smaller adjustments that may be readily accomplished by the flexible prism 33. (FIGS. 29, 29A). Such larger and smaller adjustments in the Y-coordinate may be similar in effect to the larger and smaller X-coordinate adjustments provided by rotating the grating 28 (FIGS. 21, 22). An extension of the previously used X-coordinate example into the Y-coordinate may be useful in describing the utility of such larger adjustments. As previously described, the circuit pattern design of a workpiece 1 may be made to sintered dimensions where as the workpiece may be inspected to larger unsintered dimensions, i.e., dimensions prior to sintering shrinkage. Thus the design data may show a 5 inch square circuit pattern and the inspection tool may inspect the Y-coordinate unsintered dimensions as 5.000/.828 = 6.0386 inches. The sintering factor 0.828 or other factors may be used to account for the sintering shrinkage and may be applied to sintered X and/or Y-coordinate circuit pattern dimension within pattern outline 50 to thereby obtain unsintered inspection dimensions. Thus with an effective diameter of 0.001 inch for the sweeping laser spot, 1000 sweep lines per inch may be used in the Y-coordinate. Cooorespondingly the 6.0386 unsintered dimensions of the workpiece may require 6039 sweep lines to be applied by the inspection tool. However since 6039 as a number is so close to the number 6000 it may be more convenient and save computer time to use 6000 scan lines to inspect the workpiece 1. The convenience may be that the design data for the sintered workpiece 1 is based (in the example) on a 0.005 inch X-Y matrix grid system including a 0.005 inch sub-grid. In using the grid system it may be convenient for a circuit designer to locate via hole centers at matrix 0.005 inch grid intersections and the centers of 0.005 inch wide conductor lines on grid lines (see FIGS. 7B, 8B). The edges of a 0.005 inch wide circuit line may be located 0.0025 inches either side of a grid line and thereby coincide with a sub-grid line. Then when the design data (sintered dimensions) is expanded for inspection purposes (unsintered dimensions) the design data may be multiplied by a factor of $1.2 \times 10^3$ whereby a 5.000 inch Y-coordinate dimension, $5.000 \times 1.2 \times 10^3 = 6000$ sweep lines. Similarly for the 0.005 inch matrix grid and circuit conductor lines, $0.005 \times 1.2 \times 10^3 = 6$ sweep lines. Thus this procedure produces an inspection matrix grid based on an even 6 sweep lines with the centers of via holes and conductor lines coinciding with the matrix grid (see FIGS. 7A, 8A). Likewise the edges of circuit conductor lines may now be $0.0025 \times 1.2 \times 10^3 = 3$ sweep lines from the matrix grid lines. However, since the Y-coordinate unsintered dimension to be inspected may be 6.0386 inches, means may be provided to spread 6000 scan lines over 6.0386 inches. Such means may be provided by the variable speed motor 179 (FIG. 30) and the differential gear system 180 whereby the rotational speed of the cylinder 9, as driven by the fixed gear ratio components of the gear train, may be increased slightly to spread 6000 sweep lines over 6.0386 inches. Since a fixed gear ratio may be designed for 6000 scan lines over a 6.000 inch Y-coordinate dimension the increase in rotational speed of the cylinder 9, in the example given, would be in the ratio of 6.0386/6.000 = 1.0064333 or about a 0.6433% speed increase.

Various approaches may be used in the design of the drive gear train FIG. 30 and/or its equivalent. Assuming initially (subject to later correction) that the workpiece (1) (FIGS. 4, 5, 6) to be inspected within the outline 50 may have dimensions of 6.000 inches by 6.000 inches, the outline 50 is centered in a 7.000 by 7.000 inch area of workpiece material to provide 0.500 inch margins outside of the outline 50. Assuming a drive motor 19 (FIG. 30) rotation of 100 revolutions per sec (rps) while driving the 18 facet mirror 17 and the single thread worm 184, the laser beam 25 sweep in lines per second may be calculated, i.e., $100 \times 18 = 1800$ lines per second. The circumference of the cylinder 9, allowing for ½ the thickness of the workpiece, may be equal to the length of 4 pieces of worksheet material, i.e., $4 \times 7.000 = 28.000$ inches. The rotational speed of the cylinder 9 may then be calculated, 1800/28,000 = 0.0642871 revolutions per second (rps). This corresponds to 15.5555 seconds for one revolution of the cylinder 9 with four workpieces or slightly under four seconds to inspect one workpiece. With the prior motor 19 and the worm 184 rotating at 100 rps, the driving gear ratio is then calculated for the cylinder, 100/0.0642871 = 1,555.55 gear ratio. With this ratio in mind, the single thread worm rotates the 20 tooth worm gear 185, and shafts 186, 189, 192 and 195 at 100/20 = 5 rps. The 18 tooth gear 196 rotates the 14 tooth gear 197 and the worm shaft 198 at $5 \times 18/14 = 6.428571$ rps. The single thread worm 199 rotates the 100 tooth worm gear 200, the cylinder shaft 201 and the cylinder worm gear 9 at, 6.428571/100 = 0.06428571 rps as previously calculated to be the assumed speed. However, the assumed cylinder speed may now be corrected to spread 6000 sweep lines over 6.0386 inches by using the previously calculated speed increase ratio 1.006433 which may be applied to the drive gear train through the functioning of the differential gear system 180.

With the upper vertical shaft 189 continuing to rotate at 5 rps. the speed of the lower vertical shaft 192 may be increased from 5 rps. to $5 \times 1.006433 = 5.032165$ rps. by rotating the differential housing 191 at ½ of the differential speeds between the shafts 189, 192. Thus the rotational speed of the housing 191 may be determined, $5.032165 - 5. = 0.032165$ rps, and divided by 2 = 0.0160825 rps. As described, the housing 191 is rotated by a 50 tooth worm gear 204 and a single thread worm 203 having a gear ratio of 50 whereby the speed of the worm shaft 202 and the second motor 179 $0.0160825 \times 50 = 0.804125$ rps.

The second motor 179 and its two phase power supply may be commercially available types providing 180 step positions per one rotation of the motor driven worm shaft 202. A stepping motor of this type rotates its rotor and shaft through an angle of $360°/180 = 2°$ per step. As an example of the type of stepping motor, it may have two types of electrically isolated pole windings, each on separate poles: a first phase winding and a second phase winding. The power supply, in that case, is arranged to provide suitably phased voltages to the first and second phase windings whereby the motor shaft rotated one step at a time.

One of the characteristics of a stepping motor is that the rotor of the motor may remain in a fixed positional alignment with a pole (or groups or similarly magnetized poles) for as long as a suitably polarized and phased first or second phase voltage is applied to the polar coil windings of the motor. Then for example, if a first phase voltage that is holding the rotor in a fixed rotational alignment is shut off and 8 suitably polarized second phase voltage is turned on, the rotor may make one rotational step of 2° and remain there until the second phase voltage is shut off. Then by turning on a reverse polarized first phase voltage another 2° step may be taken in the same rotational direction, etc. Thus the rotor may stepped through 2° and stopped 180 times in for one 360° rotation of the worm shaft 202. The time interval between the 2° steps is controlled by suitable timing and phasing of the two phase power supply whereby the rotational speed of the motor's rotor and the worm shaft 202 are controlled. The power supply may include well known means to convert 117 volt 60 cycle single phase commercial power into suitably phased lower voltage power for the stepping motor 179. A short timing signal pulse from an external signal source may provide the timing control for the power supply whereby the motor's rotor then takes single 2° steps. For example, a positive signal pulse may provide a 2° clockwise step or a negative signal phase may provide a 2° counter clockwise step.

Various means may be used for generating timing signal pulses to control the rotational speed of the stepping motor 179 and the worm shaft 202. Preferably the pulse generating means is flexible so that the timing between pulses may be varied to control the speed of the stepping motor and thereby to provide for various anticipated sintering shrinkages of the workpiece 1. At the previously calculated speed of 0.804125 rps. for the stepping motor 179, the motor requires $0.804125 \times 180 = 144.7425$ steps per second at 2° per step. A high frequency clock or its equivalent provides high frequency pulses which may be applied to a high frequency pulse counter. The pulse counter may count the high frequency pulses and at repeating and predetermined pulse counts issue lower frequency pulses to control the two phase power supply and the stepping motor 175. The photocell 40 (FIGS. 3, 29) may be used to generate a single high frequency pulse from each sweep of the sweeping laser beam 25, and thus may be considered the equivalent of a high frequency clock. Since in the example given there were 1800 laser beam sweeps per second the photocell 40 generates 1800 pulses per second. If the stepping motor requires 44.7425 stepping pulses per second, as previously calculated, the predetermined pulse count number may thus be calculated, $1800/44.7425 = 40.230206$ high frequency counts per stepping motor pulse. Since this high frequency count number is not an integer number two or more counters may be required to approximately simulate the number: let the first counter count up to a next higher integer number such as 41, thus $1800/41 = 43.9024$ and subtracting, $44.7425 - 43.9024 = 0.8401$. Next, $1800/18401 = 2,142$ and use a next higher integer 2143 for the second counter to issue respective supplemental stepping motor pulses. Then the stepping motor pulse rates from the first and second counters may be added:

1st: $1800/41 = 43.9024$ stepping motor pulses per sec
2nd: $1800/2143 = 0.0399$ stepping motor pulses per sec
1st + 2nd counters = 44.7423 stepping motor pulses per sec This number may approximately simulate the required number of 44.7425 stepping pulses per second for practical purposes when the flexible prism 33 of FIGS. 23–29 deflects the sweep line 143, 144 of the laser beam to provide a dimensional equivalent for the difference between the two pulse rate numbers. It may be noted that by continuously providing electrical power to the counters, the stepping motor power supply, and the laser beam the stepping motor 175 remains in a functional type of "step synchronism" with the mirror drive motor 19 during periods when the motor 19 may be decelerated to a stop, during a stop, and accelerated from a stop to a constant and/or variable running speed. Thus the "step synchronism" speed ratio between the mirror drive motor 19 and the stepping motor 175 remains fixed by the high frequency counting numbers previously set into the counters. The "step synchronism" speed ratio may also be changed by having the inspection tool operator and/or the computer set suitable new numbers into the counters whereby other Y-coordinate shrinkage ratios of the workpiece(s) 1 may similarly accomodated.

In summary, the gear drive train in combination with the flexible prism may be employed to make high precision adjustments for various Y-coordinate shrinkage and/or expansion ratios of the workpiece. This combination provides for average gross sintering shrinkage ratio adjustments by the variable ratio gear drive train and average vernier sintering ratio adjustments by partial rotation of the flexible prism, while concurrently the flexible prism may also make small shrinkage or expansion adjustments for individual workpieces to accomodate ratios and/or factors other than sintering shrinkage ratios.

The Sweeping Laser Spot and Y-Coordinate Registration

Figure 31A:
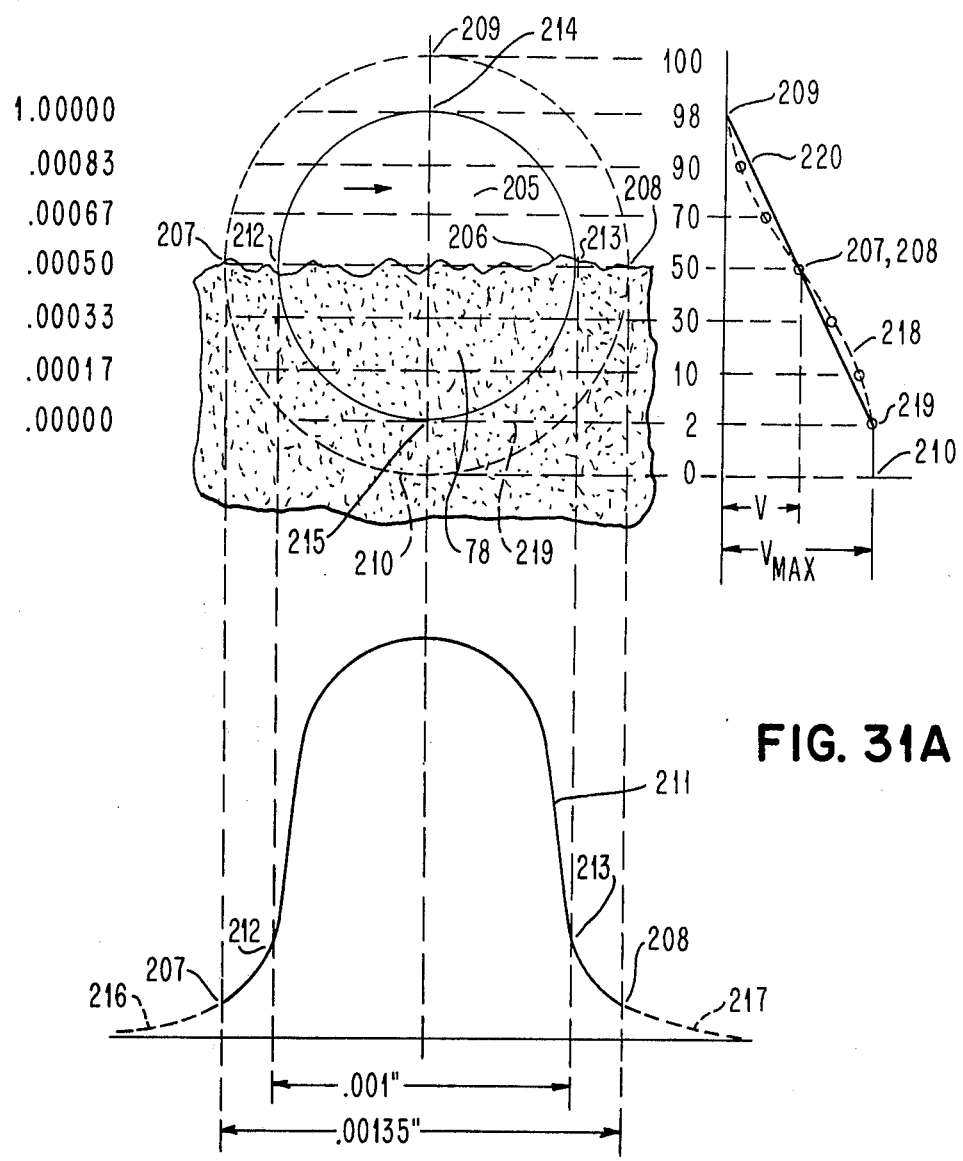
FIG. 31 shows a focused laser spot and approximate energy distribution curves thereof relative to, for example, pattern lines on the workpiece.

Many of the Y-coordinate functions of the sweeping laser spot may be understood from FIG. 31 and associated descriptions. The focused laser beam spot 205 may be sweeping from left to right across the surface of a workpiece 1. The laser light energy is distributed across an X-coordinate diameter 207, 208 or a Y-coordinate diameter 209, 210 of the sweeping spot 205, approximately as projected below in a bell shaped curve 211. The laser energy of the curve 211 is greatest in the broadly rounded central top and decreasing in relatively steep sides sloping downward from the top to a much lower energy at the rim of the bell curve. The laser energy is focused in a manner such that about 80% of the laser energy of the spot is within a circular area having an X-diameter 212, 213 or a Y-diameter 214, 215 of 0.001 inches. The larger circular area that includes the 0.001 inch diameter area may include about 90% of the laser energy and may have a diameter of about 0.00135 inches. Thus considering that the larger laser spot circle of diameter 207, 208 includes approximately 90% of the laser spot energy and is concentric with the smaller circle of diameter 212, 213 having 80% of the laser spot energy, subtracting the area of the smaller circle from the area of the larger circle, the differences between the areas is nearly equal to the area of the smaller circle but only contains about 10% of the laser spot energy. A still lower level of laser spot energy may extend over a much larger area having a diameter 216, 217 on the bell curve 211 with a residual 9% of laser spot energy outside the diameter 207, 208 spread over such a large area that the residual low level energy may be disregarded for practical measurement and inspection purposes. As projected to the right of the circular laser spot 205, photocell voltage response curve 218 shows the response of the photocells 36 (FIGS. 1, 29) to various levels of laser light from the sweeping laser spot 205 such as may be reflected from the workpiece 1 and conducted to the photocells by the transparent light conductor rod 35. The voltage response of the photocells 36 is at a maximum when the laser spot 205 of diameter 209, 210 sweeps entirely over a white area of the workpiece 1 and at a minimum when the laser spot sweeps entirely over a dark area such as registration lines 77A, 77B, 77C (FIG. 17) or the conductor patterns (FIGS. 7A, 8A).

To illustrate the voltage response curve 218 consider that the laser spot is projected to the right to the response curve by the horizontal dash lines as shown. The dash lines divide the larger diameter 210, 209 into 8 equal lengths and correspondingly as cords divide the laser spot circle into sectors having various areas. Starting at the bottom and tangent to the point 210 a horizontal top edge 206 of a dark horizontal registration line 78 (FIG. 17) may be thought of as moving upwards across the circle until it becomes a top tangent at the point 209. When the dark top edge 206 is at the bottom tangent point 210 the laser spot circle may be entirely on a white area of workpiece material and the voltage from the photocells 36, as projected to the right on the reponse curve 218, is at a maximum. When the dark to edge 206 is at the top tangent point 209 the laser spot circle is entirely on a dark registration line 78 with near zero photocell response. At various locations between the bottom tangent 210 and the top tangent 209 the top edge 206 of the registration line is a horizontal cord of the larger laser spot circle dividing the circle into a dark lower sector and a white upper sector with the photocell's 36 responding to a decreasingly white sector area as shown by the curve 218. There may be relatively little laser spot energy in the lower sector between the tangent point 210 and a cord 219 tangent to the inner circle or in an upper sector between a tangent cord line 220 and the tangent point 209. The low sector energy occurs from the small areas of the sectors and the low level of laser energy occurring between the outer circle of diameter 207, 208 and the inner circle of 212, 213 diameter. Thus these small sectors show as approximately vertical lines 210, 219 and 220, 209 on the response curve 218 as the dark area of the registration line moves from point 210 to point 209 and progressively obscures the white area within the outer circle. The curve 218 is slightly S-shaped between the points 219 and 220 and essentially symmetrical about a projected central diameter cord 207, 208 of the outer circle. A straight line drawn from the point 219 to the point 220 closely approximates the curve 218 between these points and provides a linear voltage reference level between the points. Since within the outer circle the cords 219, 220 may also be tangent to the inner 0.001 inch diameter circle the linear voltage reference level may be used to closely approximate the intercept position of the horizontal dark edge 206 with the vertical diameter of the inner laser spot circle. As shown in FIG. 31 the top dark edge 206 of the horizontal registration line 78 may be about ½ way up the vertical .001 inch diameter and when projected to the right to intercept the straight line 219, 220 approximation of the response curve 218 the photocell voltage V may be approximately ½ of the maximum photocell voltage V max. Thus it may be understood that the photocell voltage response voltage V may be at levels proportional to various cord intercepts of the top dark edge 206 as the 0.001 inch diameter laser spot sweeps across a horizontal registration line 78. The horizontal registration line 78A may be 0.030 inches wide for a stable voltage measurement during the laser sweep. The proportional voltage V may be amplified, measured and clamped at the measured voltage level for a period of time. The clamped voltage V may be suitably polarized and applied to the actuators 164, 165, 166, 167 (FIG. 24) of the flexible prism 33 to deflect the sweep line 143, 144 (FIG. 23) of the sweeping laser beam 25.

The enlarged area of the registration pattern 76 (FIG. 13) may otherwise be shown as small areas 49 (FIGS. 4, 5, 6) and duplicated in the left and right margins of the workpiece 1.

The clamped voltage V developed from left margin horizontal registration lines 78 may be applied to the left actuators 164, 165 (FIG. 29) and from the right margin horizontal registration lines 78 the right actuators 166, 167.

The inspection tool may include a computer (not shown) operating from the measured voltage V whose directive command signals determine a suitable voltage and polarity to be applied to the left 164, 165 and/or right 166, 167 actuators of the flexible prism 33. By such command signals the actuators provide + or − rotation to either and/or both ends of the flexible prism 33 whereby either a bottom tangent line 219 (FIG. 31) or a top tangent line 220 of the 0.001 inch sweeping laser spot may be deflected into approximate coincidence and/or registration with the top dark edge 206 of the horizontal registration lines 78A located in the left and/or right margins. If a skewed conditions occurs in the circuit pattern outline 50 (FIG. 16) between the left and right patterns 49 (FIGS. 4, 5, 6) two successive laser spot sweeps across the workpiece 1 may be required to pick up registration signals from the top dark edge 206 the widely separated registration patterns 49 located in the left and right margins; i.e., in this instance the left registration pattern would be lower than the right registration pattern and thus the left pattern might be missed by a laser sweep that picks up a portion of the right pattern. However the next successive laser sweep might pick up a portion of the left registration pattern and the computer may then provide a suitable voltage and polarity for the left and the right actuators of the flexible prism 33 to provide a skewed laser scan line 155, 156 (FIG. 28) for registration purposes. Other horizontal registration lines 78B, 78C of the registration patterns 76 may similarly be used to progressively improve registration. Likewise other registration patterns 49 in the left and right margins and periodically located from top to bottom of the workpiece 1 may periodically correct registration as the workpiece is moved under the sweeping laser beam.

The computer may also be used to provide "rejection signals" when the dark edge 206 is greater than ±0.001 inch from its nominal Y-coordinate position relative to the sprocket holes 3 (FIG. 1) or the registration holes 53, 54, (FIGS. 4, 5); and may also reject a workpiece when the Y-coordinate dimensions of th dark edges 206 in the left and right margins are separated by more than 0.002 inches due to a skewed condition. The above limits on Y-coordinate registration dimensions (FIGS. 10 to 16) may be similar to dimensions previously described relative to limitations on circuit line and via hole locations (FIGS. 7A, 8A) previously described relative to FIG. 9 since the registration pattern and the circuit pattern may be based on using the same 0.006 inch matrix grid and 0.001 inch sub-grid system. Thus if the bottom or top tangents 219, 220 (FIG. 31) of the sweeping laser spot circle are brought into approximate Y-coordinate registration with the top dark edge 206 of a registration pattern, the tangents may thereafter be in approximate registration with the horizontal top or bottom line edges of the conductor pattern circuit lines and the centers of via holes.

In summary, the Y-coordinate registration represents a major and unique feature of the inspection tool inasmuch as without registration the sweeping laser spot circle could encounter a horizontal line edge anywhere within the diameter of the circle and individual calculations based on the photocell response voltage V for 36,000,000 or more zones of 0.001 inch diameter in a 6 inch square workpiece may be required to determine the locations of top and bottom circuit line edges for inspection purposes. These individual zone calculations of course would reduce the inspection accuracy of the inspection tool since the voltage V would not have time to stabilize for each 0.001 inch circular spot zone. Additionally, individual zone calculations might considerably increase inspection time since such individual calculations would increase the work load of the computer.

The Sweeping Laser Spot and X-Coordinate Registration

Many of the X-coordinate functions of the sweeping laser spot may be understood from FIG. 32 and associated descriptions. The X-coordinate functions are similar in part to the Y-coordinate functions. In sweeping from left to right across the workpiece 1 the focused laser spot may encounter vertical portions of vertical registration lines 77A, 77B, 77C (FIG. 17) and/or vertical portions of vertical conductor pattern lines (FIG. 7A, 7B) while concurrently as synchronous portion of the same focused laser spot may be intercepted by the partially reflecting mirror 27 (FIG. 1) and reflected as a focused spot on the grating 28. In FIG. 32 these progressive positions 221, 222, 223 of the 0.001 inch diameter circular portion sweeping laser spot may be shown as the spot approaches 221, intercepts 222, and enters a dark area 223 having a vertical left edge 224 on the workpiece 1. A corresponding voltage response curve 225 of the photocell 36 (FIG. 1) with the centers of the circles 221, 222 projected downward to the curve may show the voltage response as the laser spot sweeps from left to right across the vertical left edge 224. With the laser spot circle 221 entirely on a white area the voltage response may be maximum ($V_{max}$) and when the circle 223 is entirely over a dark area the voltage may be a minimum. The steepest part of the curve 225 occurs as the vertical diameter and the center of the circle 222 sweep over the vertical dark edge 224. By differentiating and rectifying the photocell voltage response, a sharply peaked pulse curve 225 is developed that is symetrical and centered on the dark edge 224. When sweeping from a dark area to a light area the laser spot induces a photocell response curve (not shown) that is the reverse image of the curve 225 and result in another pulse curve similar to the curve 225 and likewise centered on a vertical dark trailing edge. Meanwhile the synchronous laser spot sweeping across the grating 28 (FIGS. 1, 2, 8A to 8D, 21) may develop similar pulses 89 (FIGS. 18D, 31) except that the pulses 89 may be regularly repetitive and centered 0.001 inch part as previously described. In this connection the computer may measure the + or − time difference at between the center lines of the response curve pulse 225 and the nearest grating pulse 89. The time difference may then be converted, in a conventional manner to a higher voltage of the correct polarity with the voltage being proportional to the time difference, and the voltage level clamped at that level and then applied to suitable actuator components 115, 117 or 116, 118 (FIG. 21).

As previously described, the registration patterns 76 (FIG. 17) or 49 (FIGS. 4, 5, 6) may be located in the left and right margins of the workpiece 1. When the response curve pulse 225 are derived from a registration pattern 49 in the left margin of the workpiece 1 the time difference voltage is applied to the actuator components 115, 117 (FIG. 21) to physically move the Grating 28 up to ±0.001 inch to the left or right whereby the grating pulses 89 (FIG. 32) may be moved left or right into alignment and/or registration with the voltage response pulse 225. When the response curve pulse 225 may be derived from a registration pattern 49 in the right margin the time difference voltage are applied to the actuators 116, 118 to physically rotate the grating 28 thereby contracting or expanding the effective length of the grating pulse train to bring the grating pulse 89 into alignment and/or registration with the photocell response pulse 229. It should be understood that there may be dimensional restraints on such physical displacements and rotations of the grating 28 which may not correspondingly exceed the restraints on via hole alignment (FIG. 9) as previously described. In summary, after alignment and/or registration of the grating pulses with the registration pattern pulses the grating pulses should also be in registration with the X-coordinates of the inspection matrix grids and the circuit line patterns.

Alignment and Calibration

The inspection tool may preferably be carefully aligned and calibrated to provide inspection accuracy for dimensions smaller than 0.001 inch. Relative to the workpiece the X-coordinate vector across the workpiece may be at a 90% angle to the Y-coordinate vector along the length of the workpiece, the latter being parallel to the direction of motion of the workpiece during inspection. The sweep line vector of the focused laser spot across the workpiece preferably may be at a slight "lead angle" of 0.001/6.000 from the X-coordinate vector to account for the motion of the workpiece as the laser spot sweeps from left to right across the workpiece. Micrometer calibration means (not shown) may be used to horizontally shift the axis of the rotating mirror 17 (FIG. 30), the shaft 18, the mirror drive motor 19, and the shaft 181 about the flexible coupling 182 as a pivot point to achieve a suitable lead angle.

A manually pre-calibrated nominal workpiece may be slowly fed into the suspension tool by turning off and holding the mirror drive motor while slowing pulsing the stepping motor to provide a slow speed drive. Then by manually rotating the mirror the laser spot is set to the precalibrated positions on the workpiece and the grating adjusted to register with these positions by using the adjustable set screws previously described. The precalibration may be assisted by microscopes and voltimeters, and a more accurate calibration may then preferably be accomplished with the mirror drive motor turned on and with the inspection tool running under full dynamic running conditions. Under dynamic conditions adjustments of various other components may be required until the inspection tool reports a zero erro condition for a nominal workpiece that has been previously inspected and accepted for calibration purposes.

In order to equalize the displacement provided by the actuators of the grating and the flexible prism, conventional potentiometers may be employed. By using suitable reference voltage signals, for example, from a computer, the voltage levels of such reference signals may be clamped at fixed voltage levels until changed by subsequent reference signals. Of course included in the computer program is such a restraint that the clamped voltage levels may only be changed during a "fly-back" period; i.e., after the left-to-right sweeping laser spot has passed beyond the right margin of the workpiece and before it enters the left margin. A "fly-back" period (or more technically correct, a "fly-forward" period in this instance) may occur as the laser beam from the laser source is intercepted by the line between two adjacent faces of the multifacet rotating mirrow with each of the two faces then reflecting separately sweeping laser beams which could confuse the photocell response. Since the "fly-back" time represents a small loss of laser beam sweep time the rotational speed of the workpiece supporting cylinder is slowed proportionately to avoid gaps between sequential laser sweep lines.

In passing, it should be noted that the inspection tool may be employed with a tape, punch card, or computer, it being recognized that what is being accomplished is the inspection of a workpiece and more specifically the pattern thereon to determine whether the pattern on the workpiece matches a predetermined perfect pattern. Thus whether a bell or whistle is employed to indicate a lack of match or a pattern defect or a more sophisticated detection scheme is used such as a computer to store in a digitized format the information relative to the pattern and its comparison is immaterial to the present invention. Obviously, in an inspection scheme where a comparison must be made for a single part number or a small number of part numbers, a punch card or tape comparison scheme may be employed. Alternatively, if a large number of different patterns are to be inspected, a tape or computer scheme using bulk storage such as disc or tape is to be preferred. Additionally, it should be recognized that the scheme employed could be used with a pair of inspection stations with a simple comparator, the first station inspecting the workpiece and the second station inspecting the master pattern, the output, for example of the photocells being compared in the comparator such that if a fault exists, an error signal is displayed. However, it should be noted that in the preferred embodiment, a computer such as the IBM 360/Mod. 65 is the preferred data and comparison source.

Control and Comparison

Various methods may be used to interface the inspection tool's laser scan system and its computer system. A variety of computer systems with memory banks are commercially available. Many commercial computers may be programmed to compute using new and/or stored data in equivalent and/or interchangeable forms such as analog, decimal, binary, voltage, time, etc. and/or combinations thereof. The computer programming for such computers is well known to one skilled in the art and thus is a subject that need not be described herein except for a few schematic block diagrams.

The laser scan system generates "workpiece inspection data" in "real time" as the workpiece 1 progresses through the inspection tool. The "workpiece inspection data" may be compared for agreement with calculated and/or previously stored "correct data images" provided by the inspection tool's computer. Various types of computer programs may be used when such workpiece data is compared for agreement with the correct data image depending on the size and addressing speed of the computer and its memory bank.

Figure 34:
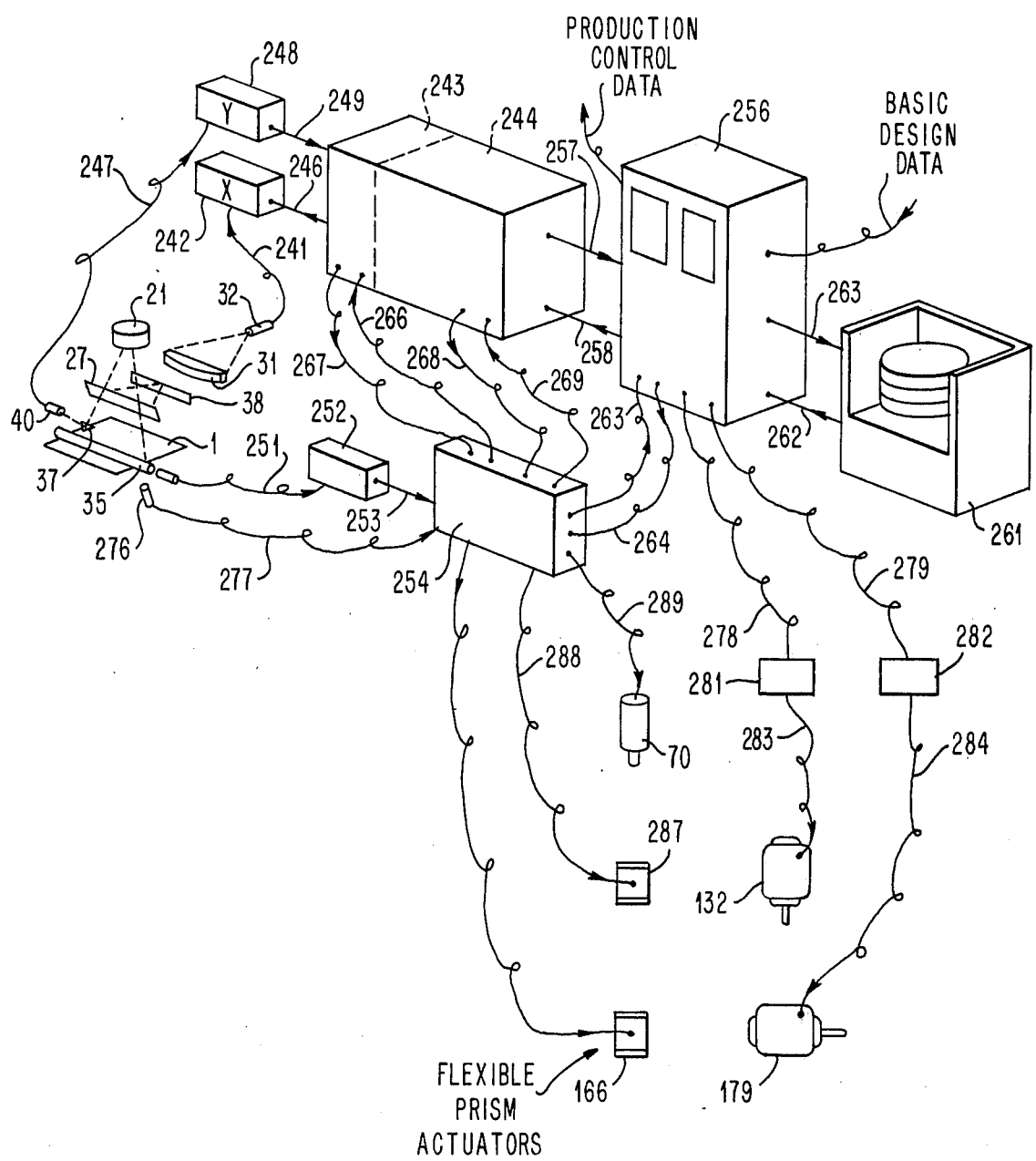
FIG. 34 is a fragmentary schematic perspective view in block form illustrating the operation of the apparatus of the present invention with a computer.

Various types of computer programs may be employed with inspection tool components such as are included in schematic block diagram FIG. 34. Some computer programs may use more or less components and/or the components may be interconnected differently than shown in FIG. 34. The components are shown spread apart for block diagram purposes but may be located in and/or on the inspection tool chassis while the computer components may be located in separate cabinets or in the main computer cabinet. The interconnecting cables shown may include one or more electrical conductors as may be required to perform their functions.

The laser scan system and associated amplifiers, counters and addressers are used in several functions and are described first to avoid repetition in the descriptions of such functions. Referring now to FIG. 34, the first or grating photocell 32 is connected by a cable 241 to an X-coordinate signal amplifier cabinet 242 where the photocell signal is linearly amplified, differentiated, and full wave rectified to provide the X-coordinate incremental marker pulses 89 (see FIGS. 18D and 18G). The cabinet 241 includes a pulse counter for the marker pulses 89 with the pulse counting being initiated at a position corresponding to the wide laser energy transmitting line 89 (FIG. 18E) of the grating 28 and the slope 88 (FIG. 18F) of the grating photocell response curve. The pulse counting initiating location may be somewhat to the left of the registration patterns 45 (FIGS. 4, 5, 6) in the left margin of the workpiece 1 so that the registration patterns are included in an X and Y coordinate recognition program as described later. The X-coordinate pulse count may be used "as is" and/or converted to an X-coordinate address for the momentary location of the sweeping laser spot and then transmitted to the gate section 243 of the correct data memory bank 244 by the cable 246. The cable 246 also transmits the linearly amplified voltage of the photocell 32. The third or margin marker photocell 40 is connected by a cable 247 to a Y-coordinate amplifier cabinet 248 where the photocell signal is linearly amplified, differentiated, and half wave rectified to provide a single Y-coordinate marker pulse from a left margin position to the left of the registration patterns for each single sweep of the laser beam. The cabinet 248 includes a Y-coordinate marker pulse counter that provides data on the momentary Y-coordinate sweep line of the laser inspection spot. The Y-coordinate pulse count may be used "as is" and/or converted to a Y-coordinate address and transmitted by a cable 249 to gate section 243 of the memory bank 244. The cable 249 also transmits the linearly amplified voltage of the photocell 40. The second or workpiece photocell 36 is connected by a cable 251 to a workpiece data amplifier cabinet 252 where the photocell signal is linearly amplified, differentiated, and full wave rectified to provide edge marker pulses for the white to dark and/or dark to white edges of various patterns present on the worksheet 1. The edge marker pulses and the linearly amplified voltage of the photocell 36 are transmitted by a cable 253 to a comparator cabinet 254.

The functions of the gate section 243 of the correct data memory bank 244 may include gating or switching data and/or signals from various components of the inspection system to other components with the controls for such gating being provided by a computer program previously entered and stored in a main frame computer 256. Cables 257, 258 interconnect the memory bank 244 to the computer 256. The gating section 243 of the memory bank may be provided with a permanent data memory of the standardized X and/or Y coordinate locations for registration patterns, part number patterns, other data patterns including X and Y sintering shrinkage rates, circuit line outline patterns, etc. that may be common to all workpieces being inspected. Thus for example, when provided with X and Y coordinate data by cables 246, 249 the gate section 243 may be programmed to segregate registration pattern signals from part number pattern signals etc. or circuit pattern signals by appropriate gating and/or switching programs. Such switching programs may then redirect the pattern data for internal use and/or redirect the pattern data and/or gating signals to other components of the inspection tool for use therein and/or further data processing.

Functions and signal responses of various electrooptical, electro-mechanical, and computing components of the inspection tool have been described previously and need not necessarily be repeated relative to FIG. 34 except to briefly describe data signal, command signal, computing, and computer programming interrelations.

A computer program is applied to the main frame computer 256 from a remote terminal or from a local magnetic disc file 261 by means of cable 262, and the remote program may be stored in the disc file 261 by means of cable 263. Basic circuit pattern design data may be applied to the main frame computer 256 from a remote terminal in a conventional manner, the design data applied may have been pre-expanded for inspection use to a correct data image(s) (0.006 inch X, Y grid with 0.001 inch sub-grid). For an unsintered circuit pattern(s) the data may be applied to the memory bank 244 by means of cable 258 and/or applied to the disc storage file 261 by means of cable 263. Alternatively if the nominal design data fed to the computer by the terminal has not been expanded for inspection use (0.005 inch X, Y grid with 0.005 inch sub-grid) the computer may use such data to generate a correct data image (0.006 inch X, Y grid with 0.001 inch sub-grid) for inspection purpose use, as described heretofore, and the correct data image for the inspection of a circuit pattern then applied to the memory bank 244 and/or the disc storage file 261. Of course the computer 256 may provide a production control data and/or additional data to remote equipment in a well known manner.

The comparator 254 intercommunicates data with the main frame computer 256 by means of cables 263, 264, with the gate section 243 by means of cables 266, 267, and with the correct data image memory bank 244 by means of cables 268, 269. The cable 253 provides the comparator 254 with amplified white and/or dark signal data from the workpiece 1 and marking pulse data to the edges of white and/or dark patterns on the workpiece. As the worksheet passes through the laser inspection or work zone the sprocket holes 6 (FIG. 1) of the workpiece engages the sprocket pins 12 of the cylinder 9 with sufficient accuracy such that programmed X-Y gating signals from the gate section 243 may be used to segregate various patterns on the worksheet such as registration patterns from part numbers etc. and/or from circuit pattern areas.

The gating program may be activated for each of four sequential workpieces being inspected, for example, by using four reflecting marks 273 (FIG. 1) on the end of the cylinder 9 with the marks being positioned to correspond with the separating lines 44 between sequential workpieces. A light source 274, the reflecting mark 273 and a cylinder photocell 276 cooperate to provide an activating signal to a cable 277 connected to a signal amplifier in the comparator 254. The amplified activating signal is passed to the gating section 243. It should be recognized that the gating program could also be activated by marks on the workpiece.

As the sweeping laser spot traverses the leading edge margin 48 (FIG. 4) of the workpiece(s) 1 the activated gate section 243 segregates the part number data on cables 253, 266 from other data, decodes the data, and uses the decoded part number data to select and designate a correct data image from data in the data bank 244. Concurrently the gate section 243 segregates X and Y sintering shrinkage rate data, decodes the data, and transmits the decoded data to the main frame computer 256. The computer 276 is programmed to encode the decoded X, Y sintering shrinkage data to format signals suitable for controlling the grating motor 132 (FIG. 21) and the stepping motor 179 (FIG. 30). Such X and Y format signals are transmitted by cables 278, 279 to power amplifiers and controllers 281, 282 which provide cables 283, 284, 286 with suitable power controls for the motors 132, 179. By such means the encoding disc 134 of the motor 132 (FIG. 22) cooperate to rotate the grating 28 which may not provide "nominal" X-coordinate inspection dimensions that include sintering shrinkage compensation. Similarly by such means the stepping motor 179 adjusts the rotational speed of the cylinder 9 which provides "nominal" Y-coordinate inspection dimension that include sintering shrinkage compensation.

Also concurrent with part numbers and sintering shrinkage data from the leading edge margin 48 (FIG. 4) of the workpiece 1, the activated gate section 243, using data on cables 253, 266 segregates the data signals of vertical registration lines 77A, 77B, 77C (FIG. 17) from horizontal registration lines 78A, 78B, 78C in both the left and right margins of the workpiece(s) 1. The segregated vertical and horizontal registration line data is returned to the comparator 254 by means of the cable 267. In the comparator 254 line edge pulses from the vertical registration lins in the left margin are compared for X-coordinate displacement relative to the grating line edge pulses from cables 246, 267. The comparator 254 generates a signal that is proportional to the magnitude and direction of the X-coordinate displacement, amplifies the voltage and power of the signal, and transmits the amplified signal to suitable grating actuators 287 by means of a cable 288. Suitable grating actuators 287 then provide vernier motion to move the grating 28 to the left or right to bring the grating line edge pulses into alignment with line edge pulses of the vertical registration lines. This procedure may be repeated for vertical registration lines periodically located lower in the left margin of the workpiece and thereby periodically registering the grating to the left edge of the circuit pattern area. A similar procedure may be used with the vertical registration lines in the right margin of the workpiece whereby suitable actuators 287 may apply a vernier rotary action to the grating 28 to bring the grating pulses into registration with the right edge of the circuit pattern area. Additionally, in this instance, periodic grating measurements may be taken of a dimension between vertical registration lines in the left margin of the workpiece and corresponding lines in the right margin. This dimension should preferably be taken before vernier grating adjustments are made. If the dimension differs from the "nominal" dimension including manufacturing tolerances the comparator 254 may issue a power amplified reject signal on cable 289 to an accept or reject marker 70 that applies a reject mark in the right margin of the workpiece.

A somewhat similar system may be used to obtain Y-coordinate registration of the sweeping laser spot to the circuit pattern of the workpiece, but in this instance using a data signal voltage data signals from the horizontal registration lines 78A, 78B, 78C (FIG. 17) in the left and right margins of the workpiece(s) 1, together with other data signals, are sent on the cable 253 to the comparator 254. The data signals are sent on cable 266 to the gate section 243 where the data signals from the left margin horizontal registration lines are segregated from other data signals and returned to the comparator 254 on cable 267. Likewise the data signals from the right margin horizontal registration lines are segregated and returned to the comparator 254. The horizontal registration lines are sufficiently long (e.g. 0.030 inches) such that a stable voltage measurement may be taken from the segregated left and right margin data signals. Such voltage measurements are then compared to standardized white and/or dark voltage signals whereby the relative overlap of the sweeping laser spot on white and/or dark horizontal registration lines may be used to generate suitable signals that are proportional to such overlaps. Such overlap signals are power and/or voltage amplified and transmitted by means of a cable 292 to suitable flexible prism actuators 293. Thus segregated data signals from the left margin horizontal registration lines may thus be used by suitable actuators 293 to apply vernier rotation to the left end of the flexible prism 33 and from the right margin horizontal registration lines for vernier rotation to the right end of the flexible prism 33. Note that if the vernier rotations of the left and right ends of the flexible prism 33 are not identical and/or in the same direction of the flexible prism may be twisted. By such means the sweeping laser beam passing through the flexible prism 33 may be deflected by vernier prism rotations into Y-coordinate registration with the circuit line pattern on the workpiece 1. This procedure may be repeated with horizontal registrations located lower in the left and right margins of the workpiece thereby periodically checking and/or improving the Y-coordinate registration of the sweeping laser beam to the circuit line pattern. Additionally, in this instance, if the prism deflections are greater than the manufacturing tolerances for a workpiece 1, the workpiece may be rejected by a power amplified signal on cable 289 to the accept, reject marker 70.

The data signals of circuit line patterns on cable 254 together with other data signals may be redirected through the comparator 254 to cable 266 and the gate section 243 where the circuit line pattern data is segregated from other data. The segregated pattern data is returned to the comparator 254 by cable 267. As previously selected and designated by the workpiece part number, the correct image data in the correct data memory bank 244 responds to X and Y coordinate addressing by laser spot positional data on cables 246, 249. At any such addressed X and Y coordinate the correct image data provides either a white or a dark data signal for that address and the data signal is transmitted to the comparator 254 by means of cable 294. The comparator 254 then compares the segregated circuit pattern signal on cable 267 with the white or dark signal from the correct image data on cable 294. Then if a white circuit pattern signal is in agreement with a white correct data image signal and/or a dark circuit pattern signal is in agreement with a dark correct data image signal the portion of the circuit pattern at the X, Y address being inspected by the sweeping laser spot is assumed to be correct. However, if a white pattern signal occurs in disagreement with a dark correct data image signal, or vice versa, there may be a potential defect in the circuit pattern at that X, Y coordinate address that requires further evaluation before accepting or rejecting the workpiece. To effect such an evaluation a white error signal or a dark error signal is transmitted by cable 297 for storage in an error section 296 of the memory bank 244 while concurrently the X, Y coordinate address of the error on cables 246, 249 is also stored therein. The black or white error signals are also transmitted by cable 264 to the computer 256 where a mini-program is initiated to determine the extent and hazard of the error and/or subsequent errors at contiguous X, Y coordinate addresses. The cables 257, 258 transmit error data between error section 296 and the computer 256 whereby the mini-program may determine that white errors extending half-way or more across a dark conductor line are potentially hazardous electrical open circuits to be rejected, and/or that dark errors extending half-way or more between adjacent conductor lines are potentially hazardous electrical short circuits to be rejected. Rejection signals from the mini-program are transmitted by cable 264 to the comparator 254 for power amplification and to accept or reject marker 70 by cable 289. If all circuit pattern data is in aggreement with the correct image during the inspection of the workpiece and no potentially hazardous errors have been found the comparator generates and power amplifies an accept signal that is transmitted to the accept or reject marker 70 by cable 289.

When a workpiece 1 is rejected for any course such as dimensions, errors, etc. rejection data including type of rejection and/or error, the X, Y coordinate address of the error, and part number are stored in the error section of the memory bank 244. Then if another sequential workpiece of the same part number has the same error at the same address location, the computer 256 may be programmed to issue a warning signal on cable 272 that includes the rejection data. It is probable that the next corresponding workpiece may include the same course for rejection and that diagnostic and/or corrective action may be required earlier in the production line processing. Thus rejection data on cable 272 may be sent to a remote location where such data may be used to save valuable diagnostic time by automatically positioning a microscope over the rejection area address on a corresponding workpiece. The cable 272 may also be used to send various production control data that is available from the inspection tool system to a remote production control computer system.

Data Handling, Program

In order to obtain a maximum production througput of workpieces, from the inspection tool equipment the highest practical speed of the laser inspection components preferably should not be limited by the highest practical speed of the data handling components and vice versa. Also the inspection tool's correct data memory bank and computer preferably should be limited to economically practical sizes. The size and/or capacity of the memory bank may be reduced by data compression but data compression may also increase the effective size of the computer.

Three data memory bank and computer systems are described below, in which the second and third systems use various methods for data compression. Data bits, data bytes, data addresses, and data numbers etc. may be herein described generically as data points.

The first system is essentially a one-to-one system with no data compression. In such a one-to-one system the memory bank stores complete and correct image data for one or more workpiece(s) with the data preferably being automatically selected and designated by the workpiece part number. Within the stored correct image data a white or dark signal is stored for each X, Y address point and when suitably addressed by data from sweeping laser spot on the grating each such address point may issue a white or dark signal for comparison to correspondingly positioned data from the workpiece(s). Thus if a 6.000 inch by 6.000 inch workpiece were to be inspected at 0.001 inch X and Y increments there would be 6000 × 6000 = 36,000,000 X, Y addressable data points in the correct image data for each workpiece part number. Considering that there may be as many as 100 or more different part numbers a very large correct data memory bank may be required to provide high speed access to 100 × 36,000,000 = 3,600,000,000 X, Y addressable data points. However, this system may use a relatively small computer.

The second system may use data compression for X-coordinate data. For an example of such data compression a dark circuit conductor line 1.000 inch long horizontally in the X-coordinate and 0.006 inches wide vertically in the Y-coordinate may be used. With the left to right sweeping laser spot X, Y registered to the circuit pattern the sweeping laser spot may first encounter a white to dark transition at the 0.006 inch vertical width of the dark circuit conductor line. The X, Y address of this first transition from white to dark is in the memory bank as correct image data and a dark signal is issued for comparison to work sheet data which should also provide a dark signal. However, in this instance, for data compression purposes, the white to dark transition signal from the correct image data activates a dark signal latch circuit in the comparator that stays latched and continues to issue dark signals for the next 99 X, Y coordinate addresses of the 1.000 inch long dark line to the right of white to dark transition signal. Since such latch circuit issued dark signals are the equivalent of correct image data signals the latter need not be included in the correct data memory bank and data compression thereby accomplished. The dark signal circuit stays latched until the sweeping laser spot traversing the dark line encounters the end of the dark line and a dark to white transition location. At this location and X, Y address the correct image data should issue a white signal for workpiece data comparison purposes. This white signal unlatches the dark signal latch circuit and latches a white signal latch circuit in the comparator that stays latched and issues white signals at consecutive X, Y coordinate addresses until a dark signal is received to unlatch the white signal circuit and latch the dark latch signal circuit, etc. In using this data compression system only the X, Y coordinate addresses of white to dark and dark to white transitions are required to be addressable and maintained in the correct memory data bank thereby accomplishing a data compression of about 95% for dense circuit patterns. Thus relative to the previously described system No. 1 only about 0.05 × 3,600,000,000 = 18,000,000 addressable memory points may be required for about 100 different workpiece part numbers in a large memory bank.

A third system may use a smaller memory bank and a larger computer for data compression by generating correct image data from a memory bank part number program and a moderate quantity of memory bank "characters". If the original circuit pattern designer has followed the "ground rules" the 6.000 inch by 6.000 inch square of the workpiece being inspected may be thought of as being covered by an orthogonal matrix of small 0.012 inches by 0.012 inches square areas, hereinafter called characters. The four edges and the centers of such small square characters may align with a 0.006 inch by 0.005 inch X, Y matrix grid line pattern occurring from and used as the original pattern design reference matrix mut not actually present on the workpiece being inspected. The circuit conductor lines, conductor filled via holes, etc. are "centered" on X, Y grid lines of the 0.006 inch X, Y matrix grid that pass through the center of the small square character areas. Thus if a complete circuit pattern were to be cut (not actually) into the small square characters described above like pieces of a puzzle, and mixed up, each square character would retain a portion of the pattern and the complete circuit pattern could be reassembled, but with difficulty, from the square character pieces. However, if each character piece were to have a microscope readable number, and the puzzle assembler were to have a code sheet providing character numbers for a reassembly sequence for the puzzle, the complete pattern could be reassembled rapidly. The above puzzle analogy may provide an over-simplified description of the No. 3 system of data compression but may illustrate the principles involved in practical applications of the system. A square circuit pattern area 6.000 inches wide and 6.000 inches high may have 6.000/0.012 = 500 character areas in width and height or a total of 500 × 500 = 250,000 character areas in a complete circuit pattern, or for 100 part numbered workpieces 100 × 250,000 = 25,000,000 character areas. However, by arranging different individual characters in different sequences and/or locations only about 50 different characters may be required to complete a circuit pattern. An analogy for this is a typewritten page where only about 75 capital and small letters A to Z punctuation marks, and decimal numbers 0 to 9 may be typed in different sequences and/or location to fill a page, or 100 pages.

As described previously the character areas are 0.012 inches by 0.012 inches square with reference vertical and horizontal center lines of the 0.006 inch X, Y reference grid matrix intersecting at the centers of the character areas. The character areas include a 0.001 inch X, Y reference sub-grid and thus there are 12 × 12 = 144 sub-grid areas each of the larger character area. Each 0.001 inch square sub-grid area is either white or dark according to the pattern configurations that may be required to form individual characters in the larger (0.012 inch square) character area. A few examples of individual character patterns are described below and assigned sequential numbers 01, 02, 03 etc.:

01. An all white character area
02. an all dark character area
03. A white area with a vertical 0.006 inch wide bark line area centered on the vertical center line.
04. A white area with a horizontal 0.006 inch wide dark line centered on the horizontal center line.
05. The pattern of (03) above with a dark horizontal 0.006 inch wide stub line extended to the right and centered on horizontal center line.
06. The pattern of (05) above except that the dark stub line is extended to the left.
07. The pattern of (04) above with a dark vertical 0.006 inch wide stub line extended upward and centered on the vertical center line.
08. The pattern of (07) above except that the dark stub line is extended downward.

09. The patterns of (03) and (04) above combined to form an intersection cross.
10. A white area with an L shaped dark configuration comprising a dark vertical line 0.009 inches long and 0.006 inches wide extending from the top of the square downward that is centered on the vertical center line, with a 0.006 inch wide dark stub line extending to the right that is centered on the horizontal center line.
11. The configuration of (10) above rotated 90° clockwise about its center point.
12. The configuration of (10) above rotated 180° clockwise about its center point.
13. The configuration of (10) above rotated 270° clockwise about its center point.
14. A white area with a centered 0.007 inch diameter dark circle (via hole cap). In this instance the curvature of the circle may be simulated by white and/or dark 0.001 inch sub-grid squares and/or sub-grid squares in which about 40% of the squares ares is white and/or dark. Such 40% squares preferably should be provided for by including special data in the correct image data for comparison of photocell voltage responses.
15. The configuration of (14) above with a 0.006 inch dark stub line extending to the right and centered on the horizontal center line.
16. The configuration of (14) above rotated 90° clockwise about its center point.
17. The configuration of (14) above rotated 180° clockwise about its center point.
18. The configuration of (14) above rotated 270° clockwise about its center point.
1. to 18. Notes: Substantially all 6.000 inch by 6.000 inch square circuit line conductor patterns may be assembled from combinations of the above described characters. Ground plane and voltage plane conductor patterns may require additional characters. If permitted by the "ground rules" other additional characters may be included for various diagonal line patterns. A 6.000 inch by 6.000 inch matrix of various characters may be assembled from data stored and addressable by the workpiece part number. Such stored data may include an X, Y coordinate address for the center of each character and the characters configuration reference number (—). Since there would be 500 horizontal lines of X-coordinate addresses and 500 vertical lines of Y-coordinate addresses for the characters in the matrix of characters there would be a total of 500 × 500 = 250,000 X, Y coordinate addresses for the characters of each workpiece, or 25,000,000 addresses for 100 different workpieces. The data configuration of each individual 0.012 inch by 0.012 inch character may be permanently stored in the correct image data memory bank as × 12 = 144 correct image data points, and when suitably addressed by its configuration number (—) and its X, Y address make such data available at the X, Y address. Since there may be 50 different characters the correct memory data bank may require permanent storage for 50 × 144 = 7200 addressable data points which may be additive to 25,000,000 addresses for 100 part numbers previously described.

A computer program for assembling the characters of each 6.000 inch square circuit pattern should preferably assemble the characters in sequential horizontal rows of contiguous characters starting from the left margin of the workpiece. Thus a contiguous horizontal of rows of 50 such characters would be in an area 6.000 inches wide (X-coordinate) and 0.012 inches high (Y-coordinate). The computer assembling program should also include means whereby the data points stored as 0.001 inch sub-matrix data in contiguous horizontal rows of such contiguous characters 6.000 inches wide (X-coordinate) and 0.001 inches high (Y-coordinate) may provide X, Y addressable sub-grid correct image data points sequentially and continuously from the left to right margins of the circuit conductor pattern. Additionally, the computer program may include means whereby two horizontal rows of contiguous characters may be used on an alternating basis; a first horizontal row of previously "set up" contiguous characters being addressed for sub-grid correct image data while concurrently a second horizontal row is being set up with contiguous characters by the workpiece part number program. After the addressing of the first row is completed, addressing is switched to address the second of contiguous characters and the program erases the first row program. Concurrently with the addressing of the second row of contiguous characters the first row is being set up with contiguous characters by the workpiece part number program, its next designated Y-coordinate row of contiguous characters. After the addressing of the second row of contiguous characters is completed, addresing is switched to the first row and so on until the addressing of correct image data points is completed for a 6.000 inch by 6.000 inch circuit pattern.

After the automatic reading of the workpiece part number in the leading edge margin of the workpiece this system for data compression provides about 36,000,000 correct image data points for each different workpiece part number, but data for 100 such part numbers requires only about 25,000,000 memory bank stored data points. This represents a data compression factor of about 144 when compared with about 3,600,000,000 uncompressed data points required for 100 workpiece part numbers.

Operation of the Inspection Tool

The overall operation of the laser beam inspection tool will be described in terms relative to previous component descriptions. The overall operation may include a number of sequential sub-operations:

1. Loading the inspection tool with a workpiece or a long web or workpieces, manually setting adjustments to compensate for gross shrinkage and/or expansion of the workpiece, manufacturing tolerances etc. if required, whereby the nominal workpiece dimensions are established, and starting up the tool's inspection operations.

2. As a workpiece passes through the narrow inspection zone the tool may identify the workpiece part number, job lot number, day code number, shrinkage and/or expansion numbers, etc.

3. Informing the computer of the inspection tool relative to data acquired in 2 above whereby the computer selects a correct inspection program from its data bank and/or generates a corrected program by computation.

4. If further gross adjustments for shrinkage or expansion may be required based on data from 2 above, nominal workpiece dimensions may be restablished by automatically adjusting the position of the grating by using its position seeking motor, and automatically changing the rotational speed of the workpiece cylinder.

5. With the grating and the flexible prism in nominal positions (actuators not energized) the upper left and right registration patterns may be inspected for dimensional data.

6. The workpiece may be rejected if dimensions from 5 above may exceed the nominal dimensions including manufacturing tolerances by applying a rejection symbol in the right margin of the workpiece in line with the rejection defect. This may be applied in any conventional manner, such as a printing wheel, ink jet etc.

7. If the dimensions from 5 above differ from the nominal dimensions of the workpiece but are within acceptable manufacturing tolerance limits, suitable voltages will be automatically applied to the actuators of the grating and the flexible prism whereby vernier adjustments are made to deflect the sweeping laser beam spot from its nominal positions and into registration with a suitable inspection matrix grid which corresponds to the actual circuit pattern dimensions of the workpiece.

8. Inspection of the circuit pattern area on the workpiece for correct pattern dimensions and potential electrical short and/or open circuits.

9. When defects in circuit pattern dimension errors are found in 8 above, the computer will compare such errors with allowable dimensional tolerance limits and if excessive may reject the workpiece. Thus a nominally dimensioned workpiece with a small dimensional error may be accepted whereas another workpiece having dimensions near the limit of manufacturing tolerances may have an error in the wrong direction sufficient to cause rejection. When rejected, a rejection symbol may be placed in the right hand margin in line with the rejection defect.

10. When a potential short and/or open circuit is found in 8 above, the computer may analyze the extent of the short and/or open circuit. This may involve data from several successive sweeps of the laser spot to reveal contiguous defects extending from one circuit line conductor to another conductor causing the workpiece to be rejected, whereas if the contiguous short circuit defects stop at 0.003 inch or more from another conductor, the workpiece may be accepted. Similarily if contiguous open circuit defects extend across a 0.006 inch wide circuit line conductor the workpiece may be rejected, whereas if the open circuit defects extend into the conductor 0.003 inch and are no wider than 0.006 inch the workpiece may be accepted. When the workpieces are rejected for short and/or open circuits a rejection symbol may be placed in the right hand margin in line with the defect.

11. Periodically spaced additional registration patterns may be placed in the left and right margins from the bottom of the workpiece. Such registration marks may be used to correct the registration of the sweeping laser spot using a procedure similar to that described in 7 above.

12. After completing the inspection of the circuit pattern area the grating and the flexible prism may be returned to their nominal positions (actuators not energized) and the lower left and right registration patterns may be inspected for dimensional data.

13. The workpiece may be rejected if dimensions from 12 above exceed the nominal-dimensions including manufacturing tolerances by applying a rejection symbol in the right margin of the workpiece in line with the rejection defect.

14. The succeeding workpiece may now be manually or automatically fed into the inspection zone of the inspection tool and the sub-operations 2 to 13 above may be repeated. Note that this next workpiece may have a different part number, circuit pattern, etc.

15. If desired, when two or more successive workpieces having the same part number have similar rejection defects located in substantially the same position, a warning signal may be issued to the inspection tool operator. The warning signal may appear on the tool's control panel as a visibly readable part number with the X and Y coordinates of the defect. This provides a convenient means for locating the source of the defect in previous processing operations before inspection.

16. The computer may also conveniently provide a production control data for workpieces such as the quantity of various part numbers accepted, throughput rates, rejection rates, day codes, job lot numbers, etc.

COMPARISONS OF INSPECTION FUNCTIONS

Figure 33A:
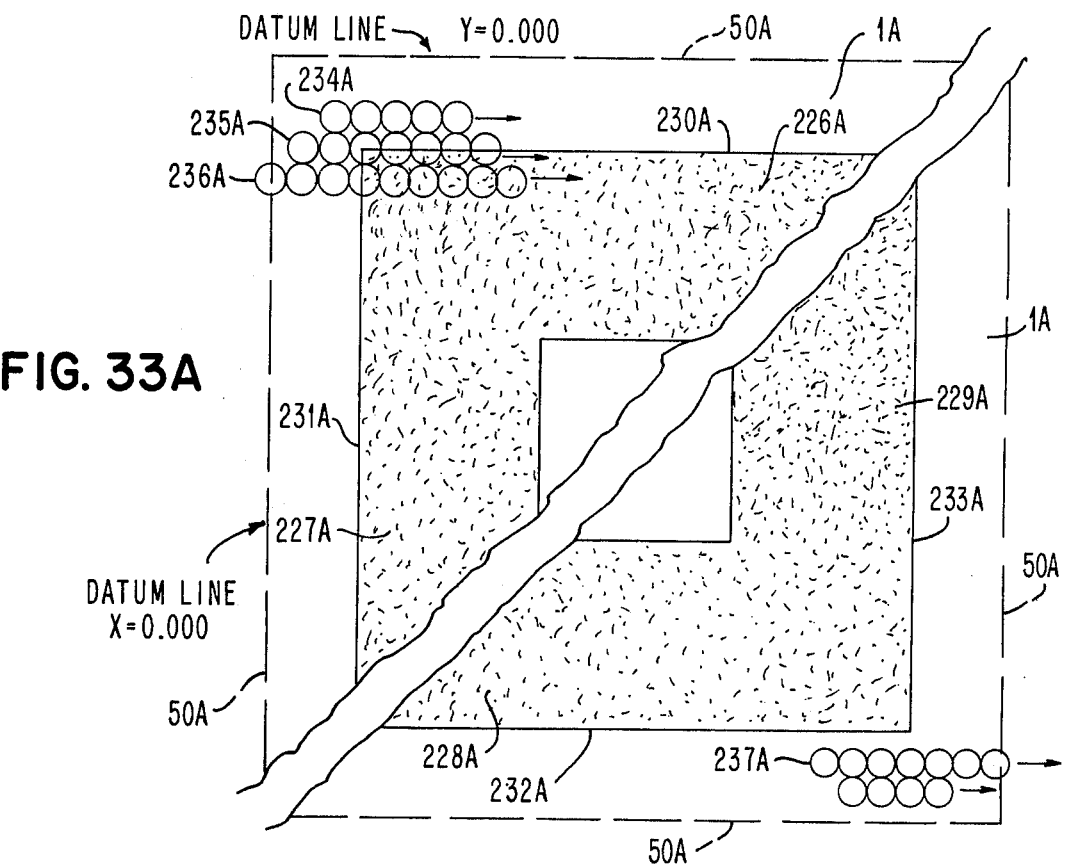
FIG. 33 shows a spot pattern position relative to a line or lines before and after employment of the apparatus of the present invention.

While accuracy and cost effectiveness may be the prime overall objectives of a mechanized inspection tool it may be understood that numerous trade-offs between accuracy and cost have been considered during the evolution of a preferred and/or optimum design. Some of the problems involved in an unused earlier design are shown in FIG. 33A. Below it in FIG. 33B, for comparison purposes, are the results of solving the problems with the preferred and/or optimum design described heretofore and that provides greater inspection accuracy and speed at a lower cost. As used herein the drawing of FIGS. 33A and 33B employ duplicate numbers but with the suffix "A" applying to the unused earlier design and the suffix "B" applying to the preferred design.

Figure 33B:
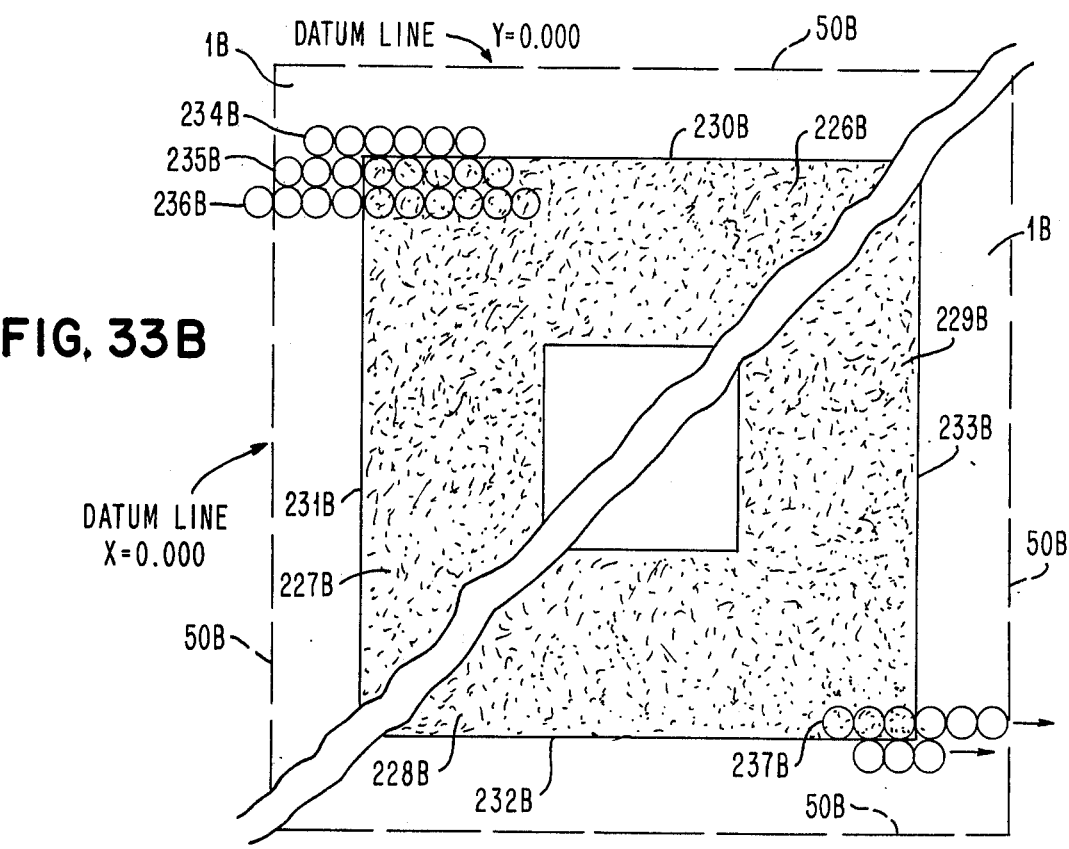

Horizontal conductor lines 226A, 226B may interconnect with vertical conductor lines 227A, 227B near the upper left corner of the workpiece(s) 1 with the white-to-dark external edges of the conductor lines being 230A, 230B and 231A, 231B respectively. Similarly horizontal conductor lines 228A, 228B may interconnect with vertical conductor lines 228A, 229B near the lower right corner of the workpiece(s) 1 with the white-to-dark external edges of the conductor lines being designated 232A, 232B and 233A, 233B respectively. As shown in FIGS. 33A, 33B the conductor lines may be 0.006 inches wide and a large central portion of the worksheet(s) 1 is shown broken away by the diagonal break lines so that only the remaining corner portions are shown. For dimensional reference purposes "datum lines" for Y=0.000 and X=0.000 may coincide with the top line and the left line of the circuit pattern outlines 50A and 50B respectively.

In the earlier design it was purposed to use 28.000 laser sweep lines per revolution of the cylinder 9 (FIG. 1) whereby a 0.001 inch Y-coordinate sweep line grid might be obtained; i.e., 4 sheets of 7 × 7 inch material with workpieces 1 centered in the sheets, 7 × 4 = 28 inches per revolution of the cylinder. A problem then evolved in obtaining 0.001 inch inspection reasuring increments along the sweep lines for X-coordinate measurements. The problem is that the position of the focused laser spot on the worksheet may be a tangent of the angle 24–26 (FIG. 3) function, and the sweep velocity is a square function of the secant of the angle. The problem might have been partially corrected by adding a large negative lens system to the laser optics for tangent compensation but inspection accuracy might be impaired. A better correction approach might be to have the computer interpret the angle and calculate suitable secant function compensations.

Also in the earlier design it was proposed to use an average sintering shrinkage factor 0.828 whereby the X and Y inspection dimensions could be expanded by calculation from the sintered design dimensions. Thus, for example, in FIG. 33A if the sintered design dimensions for the dark edge lines 230A, 231A were each 0.0025 inches from their respective X and Y datum lines their inspection dimensions may be 0.0025/.828 = .003019 inches or 3.019 scan lines or scan line increments from their respective X and Y inspection datum lines. Likewise if the dark edge lines 232A, 233A were each 4.9975 inches from their datum lines in the sintered design their inspection dimensions would be 4.9975/.828 = 6.035628 inches or 6035.628 scan lines or increments from their inspection datum lines. Similarly the 5 × 5 inch sintered dimensions of the circuit pattern outline may be expanded to 6.038647 × 6.038647 inches for scan line and/or increment counts of 6038.97 × 6038.647 for inspection purposes. This introduced problems of how to cope with inspection dimensions such as 3.019, 6035.628, 6038.647 scan lines and/or increments since the computed data may include decimal points with significant data to the right of the decimal points. Also since only integer scan lines and/or increments may be readily counted to determine line and/or circuit pattern positions, other problems and inaccuracies could be introduced by not using or rounding out the data to the right of the decimal point.

Likewise in the earlier design it was believed that up to a ±.0005 inch mechanical registration error between the workpiece sprocket holes 3 (FIG. 1) to the sprocket pins 12 might be within adequate accuracy limits for inspection purposes. Thus the upper dark edge lines 230A, 230B and 231A, 230B might be 0.0005 inch higher and to the left of its calculated position. However if the workpiece also has a 0.001-inch pre-inspection shrinkage that was cumulative to the registration error, then the lower dark edge lines 232A, 232B and 233A, 233B would be 0.0015 inches higher and to the left of calculated positions.

Of the complete laser raster scan pattern only portions of 3 upper laser sweep lines 234A, 235A, 236A and 1 lower sweep line 237A are seen in FIG. 33A. If the sweep lines and their X-coordinate increments have been accurately registered to the inspection tool previously, the increments along the sweep line 234A will be entirely on white areas and the photocells 36 (FIG. 1) may readily recognize white signals. The white signals may then be compared with correct white data image for the increments in, for example, the computer memory bank and the photocell signals accepted as being correct. The next sweep line 235A may encounter problesm since the dark edge lines 230A, 231A may be 0.0005 inches higher and to the left of where they should be due to mechanical registration errors of the workpiece 1A. Thus some increments of the sweep line 235A may be half on white and half on dark while the correct data image may be for white increments only and consequently the inspection process may become confused. Similar confusion may be generated as the upper sweep line 236A traverses the vertical dark edge line 231A since an increment can straddle the line and a half white half dark signal may result for that increment. Likewise, confusion might occurf or increments havng 10% to 90% white or dark area. One alternate to confusion might be to call a confused increment either all white or all dark; and thus allow an error up to 0.0009 inches, which error might be cumulative with other errors. Another alternate might be to disregard confused increments and not compare them with correct image data which might allow similar errors. Voltage interpolation of confused increment data might be used to determine pattern line locations but this might require additional time for voltage stabilization and measurement for each of the 36,000,000 or more increments and slow down the inspection tool to an unacceptable low speed. As previously described, the dark edge line 232A in the lower corner may be 0.0015 inches higher than it should be due to cumulative errors and thus a portion of the lower sweep line 237A which should be totally within the dark circuit line 228A miss the circuit line entirely. An analysis of skewed patterns (FIGS. 14, 15, 16) indicated that further errors were possible. If all the errors were to be cumulative in a wrong direction the sum of the erros could be nearly 0.003 inches, which may be unacceptable for inspection purposes (depending upon line thickness, pattern density etc.), thus indicating that a different design approach is required.

Some of the accomplishments of the different and preferred design approach are illustrated in FIG. 33B. In the preferred design the X-coordinate laser sweep lines and their 0.001 inch X-coordinate increments are registered to the circuit pattern of the worksheet 1 rather than having the sweep lines and increments registered to a fixed element of the inspection tool. This is accomplished by adding easily recognizable and standardized registration patterns in the margins of the workpiece(s) 1 adjacent to the circuit pattern outline area 50. Then by making accurate measurements between the left margin registration pattern and the right margin pattern registration pattern the upper left and right corner locations of the circuit pattern outline 50 may be determined since there is standardized or predetermined dimension between the registration patterns and the circuit pattern outline 50. To make accurate measurements, the partially reflecting mirror 27 (FIG. 1), the grating 28, the lens 31, and the photocell 32 were added to the earlier design whereby the position of the laser spot on the workpiece could have a duplicate spot position on the grating for generating 0.001 inch X-coordinate increment signals and for measurement purposes. After making the measurements between the registration patterns, measurement data from the left registration pattern are converted into suitable voltage signals and applied to the grating actuators 115, 117 (FIG. 21) thereby moving the grating slightly left or right to bring the grating pattern into registration with the registration pattern and the circuit line pattern. Since the grating pattern generates the 0.001 inch X-coordinate increments used for measurement purposes the grating "datum line" may now be registered to the "datum line" circuit line pattern. The effect of such X-coordinate registration may be seen in FIGS. 33B and 32. The preferred effect of such registration is that the laser spot 221 (FIG. 32) is entirely on a white area and the next laser spot 223 is entirely on a dark area with a vertical line such as 224 being mutually tangent to both spots. Portions of the laser sweep lines 235B, 236B (FIG. 33B) show the vertical line 231B mutually tangent to white and dark laser spots. Thus for the upper left corner of FIG. 33B the photocells 36 (FIG. 1) respond only to white spots or dark spots when comparing signals with the image data in the computer memory bank and no interpolation or data omission may be involved. Similarly the ±0.0005 mechanical registration error of FIG. 33A may be avoided by the registering the X-coordinates of the laser sweep pattern to the workpiece pattern. Also the grating, in providing dimensionally stable 0.001 inch increments, avoids repetitive computer calculations that otherwise would be required to compensate for tangent and/or secant functions of the angle 24–26 (FIG. 3) thereby saving computing time.

Figure 31B:
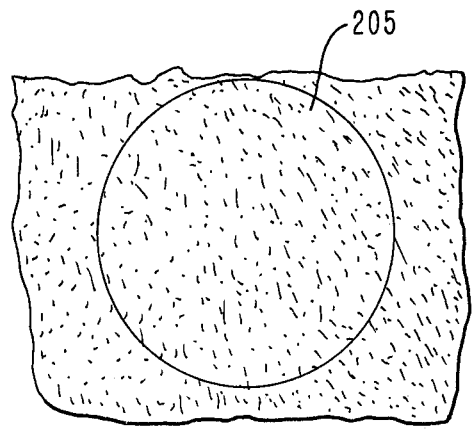

Registration data for the Y-coordinate may also be obtained from the left and right margin registration patterns. The white-to-dark and dark-to-white horizontal edges of the registration lines 78A, 78B, 78C (FIG. 17) of the patterns are long enough (0.030 inches) to provide voltage stabilization for interpolation measurements if the sweeping laser spot 205 (FIG. 31A) should straddle a horizontal edge such as line 206. The interpolation data may be translated into voltage and applied to the actuators of the flexible prism 33 (FIGS. 1, 2, 3, 29). When so actuated, the sweeping laser beam 25 may be deflected by the flexible prims 33 and brought into Y-coordinate registration with the circuit pattern. After registration the Y-coordinates of the sweeping laser beam spots should preferably be such that the laser spots are tangent to a horizontal line as shown in FIGS. 31b, 33B. In FIG. 31B a spot 234B, may be entirely on a white area and a spot(s) 235B, may be entirely on a dark area with a horizontal line 230B mutually tangent between the spots. Thus after registration the photocells 36 (FIGS. 1, 29) respond to only white or dark signals for comparison of data images in the computer memory bank and no interpolation is required as in FIG. 33A. The registration of the Y-coordinate sweep lines to the workpiece 1 rather than to a fixed element of the inspection tool thus avoids ±.0005 inch mechanical registration errors, interpolations, and also accommodates Y-coordinate portions of skewed circuit patterns such as in FIGS. 14, 15, 16.

The expansion of the sintered design pattern dimensions of the workpiece 1 to the larger inspection pattern dimensions present decimal interpolation problems for a large portion of the Y-coordinate sweep lines and their X-coordinate intervals. After the X and Y registration at the upper left corner of the workpiece 1, FIG. 33B, the upper left line portions may be used as a datum line 50B for dimensional reference purposes. Thus an X or Y sintered coordinate of 0.9925 inches might become 0.9925/.828 = 1.19867 inches for inspection purposes, or 1198.67 scan lines or increments, and the number of 0.67 to the right of the decimal point may require interpolation. A similar expansion of the sintered 5.000 dimensions of the outline 50B, 5.000/.828 = 6.03847 inches or 6.038.47 scan lines or increments.

The method for avoiding interpolation by the 45° reference lines of the grating provides integer numbers for the increments along the laser sweep lines as the laser sweeps across circuit line edges on the workpiece 1. It was noted that in the sintered design pattern the 0.005 inch wide circuit lines were centered on a 0.005 inch X and/or Y matrix design grid and the edges of such lines coincided with a 0.0005 inch X and/or sub-grid. Thus the centers of such lines might have X and-/or Y coordinate addresses such as —5.0 or —0.0 with the last two digits being either 5.0 or 0.0 and where a - may be any number from 0 to 9. Likewise the edges of 0.005 inch wide lines centered on the 0.005 inch matrix grid have line edges 0.0025 inches offset from the center lines and would have addresses such as —2.5 or —7.5 with the last digits being 2.5 or 7.5. To obtain expanded inspection addresses with integer numbers the sintered design numbers may be multiplied by a factor of 1.2 rather than being divided by the shrinkage factor .828: such as —2.5 × 1.2 = 3. and 5.000 × 1.2 = 6.000 rather than —2.5/.828 = —3.0193 and 5.000/.828 = 6.038547. Note that multiplying by 1.2 provides integer address numbers with small dimensional errors and that dividing by 0.828 provides correct dimensional numbers that may include a decimal point and that the numerals to the right of the decimal point may require interpolation. However, by rotating the grating with its 45° reference lines about its pivot point at the X "datum line" by its motor 132 (FIG. 21) the length of the laser sweep line across the 6000 grating lines may be increased from 6.000 inches to 6.038647 inches while still retaining 6000 lines or X-coordinate increments between the 0.0 inch "datum line" and the 6.038647 inch dimension. Thus the grating increments may be registered to the vertical line edges of a circuit pattern having a "nominal" shrinkage factor of 0.828. Similar Y-coordinate registration may be accomplished by increasing the rotational speed of the cylinder 9 by the stepping motor 179 (FIG. 30) whereby 6000 sweep lines may be spread over a "nominal" dimension of 6.038647 inches as previously described. Accommodation and registration for other "nominal" dimensions resulting from sintering shrinkage factors other than 0.828 may be similarly accomplished.

An X and/or Y pre-inspection shrinkage and/or expansion factor of ±.001 inch relative to "nominal" dimensions may be accommodated for registration purposes by accurately positioning eight or more periodically spaced registration patterns in the left and right margins of the workpiece 1. Such periodic registration patterns may be used to periodically apply correction signal to the actuators of the grating and the flexible prism as the workpiece 1 progress through the inspection tool. Thus the laser sweep line 237B (FIG. 33B) and its increments may be suitably registered to edge lines 232B, 233B in the lower right corner of the circuit line pattern as shown.

In the preferred method the combined result of registering the laser raster scan pattern to the workpiece circuit pattern as described above may be that each increment of a laser sweep line sees only entirely white areas or entirely dark areas and no precise interpolations of line edge positions is required for the inspection of an acceptable "near perfect" workpiece. By avoiding precise interpolation inspection speed is significantly increased. However, in a workpiece that may be other than "near perfect" there may be occasional errors attributable to out of position edges of circuit lines and via hole caps or random edges of possible electrical short and open circuits, etc. Such errors may be present if a white and/or dark line edge may be within a laser scan line spot increment when a correct spot should "see" either entirely white or dark increment areas. Approximte photocell voltage measurements of such errors rather than a precise interpolation of line edge positions are adequate for inspection "accept" and/or "reject" purposes and permit an increase in inspection speed. In a well registerd circuit pattern the design may be such that if a white increment spot area were to slightly intrude into what should have been on entirely dark increment spot area such that the photocell response voltage, without time for complete voltage response stabilization, might be only ¼ or less above the dark response level, the dark increment spot may be "accepted". Likewise if a dark increment spot area were to slightly intrude into a white increment spot area the white voltage response might be reduced by only ¼ or less and the white increment spot may be "accepted". However if the voltage increases or reductions from such intrusions were to be ½ or more the workpiece may be "rejected". The diffeerence between ¼ volage "acceptance" and ½ voltage "rejection" may be used as an intermediate "quard band" where either "accept" or "reject" events occur due to electrical noise levels, approximate photocell voltage level responses and/or second order mechanical errors, etc.

Thus in overall summary, the reduction of cumulative errors in the preferred configuration of the inspection tool may allow an inspection accuracy considerably smaller than ±.001 inch over a 6 × 6 inch square circuit pattern area of a workpiece(s), and complies with the stacking, laminating, and sintering constraints previously described relative to FIG. 9.

Although the invention has been described with a certain degree of particularity, it is understood that the present disclosure has been made only by way of example and that numerous changes in the details of construction and the combination and arrangement of parts and the mode of operation may be made without departing from the spirit and the scope of the invention as hereinafter claimed.

What is claimed is:

1. An inspection tool comprising: first means to feed a workpiece to be inspected into a work zone, said workpiece having a pattern thereon to be inspected; a source of coherent light and second means to effect a sweep of said coherent light across said work zone; first drive means connected to said second means to effect said sweep; a gear train connected to said first drive means and said first means to effect synchronous operation of said first and second means; a differential gear system in said gear train intermediate said first and second means; and a second drive means connected to said differential gear system whereby upon actuation of said second drive means variations in the speed of said first means may be obtained.

2. An inspection tool in accordance with claim 1 wherein said means to effect a sweep of said coherent light across said work zone comprises a mirror; means supporting said mirror for rotation in the intended path of the beam of coherent light from said source of coherent light, and first drive means for effecting rotation of said mirror.

3. An inspection tool in accordance with claim 2 wherein said mirror contains a plurality of facets.

4. An inspection tool in accordance with claim 2 including lens means for focussing said sweep of coherent light into a beam.

5. An inspection tool in accordance with claim 1 wherein said means to feed a workpiece into a work zone comprises a cylinder mounted for rotation.

6. An inspection tool in accordance with claim 5 wherein said cylinder includes means on the surface thereof for engagement with a workpiece.

7. An inspection tool in accordance with claim 5 and including a web of flexible material for engagement with a workpiece, and means on said cylinder for engagement with said flexible material to effect movement of said flexible material as said cylinder rotates.

8. An inspection tool in accordance with claim 5 including means for detecting the position of said cylinder during any one rotation thereof.

9. An inspection tool in accordance with claim 8 including means for comparing the position of said cylinder with the position said cylinder should be in at a predetermined time.

10. An inspection tool in accordance with claim 5 including means to actuate said second drive means responsive to differences in the length of a workpiece relative to a nominal workpiece.

11. An inspection tool in accordance with claim 5 including light detector means for receiving light reflected from a workpiece in said work zone from said sweep of coherent light, a prism mounted for rotation in a frame in the path of said sweep of coherent light, and actuator means to effect rotation of at least a portion of said prism, and energizing means to energize said actuator at predetermined times.

12. An inspection tool in accordance with claim 11 wherein said prism is flexible and said workpiece to be inspected includes Y axis alignment marks thereon for indicating the position of said workpiece along an axis transverse to said work zone, and means responsive to said first light detector means for actuating said energizing means to effect registration of said sweeping coherent light across said work zone with said alignment marks by rotation of at least said one end of said flexible prism.

13. An inspection tool in accordance with claim 12 including a pair of upstanding frame members at oppositelongitudinal ends of said prism, shaft and bearing means connected to opposite longitudinal ends of said prism, connecting said frame members thereto and along the longitudinal axis of said prism.

14. An inspection tool in accordance with claim 13 including means to grip said prism inwardly of said frame members and adjacent thereto; an offset portion of said gripping means, said first and second actuator means each comprising push-pull actuators connected to an associated frame member and connected to said offset portion to effect rotation of said prism about its longitudinal axis.

* * * * *